(12) United States Patent
Duerig et al.

(10) Patent No.: US 12,702,572 B2
(45) Date of Patent: Aug. 11, 2026

(54) DUCTUS ARTERIOSUS AND SEPTAL CONDUIT IMPLANTS AND RELATED DELIVERY SYSTEMS AND METHODS

(71) Applicant: Starlight Cardiovascular, Inc., San Diego, CA (US)

(72) Inventors: Thomas Duerig, Fremont, CA (US); Steven John, Fremont, CA (US); Mark Juravic, Encinitas, CA (US); Vrad W. Levering, Oakland, CA (US); Kathryn A. Olson, San Diego, CA (US); Beverly T. Tang, La Jolla, CA (US)

(73) Assignee: Starlight Cardiovascular, Inc., San Diego, CA (US)

(*) Notice: Subject to any disclaimer, the term of this patent is extended or adjusted under 35 U.S.C. 154(b) by 416 days.

(21) Appl. No.: 18/569,378

(22) PCT Filed: Jun. 16, 2022

(86) PCT No.: PCT/US2022/033872
§ 371 (c)(1),
(2) Date: Dec. 12, 2023

(87) PCT Pub. No.: WO2022/266378
PCT Pub. Date: Dec. 22, 2022

(65) Prior Publication Data

US 2025/0025321 A1 Jan. 23, 2025

Related U.S. Application Data

(60) Provisional application No. 63/211,768, filed on Jun. 17, 2021.

(51) Int. Cl.
*A61F 2/89* (2013.01)
*A61F 2/82* (2013.01)
(Continued)

(52) U.S. Cl.
CPC .......... *A61F 2/89* (2013.01); *A61F 2002/821* (2013.01); *A61F 2002/825* (2013.01);
(Continued)

(58) Field of Classification Search
CPC .... A61F 2/95; A61F 2/915; A61F 2002/8486; A61F 2002/9505; A61F 2002/9155;
(Continued)

(56) References Cited

U.S. PATENT DOCUMENTS

| | | | |
|---|---|---|---|
| 5,261,878 | A | 11/1993 | Galindo |
| 5,741,333 | A | 4/1998 | Frid |

(Continued)

FOREIGN PATENT DOCUMENTS

| | | | |
|---|---|---|---|
| CA | 2261044 | A1 | 1/1998 |
| DE | 102014115337 | A1 | 4/2016 |
| EP | 3254648 | A1 | 12/2017 |

OTHER PUBLICATIONS

Extended European Search Report re 22825862.0-1113 / 4351486 PCTUS2022033872 dated Mar. 31, 2025 (13 pages).

(Continued)

*Primary Examiner* — Tuan V Nguyen
(74) *Attorney, Agent, or Firm* — Aurora Consulting LLC; Tiffany Miller; Ashley Sloat

(57) ABSTRACT

Embodiments of stents for treating congenital heart defects and related delivery systems are provided. The devices described herein are configured for insertion into a blood vessel lumen to maintain a patency of a conduit and to balance flexibility and radial resistive force for delivery through a microcatheter. The device described herein are configured to transition from a crimped configuration to an expanded configuration. In the crimped configuration, a crimped diameter of the devices is less than about 0.7 mm. In the expanded configuration, the devices are configured to
(Continued)

have an expansion diameter of greater than about 3 mm measured at the body section. The devices described herein are configured to have a radial resistive force greater than about 0.20 N/mm at 1 mm of compression in the expanded configuration. Various devices having these features are described herein.

22 Claims, 51 Drawing Sheets

(51) Int. Cl.
*A61F 2/848* (2013.01)
*A61F 2/915* (2013.01)

(52) U.S. Cl.
CPC ................. *A61F 2002/8486* (2013.01); *A61F 2002/91583* (2013.01); *A61F 2250/001* (2013.01); *A61F 2250/0037* (2013.01); *A61F 2250/0039* (2013.01)

(58) Field of Classification Search
CPC .. A61F 2002/91558; A61F 2002/91566; A61F 2002/91575; A61F 2002/91583; A61F 2002/9534; A61F 2002/9528
See application file for complete search history.

(56) References Cited

U.S. PATENT DOCUMENTS 5,827,268 A 10/1998 Laufer
6,336,938 B1 1/2002 Kavteladze et al.
6,623,518 B2 9/2003 Thompson et al.
6,814,746 B2 11/2004 Thompson et al.
7,527,644 B2 5/2009 Mangiardi et al.
7,731,741 B2 6/2010 Eidenschink
7,731,742 B2 6/2010 Schlick et al.
7,763,064 B2 7/2010 Pinchasik
8,414,635 B2 4/2013 Hyodoh et al.
8,579,958 B2 11/2013 Kusleika
9,101,504 B2 8/2015 Tippett et al.
9,259,336 B2 2/2016 Schaeffer et al.
9,408,952 B2 8/2016 Sudhir et al.
9,480,559 B2 11/2016 Vidlund et al.
10,092,429 B2 10/2018 Krolik et al.
10,568,781 B2 2/2020 Noel
10,932,786 B2 3/2021 McNamara et al.
11,246,706 B2 2/2022 Dale et al.
11,911,305 B2 2/2024 Smith et al.
2003/0135266 A1 7/2003 Chew et al.
2004/0220585 A1 11/2004 Nikolchev
2006/0111771 A1* 5/2006 Ton ........................ A61F 2/962 623/1.15
2006/0265056 A1 11/2006 Nguyen et al.
2007/0055358 A1 3/2007 Krolik et al.
2009/0062839 A1 3/2009 Kurrus
2009/0099592 A1 4/2009 Buiser et al.
2009/0306706 A1 12/2009 Osypka
2011/0295353 A1 12/2011 Harris et al.
2012/0316597 A1 12/2012 Fitz et al.
2014/0277119 A1 9/2014 Akpinar
2015/0045881 A1 2/2015 Lim
2015/0119931 A1 4/2015 Amplatz et al.
2015/0127082 A1 5/2015 Sudhir et al.
2015/0374486 A1* 12/2015 Dickinson ................. A61F 2/07 623/1.14
2016/0120550 A1 5/2016 McNamara et al.
2017/0340433 A1 11/2017 Berra et al.
2018/0049859 A1 2/2018 Stoppenhagen et al.
2018/0049892 A1 2/2018 Henkes et al.
2018/0272044 A1 9/2018 Hossainy et al.
2019/0038393 A1 2/2019 Banco et al.
2019/0060052 A1 2/2019 Harrison et al.
2019/0083076 A1 3/2019 Alanbaei
2020/0093620 A1 3/2020 Fischer et al.
2020/0188098 A1 6/2020 Alkhatib et al.
2020/0254228 A1 8/2020 Taft et al.
2020/0323667 A1 10/2020 Garcia Torres et al.
2020/0391016 A1 12/2020 Passman et al.
2021/0228386 A1 7/2021 Sachar et al.

OTHER PUBLICATIONS

International Search Report dated Nov. 17, 2022 re PCT/US22/33872 (5 pages).
Written Opinion dated Nov. 17, 2022 re PCT/US22/33872 (13 pages).
Akay, Emrah et al. article titled "State 1 hybrid palliation of hypoplastic left heart syndrome: an initial experience in pulmonary trunk approach, procedural modifications, and complication management," Turkish Journal of Medical Sciences, Research Article, doi:10.3906/sag-1903-143, pp. 1374-1380
International Preliminary Report on Patentability re PCT/US2022/033872 dated Dec. 14, 2023 (14 pages).
International Search Report dated Dec. 11, 2023 re PCT/US23/68516 (2 pages).
Written Opinion dated Dec. 11, 2023 re PCT/US23/68516 (7 pages).

* cited by examiner 2500
2530
2560
2540
2550
2520
2510

2400
2422
2410
2420
2430

2300
2330
2310
2340
2320

DUCTUS ARTERIOSUS AND SEPTAL CONDUIT IMPLANTS AND RELATED DELIVERY SYSTEMS AND METHODS

CROSS-REFERENCE TO RELATED APPLICATIONS

This application is a 35 U.S.C. 371 National Stage filing for PCT Application Ser. No. PCT/US2022/033872, filed Jun. 16, 2022; which claims the priority benefit of U.S. Provisional Patent Application Ser. No. 63/211,768, filed Jun. 17, 2021, the contents of which are herein incorporated by reference in their entirety.

STATEMENT REGARDING FEDERALLY SPONSORED RESEARCH OR DEVELOPMENT

This disclosure was made with government support under Grant No. 1R43HL158304-01A1 awarded by the National Institutes of Health. The government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application relates to the field of cardiovascular implants, in particular stents designed for congenital heart defects.

BACKGROUND

The technical challenges faced by pediatric cardiovascular physicians (surgeons and interventionalists alike) have long been ignored, forcing them to use devices designed for adults and different conditions to treat ailing babies with very specific anatomical considerations. One such case is in the sustained opening of the ductus arteriosus, a natural conduit that exists in all newborns but closes shortly after birth. Another instance is the need to create or maintain an opening in the septum between two chambers in the heart (e.g., left and right atria), a septal conduit, to cause mixing of oxygenated and deoxygenated blood for the health of the patient.

In certain congenital heart defects, it is crucial to mix systemic and pulmonary circulations, including maintaining ductal patency and/or providing a septal conduit between the right and left atria for the newborn to survive without surgical intervention. Although stent-like devices exist to address numerous cardiovascular conditions, there are no specifically-designed devices to maintain patency of the ductus arteriosus or septal conduit in neonates. Consequently, reintervention, morbidity and mortality associated with the current standard of care is unacceptably high. For example, pediatric interventional cardiologists currently repurpose adult coronary artery stents for the ductus, and all-cause ductus reintervention is about 47%.

Thus, there is a need for a device that properly maintains patency of the ductus arteriosus in neonates. Further, there exists a need for a device that provides communication between the right and left atria as a way to provide a pressure-relief solution to the pulmonary circulation, decrease the size of a naturally-occurring ASD, or decrease an access port in transseptal procedures in children born with critical congenital heart defects (e.g., where atrial-level mixing is appropriate) that decreases morbidity and mortality compared with atrial stenting.

SUMMARY

One aspect of the present disclosure is directed to a device for insertion into a blood vessel lumen for maintaining a patency of a ductus arteriosus. The device is configured for delivery through a microcatheter. The devices comprises: a first end section comprising a first plurality of struts configured to expand to define a proximal face having a first diameter; a second end section comprising a second plurality of struts configured to expand to define a distal face having a second diameter; a body section extending between the first end section and the second end section and defining a third diameter, the body section having a third plurality of struts; and a device lumen extending through the first end section, the body section, and the second end section such that blood is configured to flow through the device lumen.

In any of the preceding embodiments, the device is configured to transition from a crimped configuration to an expanded configuration, such that, in the crimped configuration, a crimped diameter of the device is less than about 0.7 mm and, in the expanded configuration, the device is configured to expand to an expansion diameter of greater than about 3 mm measured at the body section.

In any of the preceding embodiments, the device, in the expanded configuration, has a radial resistive force greater than about 0.20 N/mm at 1 mm of compression.

In any of the preceding embodiments, in the expanded configuration, the first diameter of the proximal face is about 20% to about 50% larger than the third diameter of the body section.

In any of the preceding embodiments, in the expanded configuration, the second diameter of the distal face is about 20% to about 50% larger than the third diameter of the body section.

In any of the preceding embodiments, in the expanded configuration, the first diameter of the proximal face is about 20% to about 50% larger than the third diameter of the body section, and when, in the expanded configuration, the second diameter of the distal face is about 20% to about 50% larger than the third diameter of the body section.

In any of the preceding embodiments, the first diameter of the proximal face is about 20% to about 30% larger than the third diameter of the body section and the second diameter of the distal face is about 20% to about 30% larger than the third diameter of the body section.

In any of the preceding embodiments, each of the first plurality of struts has a first length, each of the second plurality of struts has a second length, and each of the third plurality of struts has a third length.

In any of the preceding embodiments, the third length of each of the third plurality of struts in about 1 mm to about 2 mm.

In any of the preceding embodiments, the first length of each of the first plurality of struts and the second length of each of the second plurality of struts is about 2.5 mm to about 4 mm.

In any of the preceding embodiments, the first plurality of struts of the first end section is arranged in one or more first rings.

In any of the preceding embodiments, the one or more first rings of the first end section comprise a first terminal ring comprising a first terminal plurality of struts, a first penultimate ring comprising a first penultimate plurality of struts, and a first antepenultimate ring comprising a first antepenultimate plurality of struts.

In any of the preceding embodiments, a first terminal strut length is longer than a first penultimate strut length, which is longer than a first antepenultimate strut length.

In any of the preceding embodiments, in the expanded configuration, adjacent first struts in each ring of the one or more first rings form a substantially constant angle.

In any of the preceding embodiments, the substantially constant angle is between about 50 degrees to about 70 degrees.

In any of the preceding embodiments, the substantially constant angle is between about 60 degrees to about 70 degrees.

In any of the preceding embodiments, the one or more first rings comprise 2 to 5 first rings.

In any of the preceding embodiments, adjacent first rings in the first end section are connected via 3 to 9 first bridges.

In any of the preceding embodiments, each first bridge has a first length between about 0.1 mm and about 0.25 mm.

In any of the preceding embodiments, the second plurality of struts of the second end section is arranged in one or more second rings.

In any of the preceding embodiments, the one or more second rings of the second end section comprise a second terminal ring comprising a second terminal plurality of struts, a second penultimate ring comprising a second penultimate plurality of struts, and a second antepenultimate ring comprising a second antepenultimate plurality of struts.

In any of the preceding embodiments, a second terminal strut length of a second terminal strut is longer than a second penultimate strut length of a second penultimate strut, which is longer than a second antepenultimate strut length of a second antepenultimate strut.

In any of the preceding embodiments, in the expanded configuration, adjacent second struts in each ring of the one or more second rings form a substantially constant angle.

In any of the preceding embodiments, the substantially constant angle is between about 50 degrees to about 70 degrees.

In any of the preceding embodiments, the substantially constant angle is between about 60 degrees to about 70 degrees.

In any of the preceding embodiments, the one or more second rings comprise 2 to 5 second rings.

In any of the preceding embodiments, the first plurality of struts of the first end section is arranged in one or more first rings and the second plurality of struts of the second end section is arranged in one or more second rings.

In any of the preceding embodiments, a terminal ring of the proximal face comprises a first terminal plurality of struts that each have a first length that is increased by about 100% to about 250% relative to a third length of each of the third plurality of struts.

In any of the preceding embodiments, a terminal ring of the distal face comprises a second terminal plurality of struts that each have a second length that is increased by about 100% to about 250% relative to a third length of each of the third plurality of struts.

In any of the preceding embodiments, adjacent second rings in the second end section are connected via 3 to 9 second bridges.

In any of the preceding embodiments, each second bridge has a second length between about 0.1 mm and about 0.25 mm.

In any of the preceding embodiments, the first end section and the second end section are configured to anchor the device in at least a portion of an aorta ostium and at least a portion of a pulmonary artery ostium, respectively, such that the body section spans a ductus arteriosus.

In any of the preceding embodiments, the third plurality of struts of the body section is substantially parallel to a longitudinal axis of the device in the expanded configuration.

In any of the preceding embodiments, a terminal subset at the proximal face of the first plurality of struts forms a proximal angle with respect to a longitudinal axis of the device.

In any of the preceding embodiments, the proximal angle is about 30 degrees to about 110 degrees.

In any of the preceding embodiments, the proximal angle is about 45 degrees to about 90 degrees.

In any of the preceding embodiments, a terminal subset at the distal face of the second plurality of struts forms a distal angle with respect to a longitudinal axis of the device.

In any of the preceding embodiments, the distal angle is about 30 degrees to about 110 degrees.

In any of the preceding embodiments, the distal angle is about 45 degrees to about 90 degrees.

In any of the preceding embodiments, the device further comprises one of: an anti-thrombogenic coating, an anti-proliferative coating, and a friction reducing coating.

In any of the preceding embodiments, the device comprises a drug-eluting coating.

Another aspect of the present disclosure is directed to a device for insertion into a blood vessel lumen for maintaining a patency of a ductus arteriosus. The device being configured for delivery through a microcatheter. The device comprises: a first end section comprising a first plurality of struts configured to expand to define a proximal face having a first diameter; a second end section comprising a second plurality of struts configured to expand to define a distal face having a second diameter; a body section extending between the first end section and the second end section and defining a third diameter, the body section having a third plurality of struts; and a device lumen extending through the first end section, the body section, and the second end section such that blood is configured to flow through the device lumen.

In any of the preceding embodiments, the device is configured to transition from a crimped configuration to an expanded configuration, such that, in the crimped configuration, a crimped diameter of the device is less than about 0.7 mm and, in the expanded configuration, the device is configured to expand to an expansion diameter of greater than about 3 mm measured at the body section.

In any of the preceding embodiments, in the expanded configuration, each of the first diameter of the proximal face and the second diameter of the distal face is about 20% to about 50% larger than the third diameter of the body section.

In any of the preceding embodiments, the device, in the expanded configuration, has a radial resistive force greater than about 0.20 N/mm at 1 mm of compression.

In any of the preceding embodiments, in the expanded configuration, each of the first diameter of the proximal face and the second diameter of the distal face is larger by about 1 mm to about 2 mm than the third diameter of the body section.

Another aspect of the present disclosure is directed to a system for delivering a device into a lumen of a ductus arteriosus to maintain a patency of the lumen of the ductus arteriosus. The system comprises: a delivery system comprising a microcatheter and a pusherwire. The pusherwire is configured to be advanced through a lumen defined by the microcatheter. The pusherwire comprises a first hub and an implant receiving section. The implant configured to be pushed by the first hub when loaded onto the implant receiving section of the pusherwire. The implant comprises: a first end section comprising a first plurality of struts configured to expand to define a proximal face having a first diameter; a second end section comprising a second plurality of struts configured to expand to define a distal face having a second diameter; a body section extending between the first end section and the second end section and defining a third diameter, the body section having a third plurality of struts; and an implant lumen extending through the first end section, the body section, and the second end section such that blood is configured to flow through the implant lumen.

In any of the preceding embodiments, the implant is configured to transition from a crimped configuration to an expanded configuration upon exiting the microcatheter, such that, in the crimped configuration, a crimped diameter of the implant is less than about 0.7 mm and, in the expanded configuration, the implant is configured to expand to an expansion diameter of greater than about 3 mm measured at the body section.

In any of the preceding embodiments, in the expanded configuration, the implant has a radial resistive force greater than about 0.20 N/mm at 1 mm of compression.

In any of the preceding embodiments, the first hub comprises a female connector and the proximal face of the implant comprises a complementary male connector configured to interact the female connector of the first hub.

In any of the preceding embodiments, the proximal face comprises a plurality of radiopaque markers such that the first hub is configured to push the plurality of radiopaque markers to deploy the implant.

In any of the preceding embodiments, the pusherwire further comprises a second hub.

In any of the preceding embodiments, the second hub is configured to interact with an inner diameter of the distal face of the implant such that the pusherwire is configured to be displaced proximally during implant deployment.

In any of the preceding embodiments, the first hub defines one or more apertures configured to receive contrast therethrough.

In any of the preceding embodiments, the delivery system further comprises a transfer sheath.

Another aspect of the present disclosure is directed to an implant configured for treatment of a congenital heart defect. The implant is configured for delivery through a microcatheter. The implant comprises: a first end section comprising a first plurality of struts configured to expanded to define a proximal face having a first diameter; a second end section comprising a second plurality of struts configured to expand to define a distal face having a second diameter; a body section extending between the first end section and the second end section and defining a third diameter, the body section having a third plurality of struts; and a device lumen extending through the first end section, the body section, and the second end section such that blood is configured to flow through the device lumen.

In any of the preceding embodiments, the implant is configured to transition from a crimped configuration to an expanded configuration, such that, in the crimped configuration, a crimped diameter of the device lumen is less than about 0.7 mm and, in the expanded configuration, the implant is configured to expand to an expansion diameter of greater than about 3 mm measured at the body section.

In any of the preceding embodiments, the implant, in the expanded configuration, has a radial resistive force greater than about 0.20 N/mm at 1 mm of compression.

In any of the preceding embodiments, the congenital heart defect is a septal defect in a heart of a patient, such that the implant is configured to be delivered into a septal conduit between two chambers of the heart of the patient.

In any of the preceding embodiments, the congenital heart defect is ductus arteriosus, such that the implant is configured to be inserted into the ductus arteriosus to maintain a patency of the ductus arteriosus.

In any of the preceding embodiments, one or more terminal crowns of the distal face has an angle of about 30% to about 110% relative to a longitudinal axis of the body section.

In any of the preceding embodiments, one or more terminal crowns of the proximal face has an angle of about 30% to about 110% relative to a longitudinal axis of the body section.

Another aspect of the present disclosure is directed to a method of maintaining communication through an atrial septum of a heart. The method comprises advancing a distal end of a stent delivery system into a right atrium, the stent delivery system comprising a microcatheter. The method further comprises advancing the distal end of the stent delivery system across a septum; deploying a distal end section of a stent in a left atrium to anchor the distal end section of the stent in a wall of the septum facing the left atrium; deploying a body section of the stent in the septum; and deploying a proximal end section of the stent in the right atrium to anchor the proximal end section of the stent in the wall of the septum facing the right atrium.

In any of the preceding embodiments, the stent has a radial resistive force of greater than or equal to about 0.2 N/mm at about 1 mm of compression.

In any of the preceding embodiments, a diameter of one or both of a proximal end and the distal end of the stent is about 20% to about 40% larger than a diameter of the body section of the stent.

In any of the preceding embodiments, the advancing the distal end section of the stent delivery system across the septum comprises advancing the distal end section of the stent delivery system across one of: a foramen, an atrial septal defect, or a septostomy.

In any of the preceding embodiments, the deploying the distal end section of the stent in the left atrium comprises applying tension or force to a proximal end section of the stent delivery system to anchor the distal end section of the stent in the wall of the septum.

In any of the preceding embodiments, a length of the stent is about 3 mm to about 10 mm.

In any of the preceding embodiments, the diameter of the body section of the stent is about 4 mm to about 5 mm.

Another aspect of the present disclosure is directed to a method of maintaining a patent ductus arteriosus in a pediatric patient. The method comprises: deploying, using a microcatheter, a distal end section of a self-expanding stent at a first end of a lumen defined by a ductus arteriosus; anchoring at least a portion of a distal face of the distal end section of the self-expanding stent such that the distal face at least partially circumferentially covers a pulmonary artery ostium; deploying, using the microcatheter, a proximal end section of the self-expanding stent, such that a body section of the self-expanding stent covers an entire length of the lumen defined by the ductus arteriosus; and anchoring a least a portion of a proximal face of the proximal end section of the self-expanding stent such that the proximal face at least partially circumferentially covers an aortic ostium.

In any of the preceding embodiments, the self-expanding stent, when deployed, has a radial resistive force greater than or equal to about 0.2 N/mm at about 1 mm compression.

In any of the preceding embodiments, the method further comprises administering a prostaglandin to the pediatric patient to dilate the lumen defined by the ductus arteriosus of the pediatric patient.

Another aspect of the present disclosure is directed to a method of maintaining a patent ductus arteriosus in a pediatric patient where a diameter of a ductus arteriosus is larger than a diameter of a body section of a stent. The method comprises: deploying, using a microcatheter, a distal end section of a self-expanding stent at a first end of a lumen defined by the ductus arteriosus; anchoring at least a portion of a distal face of the distal end section of the stent such that the distal face at least partially circumferentially covers the distal end of the ductus arteriosus; deploying, using the microcatheter, a proximal end section of the stent, such that a body section of the stent is within an entire length of the lumen defined by the ductus arteriosus; and anchoring a least a portion of a proximal face of the proximal end section of the stent such that the proximal face at least partially circumferentially covers an ostium of an adjacent artery.

BRIEF DESCRIPTION OF THE DRAWINGS

The features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5A shows a Type I ductal anatomy; FIG. 5B shows a Type II ductal anatomy; and FIG. 5C shows a Type III ductal anatomy.

Figure 1A:
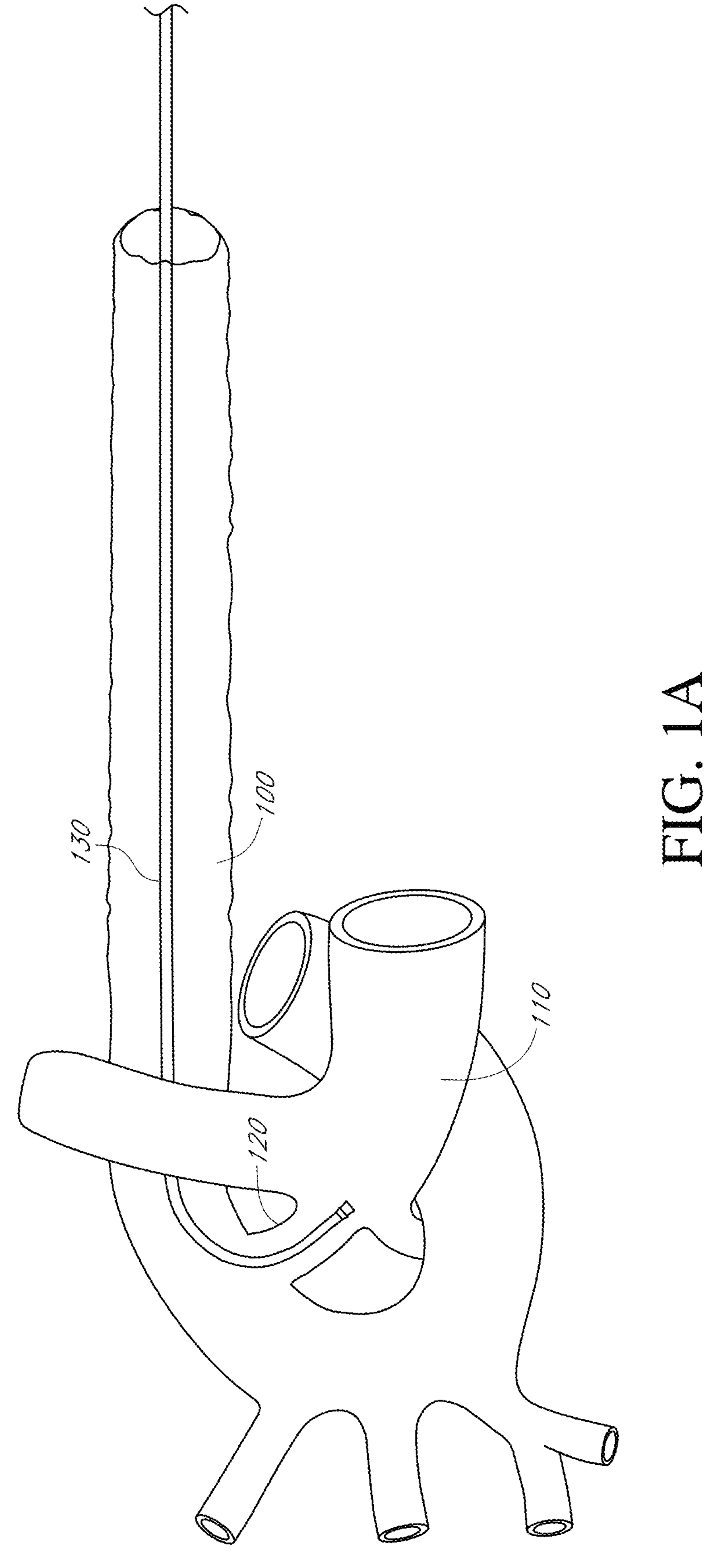
FIGS. 1A-1D show one embodiment of a method of maintaining a patent ductus arteriosus by approaching the ductus from the aorta.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Described herein are various embodiments of methods, stents, and delivery systems that may be used to treat congenital heart defects, such as patent ductus arteriosus and septal conduit defects. The various embodiments described herein are designed to address the technical challenges facing physicians treating neonates or pediatric patients including: right-sized delivery systems, end-to-end coverage of the defect (e.g., ductus or conduit), navigation and deployment through tortuous anatomy, stent anchoring in a dilated ductus or in a thick-walled septal conduit, and precise placement to avoid stent protrusion into the aorta and pulmonary arteries or into a heart chamber. Stents designed and tested specifically for this purpose and patient population will decrease reinterventions, morbidity, and potentially mortality for patients with ductal-dependent circulation or septal defects.

As used herein, a "user" may include, but should not be limited to, a physician, assistant, doctor, nurse, interventionalist, healthcare provider, technician, radiologist, or the like.

As used herein, a "patient" may include, but not be limited to, a fetus, neonate, pediatric, toddler, pre-mature baby, baby, or the like.

As used herein, "ductus" and "ductus arteriosus" may be used interchangeably.

In some embodiments, as used herein, "an entire length of the ductus" may be measured from an aorta ostium to a pulmonary artery ostium, based on anatomical imaging, measured from a first ductal end (e.g., at the aorta) to a second ductal end (e.g., at the pulmonary artery), measured along the outer edge of the ductus curvature, measured along the inner edge of the ductus curvature, measured through the centerline of the ductus curvature, or the like.

As used herein, "proximal" and "distal" depend on the approach taken with a delivery system. For example, if approaching the ductus from the aorta, then the pulmonary artery may be considered distal with respect to the aorta and delivery system. If approaching the ductus from the pulmonary artery, then the aorta may be considered distal with respect to the pulmonary artery and delivery system. For a septal conduit, if approaching the septum from the right atrium, then the left atrium may be considered distal with respect to the right atrium and the delivery system. As such, in some cases, first and second ends are used to replace proximal and distal terminology to illustrate the interchangeability of these terms and their dependency on the type of procedure being performed.

Introduction

Congenital heart defects (CHDs) are conditions that are present at birth and can affect the structure and function of a patient's heart. CHDs are the most common type of birth defect, affecting about 1% of babies born in the U.S. each year. Two types of CHDs are: (A) patent ductus arteriosus and (B) septal defects (e.g., atrial, ventricular, or atrioventricular septal defect), each of which will be described in turn below.

(A) Patent Ductus Arteriorsus

Approximately 2,000 babies are born in the U.S. yearly that could benefit from a ductus arteriosus stent, categorized into two groups: patients with ductal-dependent pulmonary circulation and patients with ductal-dependent systemic circulation. The devices, systems, and methods described herein provide an improved way to properly maintain patency of the ductus arteriosus in pediatric patients.

Patients with ductal-dependent pulmonary circulation are typically treated with Modified Blalock-Taussig Shunts (MBTS), a surgical procedure where the chest is opened, the patient is put on cardiopulmonary bypass (causing potential deleterious effects on brain development), and a plastic conduit is implanted to provide flow to the systemic and pulmonary circulations. MBTS carry a 7.2% risk of morbidity and 13.1% risk of mortality in the U.S. Alternatively, ductal stenting has shown non-inferior, and potentially superior, mortality over MBTS and provides ductal-dependent pulmonary circulation without the need for cardiopulmonary bypass. Stenting the ductus with repurposed (i.e., off label use) coronary stents that are conventionally available carries a 47% reintervention rate. Reintervention rates are higher when a portion of the stent extends into the pulmonary artery either partially or fully jailing one of the branch pulmonary arteries, which occurs in 21.9% of ductus stenting cases with repurposed coronary stents. A stent and delivery system designed and tested for maintaining ductus arteriosus patency could move patients from open surgery to a less invasive approach, with reduced mortality compared to MBTS and fewer reinterventions compared to stenting with repurposed coronary stents.

Patients with ductal-dependent systemic circulation typically have Hypoplastic Left Heart Syndrome (HLHS). The first procedure in a three-stage palliation for HLHS is typically performed in the first two weeks of life. A hybrid procedure that includes ductal stenting could prevent the need for putting these patients on bypass. Some facilities have had good results with hybrid stage I palliation procedures, but results are inconsistent and challenges using repurposed stents in the ductus remain. The stents, systems, and methods described herein address the HLHS patient population.

Issues with the convention of using repurposed stents in the ductus arteriosus include: 1) a lack of understanding of ductus tissue-stent interaction for selecting a stent with the proper radial force; 2) challenging measurement of the three-dimensional (3D) ductus arteriosus with two dimensional (2D) angiography, making stent sizing difficult; 3) mechanical properties of the stent and delivery system change the ductus tortuosity and length, further complicating stent sizing; 4) difficulty in precise stent placement to prevent protrusion into surrounding arteries; 5) delivery systems are designed for adult vessels, risking damage to the smaller, vulnerable blood vessels from percutaneous access to placement location; 6) delivery systems are not designed for the approach angles or deployment in tortuous ductus anatomies; and 7) difficulty anchoring the desired diameter of ductus stent to control blood flow due to the inability to precisely control ductus size at the time of stenting with prostaglandin titration.

Conventional coronary stents that are repurposed for ductal stenting in ductal-dependent pulmonary circulation are balloon-expandable, which are designed to push occlusive atherosclerotic disease out of the vessel lumen; this is not the use-case for ductal stenting, where stents need to perform in thin-walled, healthy vessels. Balloon-expandable coronary stents repurposed for ductal stenting have many limitations that make them sub-optimal for ductal stenting. For example, the implants are less conformable, as they generally take the shape of a straight balloon when delivered; they cannot elastically deform and rebound; they foreshorten with balloon deployment, making sizing more difficult; they have straight designs that have no additional anchoring features, requiring that the stent diameter be the same as the ductus diameter during implantation; and they are less durable in fatigue. Further, the delivery systems are typically stiff on the distal end due to the balloon-mounted stent, making it challenging to navigate tortuous anatomies without inducing vasospasm, often requiring a 4F sheath to cross the ductus, further risking spasm due to the large size of the sheath compared to vessel size. Additionally, stents that have sufficient flexibility while loaded in the delivery system to advance through the tortuous anatomy typically have insufficient radial force to maintain an open lumen.

Figure 4A:
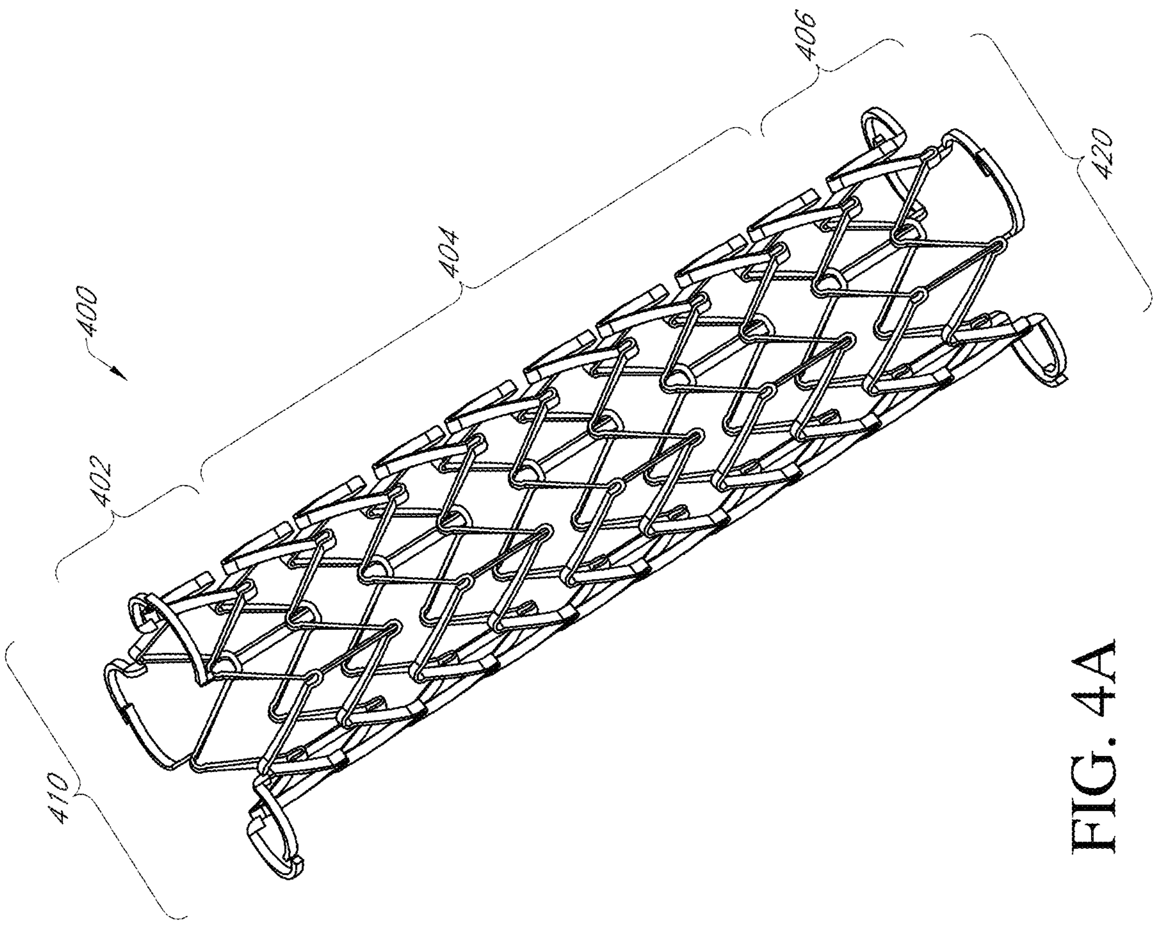
FIG. 4A shows an embodiment of a stent for maintaining a patent lumen or conduit.
Figure 4B:
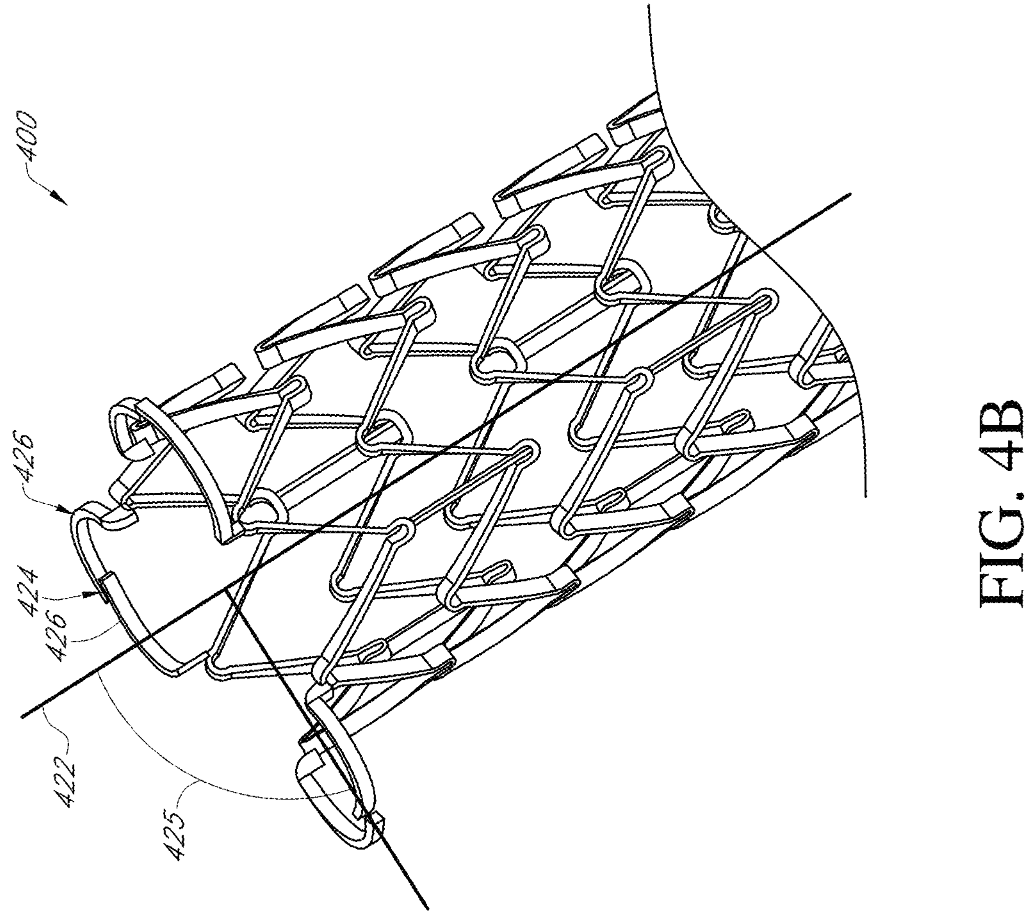
FIG. 4B shows a zoomed-in view of an end section of the stent of FIG. 4A.
Figures 5A, 5B, 5C:
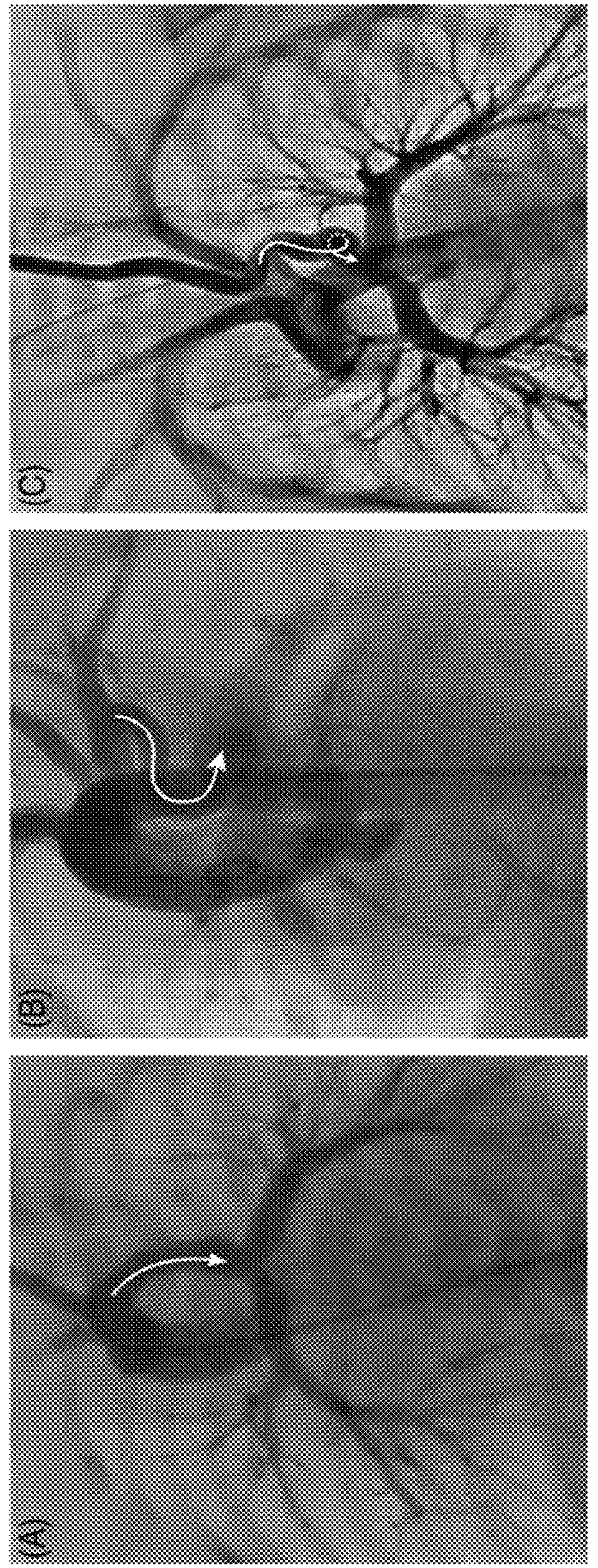
FIGS. 5A-5C show angiographic examples of various ductus anatomies.
Figure 6:
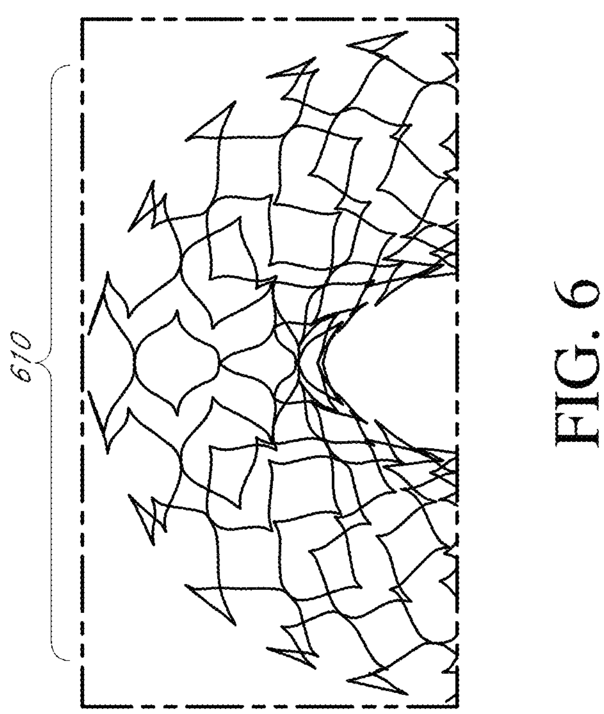
FIG. 6 shows another embodiment of a body section of a stent conforming to a hairpin turn.

FIGS. 5A-5C illustrate three major ductal anatomies encountered in ductal dependent pulmonary circulation. FIG. 5A shows a Type I ductal anatomy, for example a substantially straight or linear, shorter ductus. FIG. 5B shows a Type II ductal anatomy, for example a more tortuous, longer ductus. FIG. 5C shows a Type III ductal anatomy, for example a ductus having curves greater than 360 degrees. The present invention advantageously provides systems, devices, and methods for stenting shorter to longer ductus arteriosus, including those having the tortuous, looping ductus. It will be appreciated that ductus lengths may range from about 8 mm to about 28 mm but may also be shorter or longer depending on the patient's anatomy. Further, the devices, systems, and methods described herein may substantially conform to an anatomy of the ductus and reduce the likelihood of unnatural straightening or lengthening of the ductus. For example, as shown in FIG. 6, body section 610 is configured to conform to a hairpin turn within a patent lumen (such feature may be a feature of any of the body sections of any of the stents described herein). As such, any of the stents (or features thereof) and methods described herein, in particular those shown in FIGS. 1A-4B, 6-25D may be configured to treat any of ductal anatomies described above or elsewhere herein.

(B) Septal Defect

Approximately 20,000 babies are born in the U.S. each year with some form of septal defect (SD; atrial, atrioventricular, or ventricular). Currently, depending on the size of the conduit and the severity, cardiac catheterization or open-heart surgery are recommended to close the conduit and restore normal blood flow. However, in certain rare cases, stenting the septal conduit may be used as a treatment for ventricular hypertension due to outflow obstruction. For example, there are up to 16,000 patients born every year that could benefit from an atrial septostomy.

In a typical heart, the atria are the two upper chambers of the heart which are divided into the left and right atria by the atrial septum. In healthy children, the atrial septum prevents oxygenated and deoxygenated blood from mixing. A naturally occurring hole between the two atria, the patent foramen *ovale*, is present in fetal circulation but closes to be hemodynamically insignificant soon after birth. However, in some babies with congenital heart defects, pressure in the left atrium is too high or oxygenated and deoxygenated blood require atrial-level mixing, necessitating the creation of an opening between the two atria. Because the foramen *ovale* closes early in some babies, a septostomy device may be needed to create a new conduit. Conditions where creating a septal conduit is useful include: Hypoplastic Left Heart Syndrome (HLHS), Other Single Ventricle with Restrictive Septum, Transposition of Great Arteries (TGA) with Restrictive Septum, Pediatric Pulmonary Hypertension, Extracorporcal Membrane Oxygenation Decompression, and Pulmonary Vein Stenosis Conventionally, the atrial septum is crossed with a balloon, the balloon is inflated and then pulled across the atrial septum to rip it open. In balloon-assisted stenting, there is no control over the size of the opening in the septum, often resulting in generation of a large hole, which sometimes closes, so this is not done in patients who need a precise hole size. If a particular patient requires a precise hole size, a balloon-expandable stent is placed across the atrial septum and expanded to the desired diameter. The stent controls the diameter of the opening and ensures a reliable opening. However, there are several problems associated with current stents and delivery systems for the treatment of SD. For example, conventional stents or repurposed stents can migrate or be too long causing thrombosis risk and difficulty during placement. Conventional or repurposed stents may be tied in the middle to create an hourglass shape to prevent migration, but such solution is unsatisfactory. Further, for example, conventional or repurposed stents are not right-sized for the target anatomy for the pediatric patient population, resulting in difficulty in placement, which may also result in migration and/or thrombosis risk. Additionally, for example, delivery systems are not sized accordingly and are not sufficiently flexible for the target pediatric population, resulting in trauma to the vessels and heart during deployment.

Accordingly, stents that are created specifically for the treatment of SD or the creation of a septal conduit are needed to overcome the challenges of conventional or repurposed stents. The stents and delivery systems described herein overcome these challenges at least because: (1) the stents comprise first and/or second end sections that are flared such that the stent can be anchored in the septal conduit, thus preventing migration and/or extension in the atrial chambers; (2) the stents are configured to be crimped down to a diameter sufficient to be delivered through a microcatheter (by tuning strut length, strut thickness, strut width, crown number, bridge number, etc. as described elsewhere herein); and (3) the stents are configured to have sufficient radial resistive force, once expanded (by tuning strut length, strut thickness, strut width, crown number, bridge number, etc. as described elsewhere herein).

Various stent embodiments and delivery systems described herein may be used to treat CHDs, including septal defects, patent ductus arteriosus, and patent septal conduits. Further, various stent embodiments, delivery systems, and methods described herein overcome the technical challenges identified above. For example, the stents described herein may be deliverable using a microcatheter. Using a microcatheter imposes severe requirements on a size of device in a crimped state. However, such stents must also have sufficient radial force, in an expanded state, to prevent the patent ductus or septal conduit from closing. The stents described herein may be made using Nitinol configured to be shape set and thus self-expanding. The stents in an expanded state have a tailored radial force, as described elsewhere herein. Further, the stents described herein may be configured to be anchored in the ductus or septal conduit to provide end-to-end coverage of the lumen or conduit. Such anchoring may be achieved through a proximal and/or distal end section that includes one or more features for anchoring the stent in the conduit, as described elsewhere herein.

Various stent embodiments described herein include a first end section comprising a first plurality of struts configured to expanded to define a proximal face having a first diameter; a second end section comprising a second plurality of struts configured to expand to define a distal face having a second diameter; and a body section extending between the first end section and the second end section and defining a third diameter, the body section also having a third plurality of struts.

The first end section and/or second end section may include rows, struts, crowns, and/or bridges that are configured to act as flanges or anchoring mechanisms to anchor the strut relative to the anatomy. The first end section and/or second end section described herein may have a length of about 1 mm to about 3 mm; about 1.5 mm to about 2.5 mm; about 2 mm; etc. Each end section may comprise about 1 to about 5 rings and/or about 3 to about 9 bridges or connectors.

In some embodiments, the stent has a diameter of between about 3 mm to about 5 mm (five diameters at 0.5 mm increments) for ductal-dependent pulmonary circulation, a diameter between about 5 mm to about 10 mm (six diameters at 1 mm increments) for ductal dependent systemic circulation, and a diameter between about 4 mm to about 5 mm for septal conduits. The stent flanges, flares, or cuffs (of the first and/or second end sections), by anchoring the stent without the need for complete wall apposition, allow interventionalists to select a stent diameter smaller than the ductus or septal conduit without risk of stent migration, to optimize the ultimate ductus or conduit size, and therefore pulmonary blood flow after prostaglandin infusion is stopped (in the case of ductus arteriosus) or oxygenated and deoxygenated blood mixing (in the case of a septal conduit).

The stents described herein are in situ adaptable and allow deployment of a pre-shaped first end section (e.g., first flange or first flare) that anchors the stent at the distal end (e.g., ostia of the ductus at the pulmonary artery for ductal dependent pulmonary circulation or aorta for ductal dependent systemic circulation; or at a septal wall of a heart chamber) as well as a second end section (e.g., second flange or second flare) at the proximal end. The flanges on the proximal and distal ends ensure end-to-end coverage of the ductus or conduit.

Clinical results from ductus stenting have shown a significant improvement in mortality and emergent interventions in ductal-dependent pulmonary patients. When the stents are delivered to the anatomy and placed in a way that offers full coverage, they have been shown to be safe and effective, offering recent technical success rates of well over 90%, high survival rates, and a longer-term solution to prevent ductal closing than administering prostaglandins alone cannot achieve.

Methods

Figures 8A, 8B:
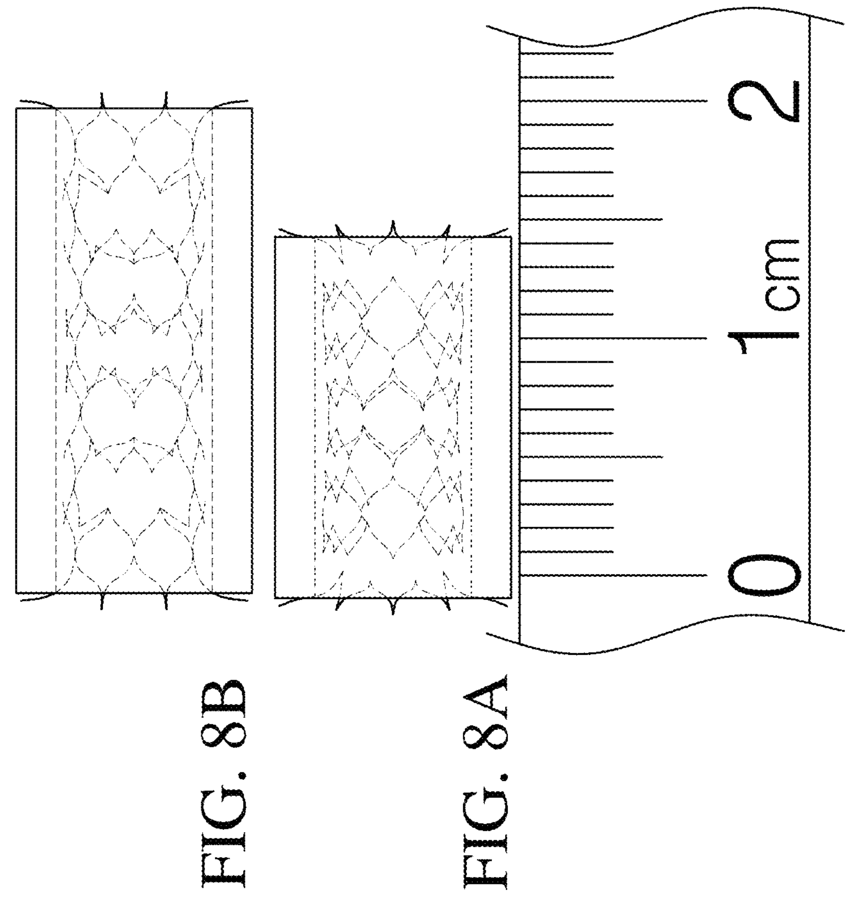
FIGS. 8A-8B show an example stent for maintaining a patent lumen or conduit in a first shortened configuration (FIG. 8A) and a second elongate or stretched configuration (FIG. 8B).

One embodiment of a method of deploying any of the stents described herein includes: navigating the microcatheter-based delivery system to the distal end of the ductus; unsheathing the distal end section (e.g., flange or flare) that engages the ostium of the ductus at the pulmonary artery wall; continuing to unsheathe the stent while applying light tension to effectively stretch the stent across the ductus; and deploying the proximal end section (e.g., flange) at the ostium of the ductus, thus ensuring end-to-end coverage between the end sections with no stent protrusion on either side of the ductus. This small augmentation of stent and ductus lengths by about 3 mm to about 5 mm allows the interventionalist to compensate for ductus length measurements that are inherently inaccurate by a few millimeters due to 2D measurement of a tortuous 3D ductal anatomy and modification of the ductus length during stent placement. This length-adjustability between end sections (e.g., flanges) enables coverage of the most common ductus lengths from about 8 mm to about 28 mm with only seven different stent lengths. For example, FIGS. 8A-8B show a stent in a first shortened configuration having a length of about 15 mm (FIG. 8A) and the same stent in a second elongate or stretched configuration having a length of about 20 mm (FIG. 8B). The stent shown in FIG. 8B is stretched (relative to the stent in FIG. 8A) to accommodate an about 5 mm difference in ductus length.

In some instances, as shown in FIGS. 1A-1D and FIGS. 2A-2D, a stent having anchoring features on a first and second end section can be partially (about 50%) deployed at the distal end of the ductus first (e.g., pulmonary artery) with the distal end section engaging the pulmonary artery wall adjacent to the ductus. The interventionalist may apply tension while deploying the second half of the stent to compress the length of the ductus arteriosus effectively and slightly. This small augmentation of ductus length allows the interventionalist to compensate for ductus length measurements that are inherently imprecise due to 2D measurement of a tortuous 3D ductal anatomy and modification of the ductus length due to stent placement. The distal and proximal end sections additionally provide a mechanism of anchoring the stent without complete wall apposition at the time of deployment. The anchoring mechanism at one or both of the end sections allows the stent to be deployed in a ductus that has a larger diameter than the stent diameter, without risk of stent migration downstream.

Figure 1B:
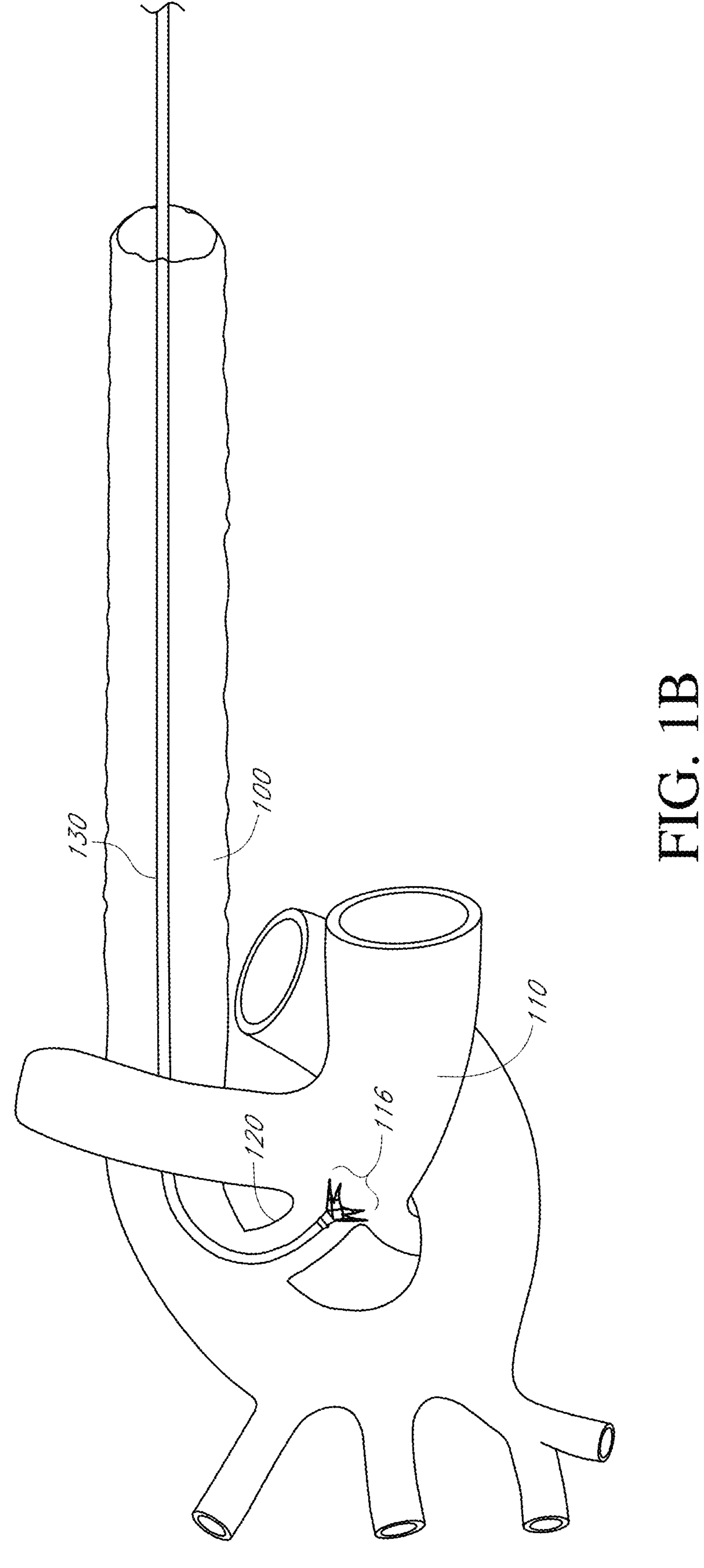
Figure 1C:
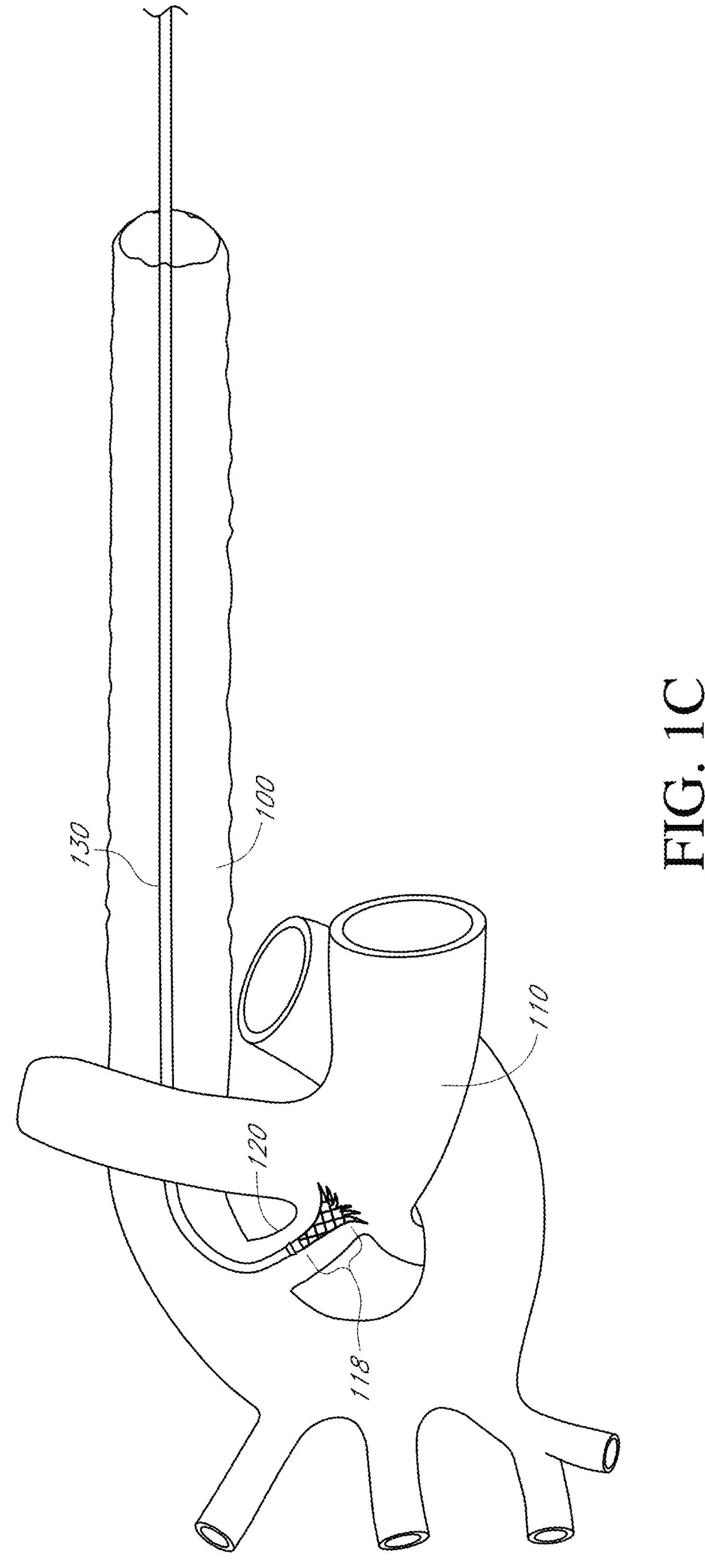
Figure 1D:
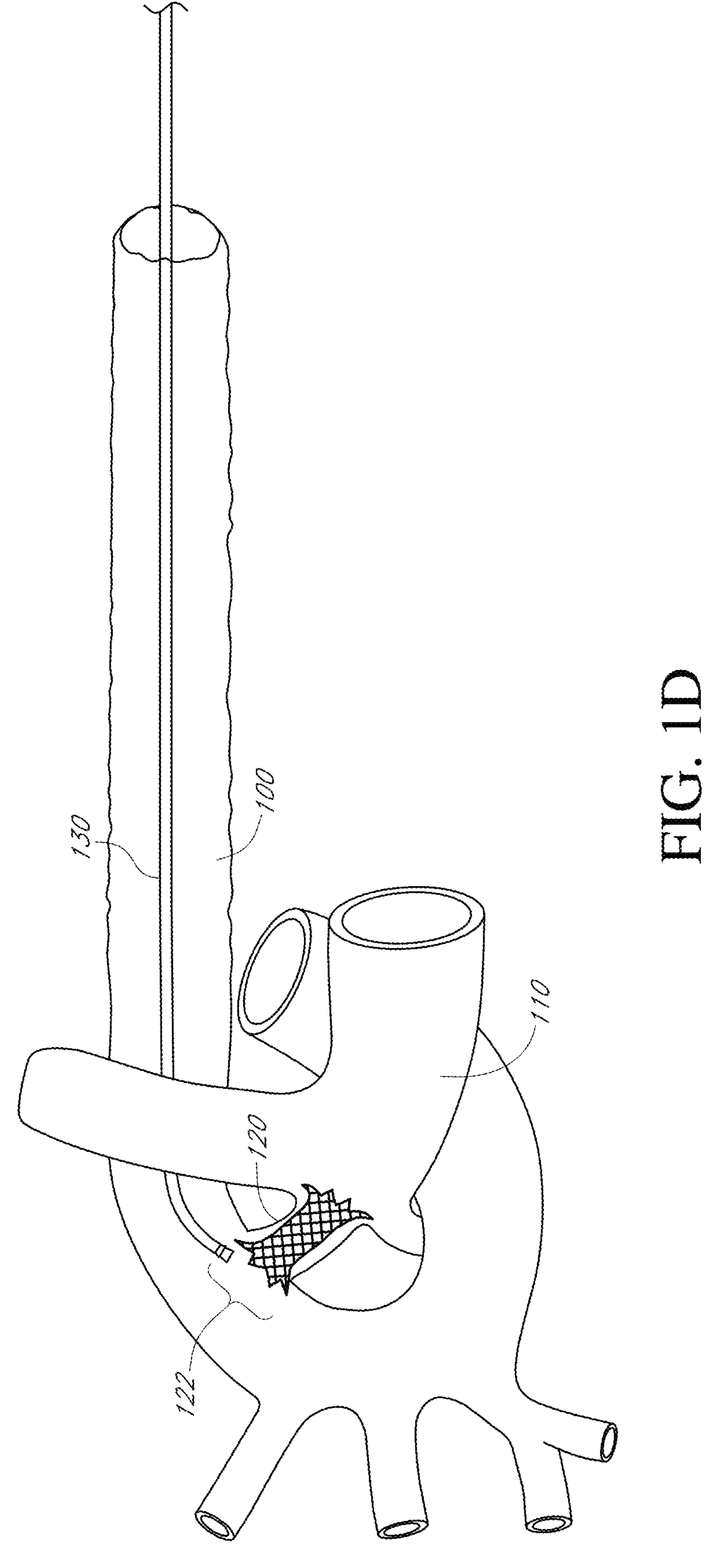

FIGS. 1A-1D and 2A-2D show two methods of deploying a stent in a ductus arteriosus. FIGS. 1A-1D show one embodiment of a method of delivering any of the stents described herein to a ductus arteriosus from an aorta to a pulmonary artery. FIG. 1A illustrates an embodiment of a method of advancing a delivery system 130 through an aorta 100 and through a ductus arteriosus 120 to approach a pulmonary artery 110. As shown in FIG. 1B, the delivery system 130 constrains a stent body, releases a first, or distal, end section 116 that expands outwardly to the diameter or a fraction of the lumen of the ductus 120. In some embodiments, the diameter of the stent is undersized relative to the diameter of the lumen defined by the ductus, for example, because of prostaglandin therapy or a selected size of the stent, as described elsewhere herein. The first end section 116, which may comprise any one or more of the features shown in FIGS. 3A-4B, 7, 9-14, 17A-17B, 19-25D, 27A-27B of any of the stent embodiments described herein, at least partially anchors at the ductus lumen and/or at least partially circumferentially covers the ostium of the pulmonary artery 110. The constrained (by the microcatheter) stent body 118 is released from the delivery system 130, as shown in FIG. 1C. In some embodiments, constrained rings of a stent body are individually released, released segment by segment (each segment comprising one or more rings or a plurality of rings), released subset by subset (a subset comprising one or more segments), or released in aggregate from the distal end of the delivery system and expanded until the entire length of the ductus is covered. A second, or proximal, end section is released and expands outward. The second end section 122, which may comprise any one or more of the features shown in FIGS. 3A-4B, 7, 9-14, 17A-17B, 19-25D, 27A-27B of any of the stent embodiments described herein, at least partially anchors at the lumen of the ductus 120 and/or at least partially circumferentially covers the ostium of the aorta 100, as shown in FIG. 1D. Advantageously, this method of delivering any of the stents described herein may be used to increase pulmonary circulation of the patient but may also be used to increase systemic circulation.

Figure 2A:
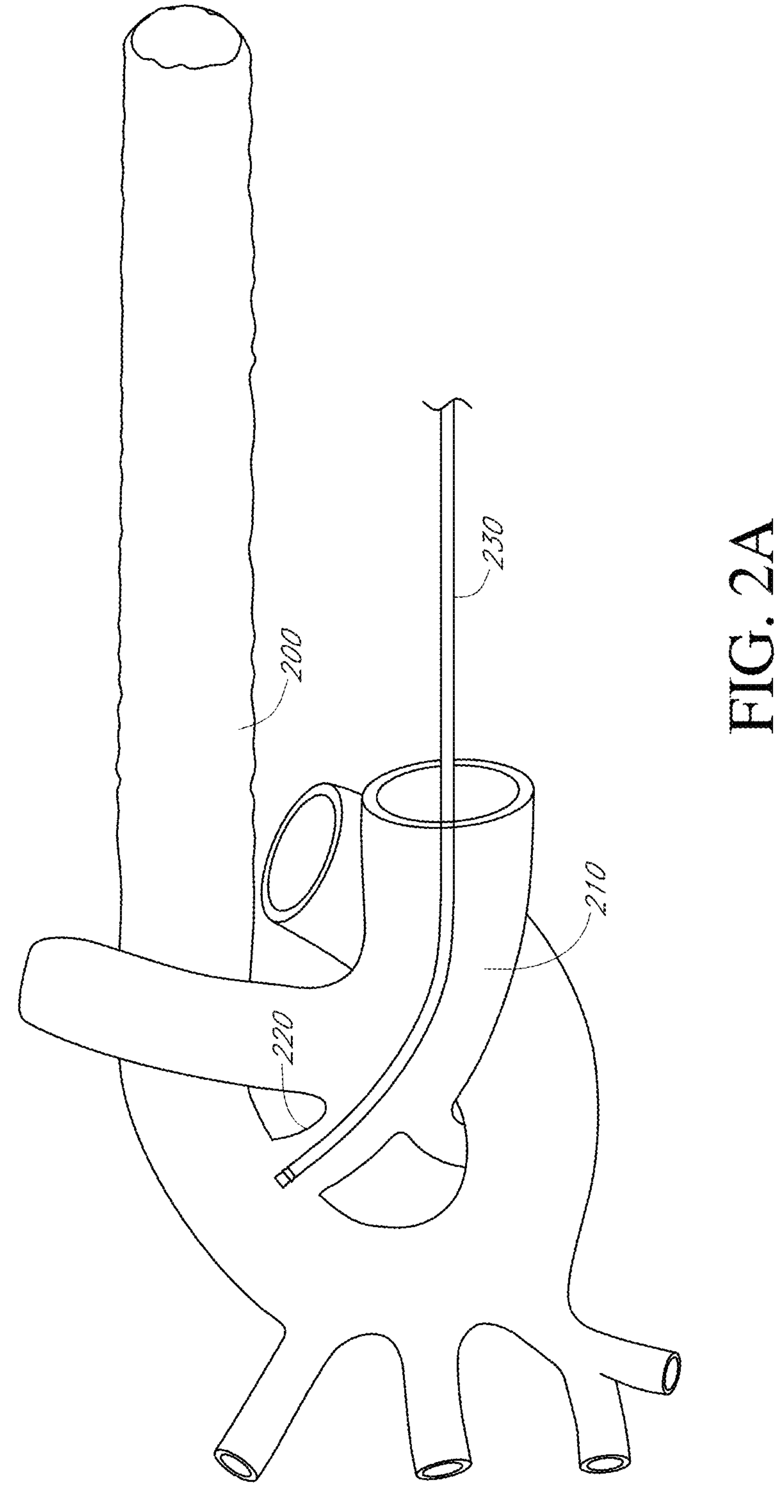
FIGS. 2A-2D show one embodiment of a method of maintaining a patent ductus arteriosus by approaching the ductus from the pulmonary artery.
Figure 2B:
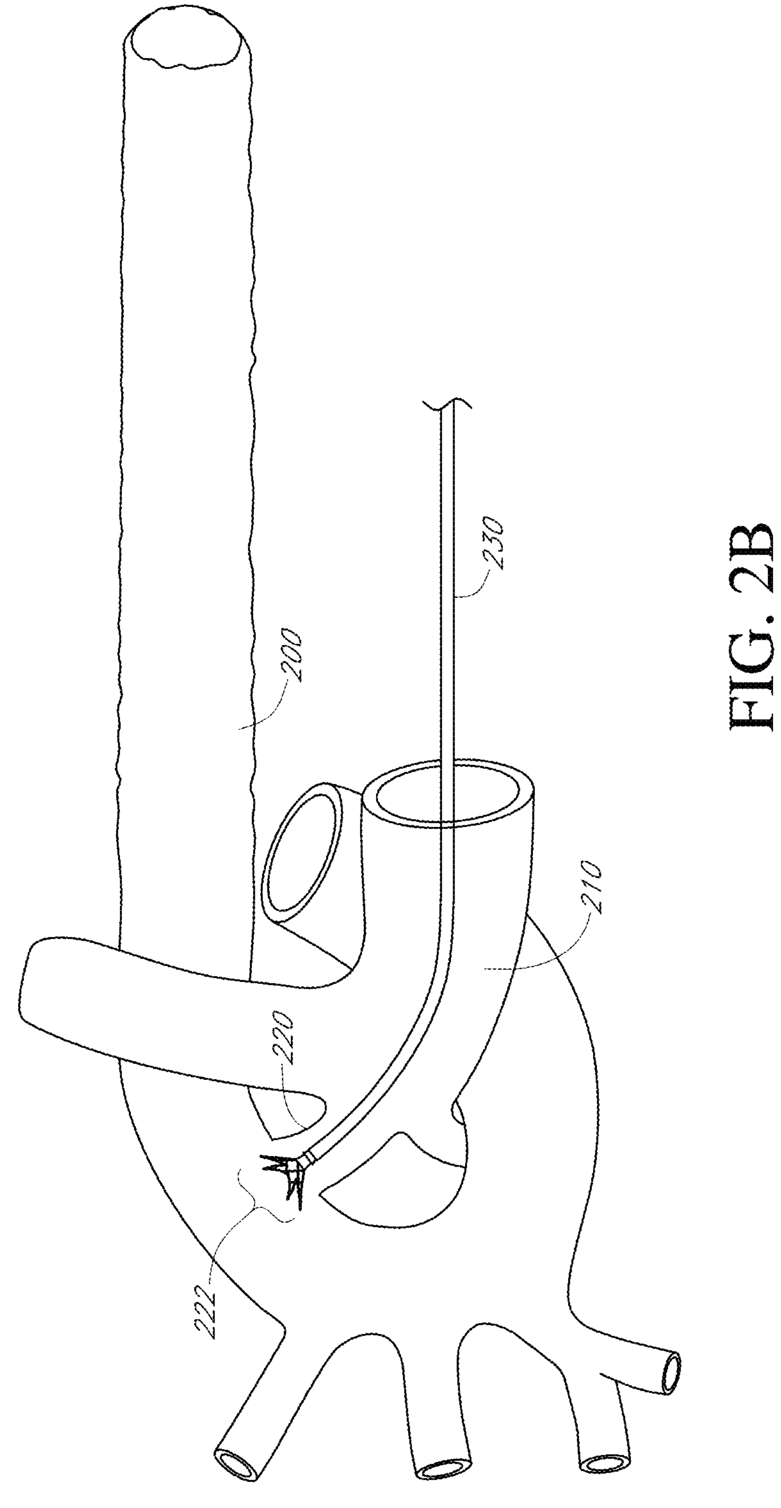
Figure 2C:
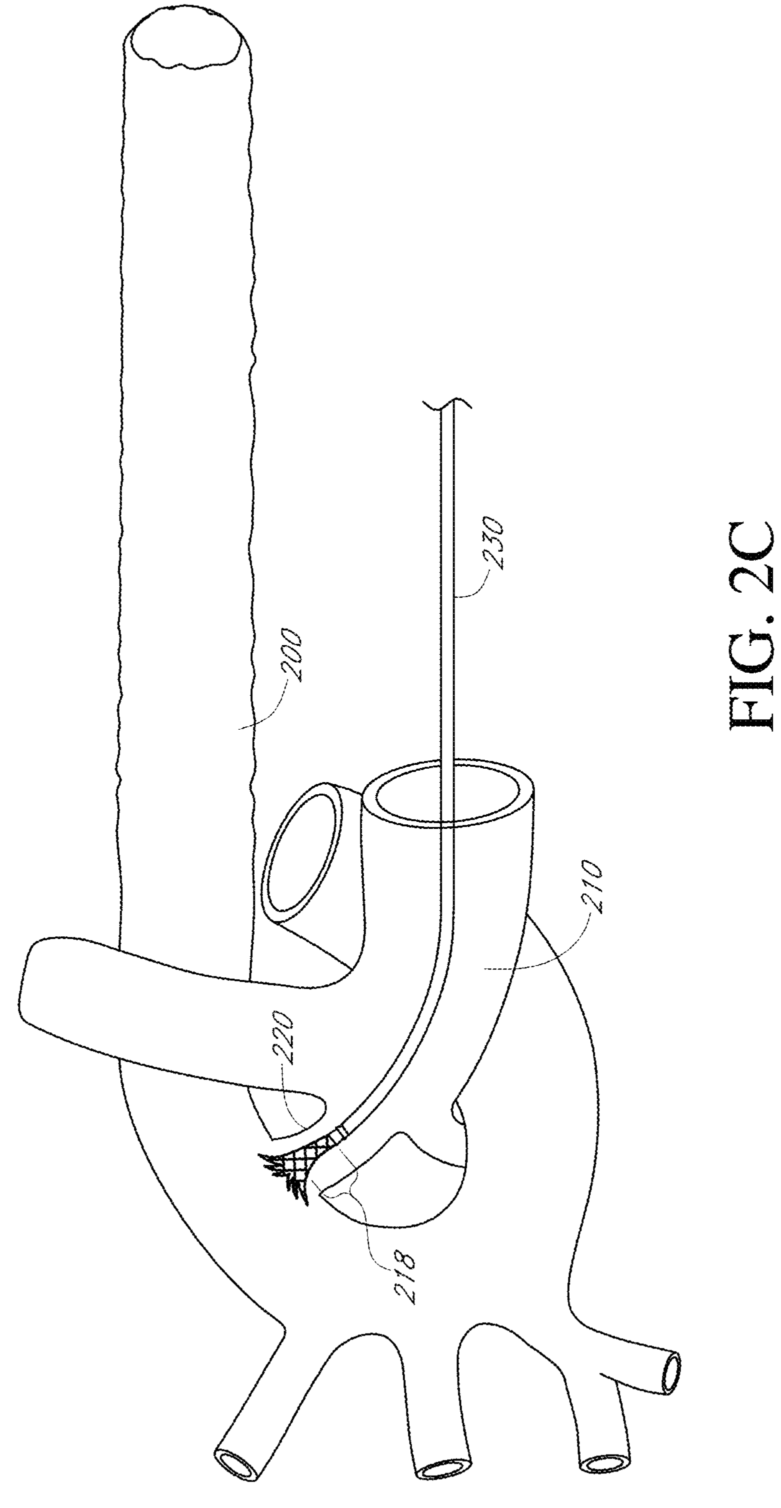
Figure 2D:
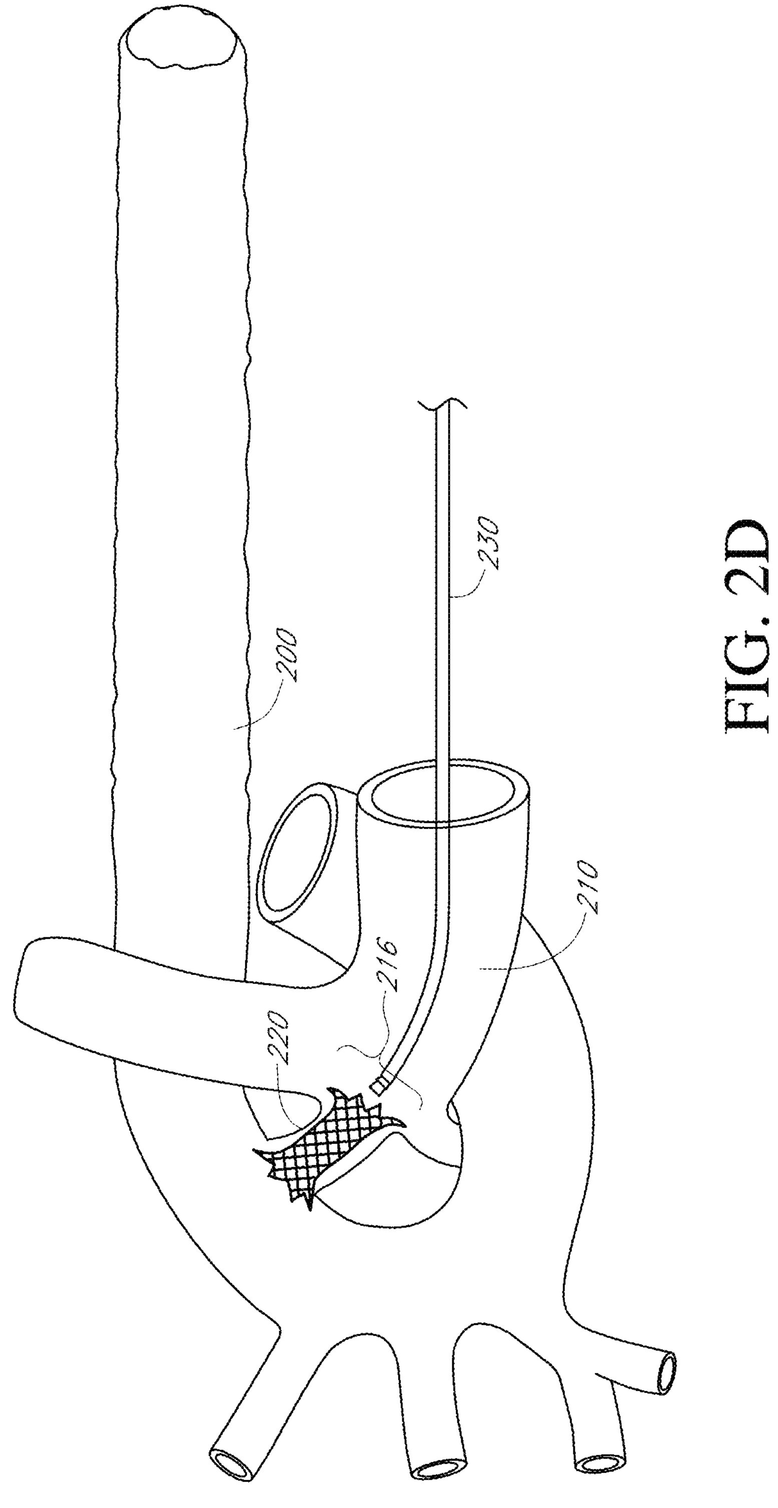

Further, FIGS. 2A-2D show one embodiment of a method of delivering any of the stents described herein to a ductus arteriosus from a pulmonary artery to an aorta. FIG. 2A illustrates an embodiment of a method of advancing a delivery system 230 through a pulmonary artery 210 and through a ductus arteriosus 220 to approach an aorta 200. As shown in FIG. 2B, the delivery system 230 releases a first, or distal, end section 222 that expands outwardly to the diameter or a fraction of the lumen of the ductus 220. In some embodiments, the diameter of the stent is undersized relative to the diameter of the lumen defined by the ductus, for example, because of prostaglandin therapy or a selected size of the stent, as described elsewhere herein. The first end section 222, which may comprise any of the features shown in 3A-4B, 7, 9-14, 17A-17B, 19-25D, 27A-27B of any of the stent embodiments described herein, at least partially anchors at the ductus lumen and at least partially circumferentially covers the ostium of the aorta 200. Constrained stent body 218 is released from the delivery system 230, as shown in FIG. 2C. In some embodiments, constrained rings are individually released from the distal end of the delivery system and expand until the entire length of the ductus 220 is covered, and a second, or proximal, flanged end is released and expands outward. The second flanged end 216, which may comprise any one or more of the features shown in FIGS. 3A-4B, 7, 9-14, 17A-17B, 19-25D, 27A-27B of any of the stent embodiments described herein, at least partially anchors at the lumen of the ductus 220 and at least partially circumferentially covers the ostium of the pulmonary artery 210, as shown in FIG. 2D. Advantageously, this method of delivering any of the stents described herein increases systemic circulation of the patient but may also be used to increase pulmonary circulation.

In some embodiments of FIG. 1A or 2A, a method of delivering any of the stents described elsewhere herein includes advancing a wire through the ductus; advancing an elongate body (e.g., microcatheter) over the wire and through the ductus; removing the wire from a lumen of the elongate body; and inserting a stent into the elongate body, for example using a transfer sheath. Further, with regard to FIGS. 1B and 2B, the method further includes advancing the stent through a lumen of the elongate body using, for example, any of the pusherwires disclosed herein; and deploying the stent, as shown in further detail in FIGS. 1C-1D and 2C-2D. In some embodiments, deploying may include deploying a distal end section of the stent first into a pulmonary artery (or alternatively an aorta), then pulling back on the elongate body (microcatheter) and pusherwire to add tension to the stent to anchor the stent at the ductus ostium. Deploying may further include continuing to pull back on the microcatheter to unsheathe and deploy the stent. For example, pulling back on both the microcatheter and pusherwire can adjust a length and/or flexibility of the stent.

FIGS. 25A-25D show stent deployment through a microcatheter 2700. A distal end section 2710 of the stent is advanced from the microcatheter 2700 (FIG. 25A); one or more end section struts and/or one or more end section rings 2710 progressively flare as the stent is advanced out of the microcatheter (FIGS. 25B-25C); and the stent continues to deploy as the stent is advanced to deploy the body section 2720 of the stent (FIG. 25D) and ultimately the proximal end section. In some embodiments, as the distal end section of the stent is deployed, the delivery system (e.g., the catheter 2700 relative to the pusherwire 2730) may be tensioned slightly to align the distal end section with the ostium. In some embodiments, as the body section 2720 of the stent is deployed, the delivery system (e.g., catheter) 2700 may be advanced or retracted to adjust a length of the stent as it is deployed. Further, a distal tip or distal end segment of the catheter may be aligned with an opposite ostium of the vessel or an opposite wall of the septum as the proximal end section of the stent is deployed. The general methods shown in FIGS. 25A-25D, as well as the methods shown in FIGS. 1A-1D and FIGS. 2A-2D, may be used with any of the stent embodiment described herein.

Any of the methods described herein may include optionally administering a prostaglandin to the patient to dilate the ductus arteriosus. Delivering a stent on prostaglandins significantly reduces the risk of vasospasm, a life-threatening situation for patients. While the ductus is enlarged, the delivery system is configured to constrain and deploy any of the stent embodiments described herein within the ductus arteriosus. In some embodiments, an outer diameter of the ductus arteriosus, when dilated with prostaglandins, ranges from between about 20% to about 50%; about 50% to about 100%; about 60% to about 120%; about 75% to about 140%; about 40% to about 140%; about 30% to about 100%; about 80% to about 120%; about 70% to about 110%; about 90% to about 150%; etc. larger than an outer diameter of any of the stents described herein, when in an expanded, deployed configuration.

Any one or more of the aforementioned steps may be performed with or without contrast. For example, contrast injections may be made between a sheath and a microcatheter; through an empty microcatheter; through one or more side holes in a sidewall of the microcatheter; through one or more holes in a hub of a pusherwire; and/or through a gear shaped hub on the pusherwire (i.e., the hub may comprise or define one or more cutouts or concave regions along its perimeter or on an external surface of the hub). This gear shape provides additional space for contrast to flow through. Various features of the delivery system will be described in further detail below.

Figure 26A:
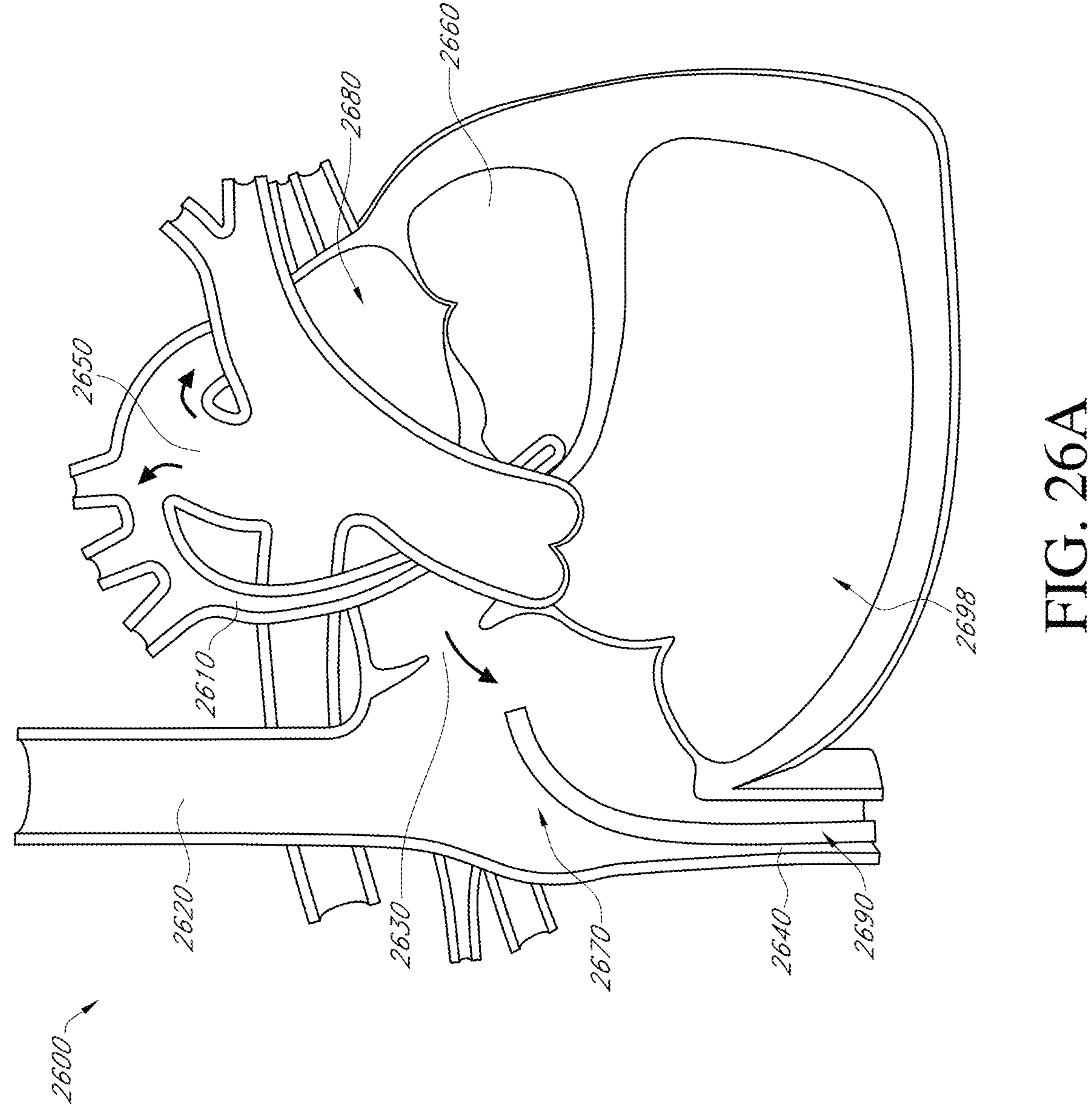
FIGS. 26A-26D show a method of deploying a stent in a septal conduit.
Figure 26B:
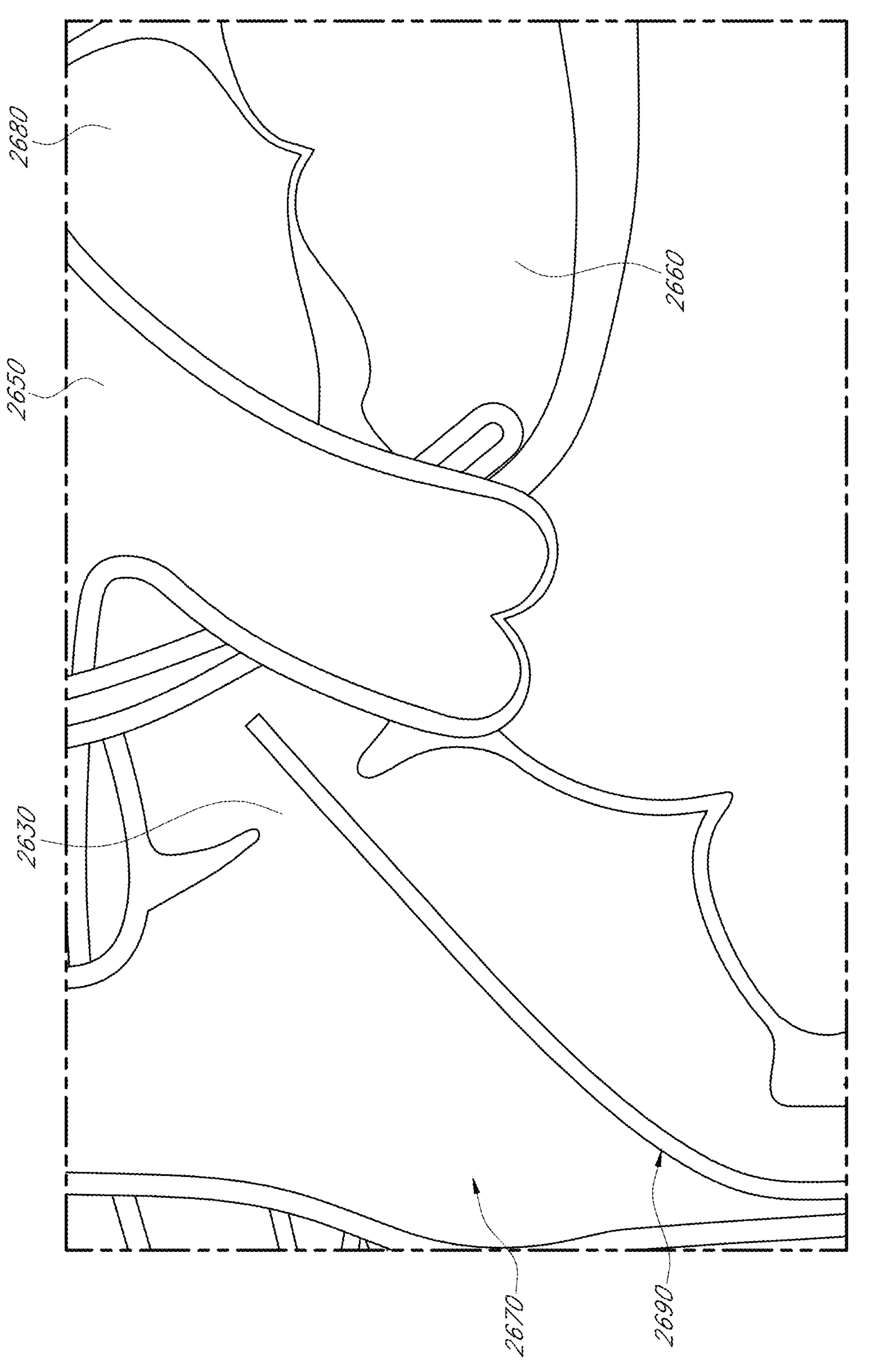
Figure 26C:
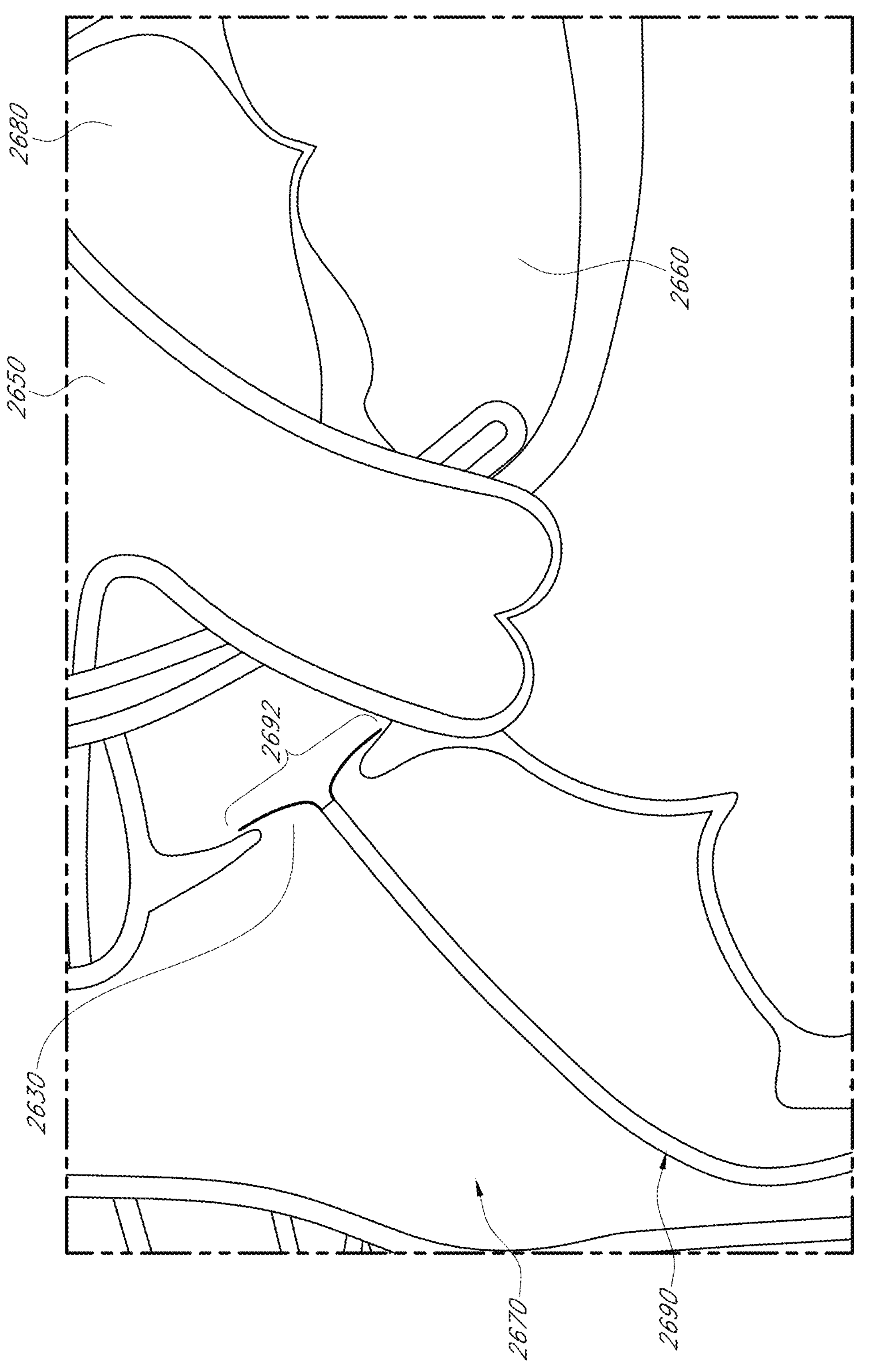
Figure 26D:
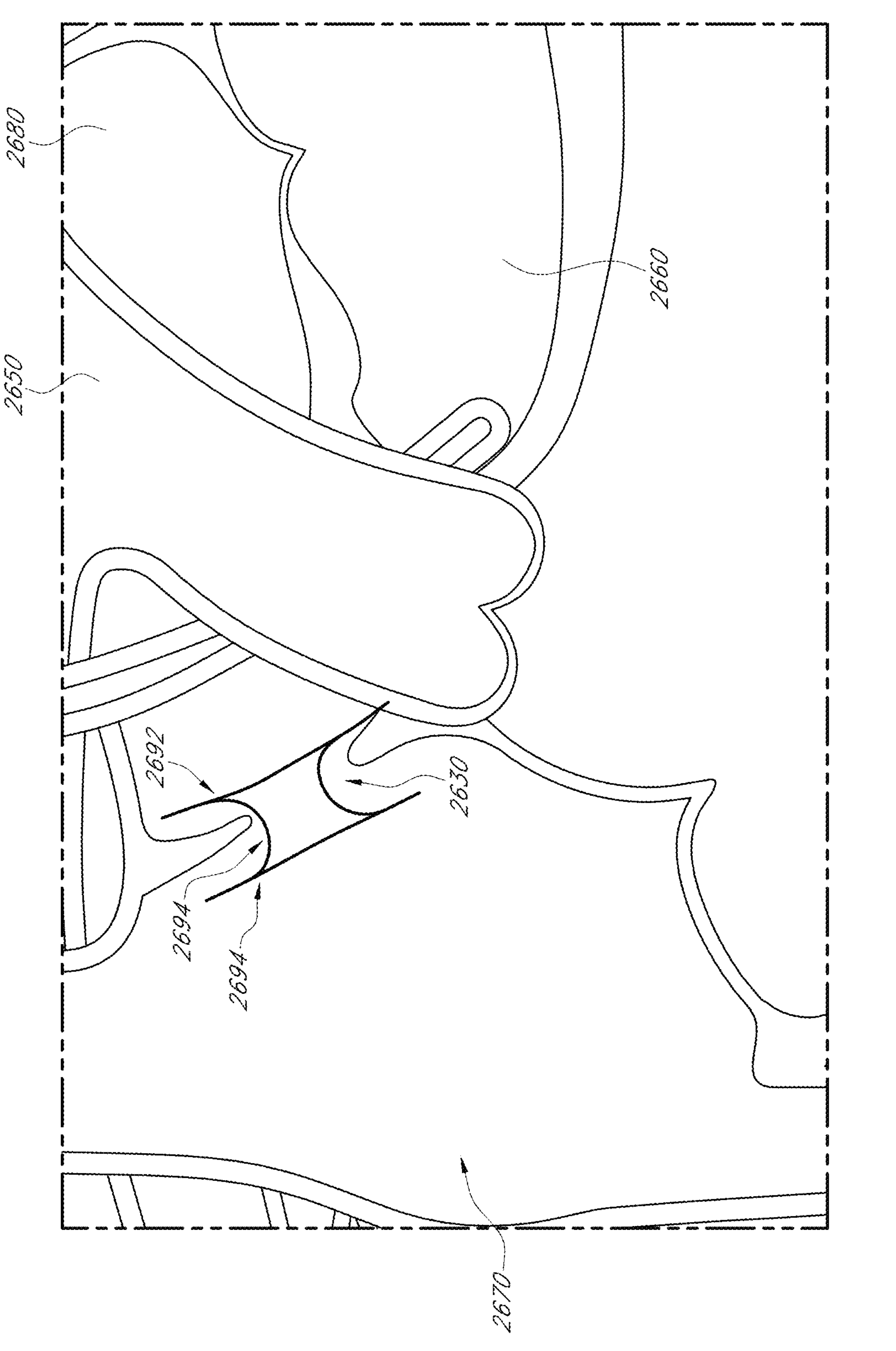

FIGS. 26A-26D show a method of deploying a stent in a septal conduit 2630. FIG. 26A shows an exemplary heart 2600 having a hypoplastic left ventricle. The heart 2600 includes aorta 2610, superior vena cava 2620, inferior vena cava 2640, septal defect 2630, ductus arteriosus 2650, left ventricle 2660, right ventricle 2698, right atrium 2670, and left atrium 2680. One embodiment of a method of treating a septal defect, as shown in FIGS. 26A-26D, includes advancing a stent delivery system 2690 into a right atrium 2670 of a patient, as shown in FIG. 26A. Advancing may include accessing the vasculature through a femoral vein or another access point (e.g., radial vein, carotid artery, etc.). Advancing may include advancing the stent delivery system 2690 through the inferior vena cava 2640 and into the right atrium 2670. As shown in FIG. 26B, the method includes advancing the stent delivery system 2690 across the septum. In some embodiments, advancing the stent delivery system 2690 across the septum includes crossing a foramen *ovale*, an atrial septal defect, or a septostomy. As shown in FIG. 26C, the method includes deploying, from the stent delivery system 2690, a distal end 2692 of the stent in a left atrium 2680. The step of FIG. 26C may further include loading a stent into a proximal end of the stent delivery system 2690 and advancing the stent through the stent delivery system 2690 until it approaches a distal end of the stent delivery system 2690. Additionally, or alternatively, the step of FIG. 26C includes applying tension or force towards a proximal end of the delivery system 2690 as the stent is being deployed to anchor the distal ends 2692 into a septal wall between the right atrium 2670 and left atrium 2680. As shown in FIG. 26D, the method includes advancing the body section 2694 of the stent out of the distal end of the stent delivery system 2690, across the septal wall, and deploying a proximal end 2696 of the stent in the right atrium 2670. The step shown in FIG. 26D may further include securing the stent in the septum. Any of the stent embodiments described herein may be used in combination with the method shown in FIGS. 26A-26D. For example, the body sections of any of the stents described herein may be elongated or shortened for application in treating of septal defects. Further, although the method of FIG. 26A-26D is shown in a patient having a hypoplastic left ventricle, one of skill in the art will appreciate that similar devices and associated methods may be used to treat any septal defect.

Devices

Each stent design described herein enables coverage of the most common ductus lengths from about 8 mm to about 28 mm and comes in stent diameters between about 3 mm and about 5 mm, for example, for ductal-dependent pulmonary circulation or about 5 mm to about 10 mm, for example, for ductal-dependent systemic circulation. Further, various stent designs described herein may be optimized for a septal conduit to enable coverage of the septal conduit. For example, a diameter of a septal device at a body section may be about 4 mm to about 5 mm and have a length less than about 8 mm.

The technical problem sought to be solved by the stent designs described herein was how to create a stent that crimped down to a diameter that was sufficiently small and flexible so that it could be delivered through a microcatheter while also creating a stent that had sufficient radial force to maintain patency of a conduit or lumen. It is difficult to achieve sufficient radial force with stents that crimp down to a small diameter with sufficient flexibility because there is limited space for metal in the stent structure. The amount of metal that is available for the stent is determined by the crimp diameter. As such, the strut lengths, widths, and thickness; the number of struts per ring (divided by 2 is crown number per ring); and the number of bridges between adjacent rings, described herein, are critical in achieving this crimp down diameter but sufficient flexibility and radial force upon expansion. For example, a ratio of crown number to bridge number of the body section is critical for achieving sufficient flexibility in tortuous vasculature while also maintaining sufficient radial force, which is needed to maintain a patent vessel or conduit that is actively trying to close. In some embodiments, a crown number to bridge number ratio of a body section, for the stent embodiments described herein, may be about 6:2 to about 12:8 or about 6:3 to about 9:3. Further for example, the number of crowns may be about 6 crowns to about 12 crowns, such that the number of struts per rings is about 12 struts to about 24 struts and the number of bridges is about three to about nine. As such, there is a tight balance between radial force with flexibility and deliverability.

Table 1 below shows a qualitative scoring of stent flexibility and deliverability based on varying strut, crown, and bridge numbers. All struts across all tested embodiments had the same strut thickness and similar angles between adjacent struts in each ring. Strut lengths in each embodiment were slightly varied to accommodate the varying crown and/or bridge numbers. The strut width, thickness, and length are described with respect to FIGS. 3A-3E. The data shown in Table 1 suggest that a crown to bridge ratio of about 6:3 to about 9:3 may be critical for achieving a sufficient crimp down diameter and flexibility for delivery via a microcatheter but sufficient radial force for maintaining a patent ductus arteriosus or septal conduit.

TABLE 1

Qualitative Stent Flexibility Data

| Strut No. | Crown No. | Bridge No. | Flexibility Assessment |
|---|---|---|---|
| 16 | 8 | 2 | Extremely flexible, buckling, no pushability |
| 16 | 8 | 3 | Somewhat flexible |
| 16 | 8 | 4 | Inflexible |
| 16-12 | 8-12 | 4 | Very flexible |
| 16 | 8 | 8 | Inflexible |
| 18 | 9 | 2 | Extremely flexible, buckling, no pushability |
| 18 | 9 | 3 | Acceptable flexibility |
| 18 | 9 | 4 | Somewhat flexible |
| 12-18 | 6-9 | 3 | Somewhat flexible |
| 12 | 6 | 3 | Some inflexibility |
| 12 | 6 | 6 | Inflexible |

To add to the qualitative flexibility assessment in Table 1 with a measure of structural strength, a crush test was performed, as a surrogate for radial resistive strength. Literature data suggest that stent crush test correlates well with stent radial resistive force, at least for a majority of stents (Brandt-Wunderlich, C. et al. "Support function of self-expanding nitinol stents—Are radial resistive force and crush resistance comparable?" *Current Directions in Biomedical Engineering* 2019; 5 (1): 465-468, the contents of which are herein incorporated by reference in their entirety). The stents were crushed by 50% (a body section of each stent had a 4 mm resting diameter and was crushed by 2 mm) between parallel plates, each stent positioned there between, in a linear fixture (Baoshishan® Force Test Stand Hand Wheel-Operated Push Pull Test Stand Tensile and Compression Load Tester with Digital Displacement Scale and HJJ-001 Clamp x2) using an HF-5 Digital Push Pull Gauge Force Gauge HF-5N. The results are shown in FIG. 38.

Figure 38:
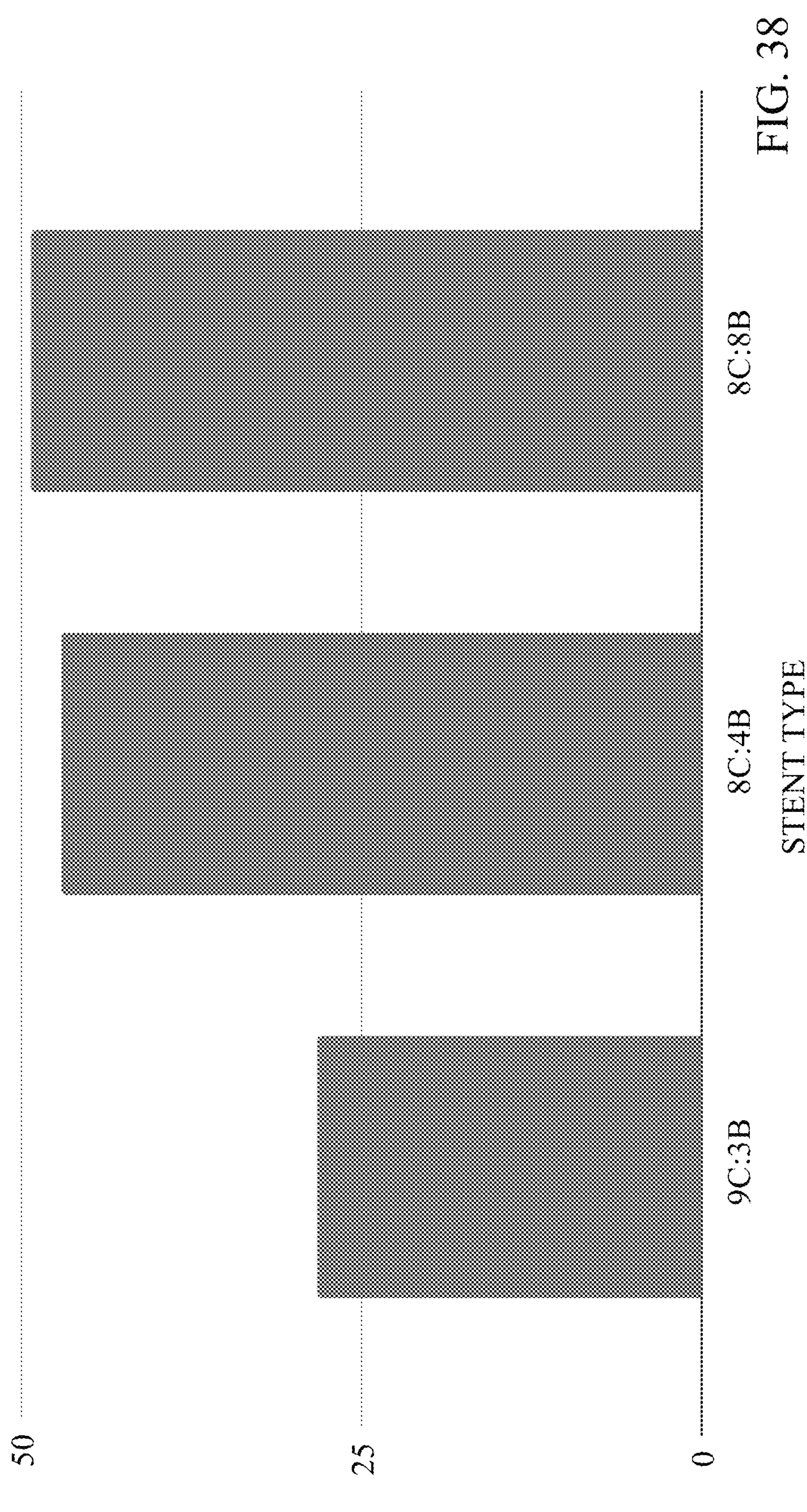
FIG. 38 shows crush test data for various stent designs described herein.

As shown in FIG. 38, a stent having a ratio of 8 crowns to 8 bridges had the highest strength (e.g., nearly 50 g), while reducing the bridge count to a ratio of 8 crowns to 4 bridges slightly reduced the strength (e.g., to about 45 g). A stent having a ratio of 9 crowns to 3 bridges displayed still further reduced strength but still significant strength at about 29 g. However, although the 8 crown: 8 bridge and 8 crown: 4 bridge designs displayed significant strength, they were each inflexible (see Table 1), making them difficult to delivery and/or position. In contrast, while the 9 crown: 3 bridge design had reduced strength, it had increased flexibility, so a balance between strength and flexibility improved the deliverability and positioning while maintaining sufficient radial strength to maintain a conduit in a patent state.

FIGS. 3A-3E show one embodiment of a stent for treatment of a congenital heart defect. The stent shown in FIGS. 3A-3E provides a technical solution for the above-mentioned technical problems, as shown in the various stent design features described below and elsewhere herein.

Figure 3A:
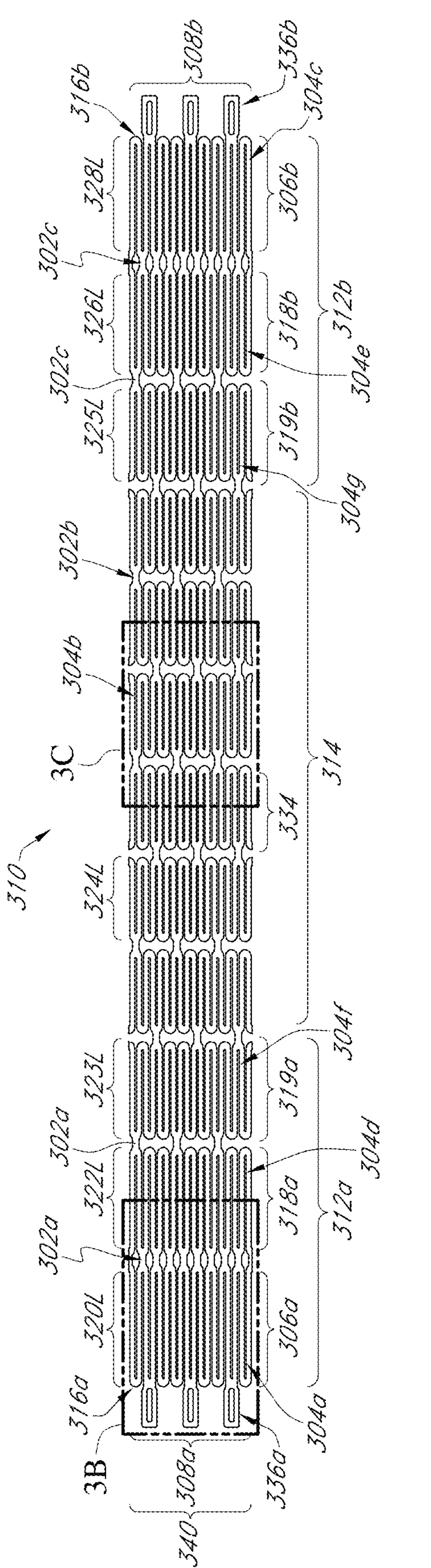
FIG. 3A shows one embodiment of an example stent in a two-dimensional (2D) crimped configuration configured to maintain a patent lumen or conduit (once expanded in vivo).

FIG. 3A shows one embodiment of a stent 310 in a 2D crimped configuration. As shown, the stent 310 has a first end section 312*a* defining a proximal face 308*a*, a second end section 312*b* defining distal face 308*b*, and a body section 314 between the first end section 312*a* and the second end section 312*b*.

Figure 3C:
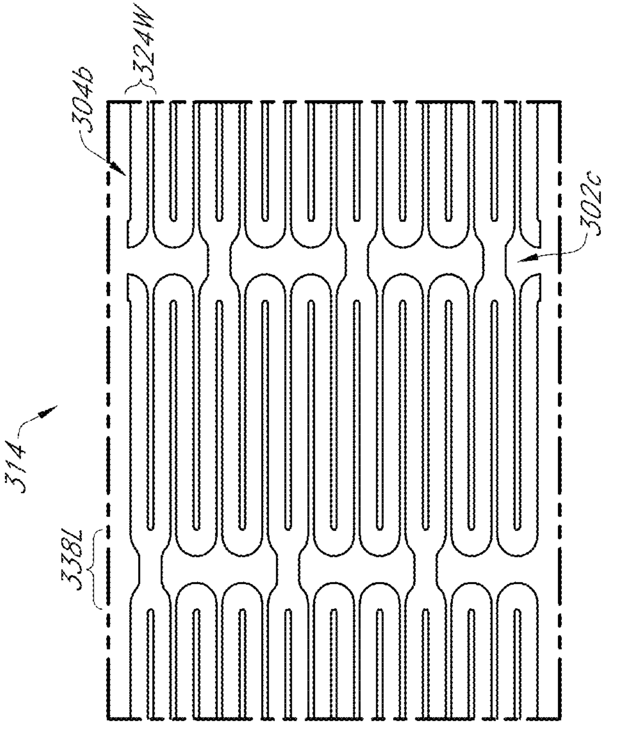
FIG. 3C shows a zoomed-in 2D view of the body section of the stent of FIG. 3A.
Figure 3C:
Figure 3B:
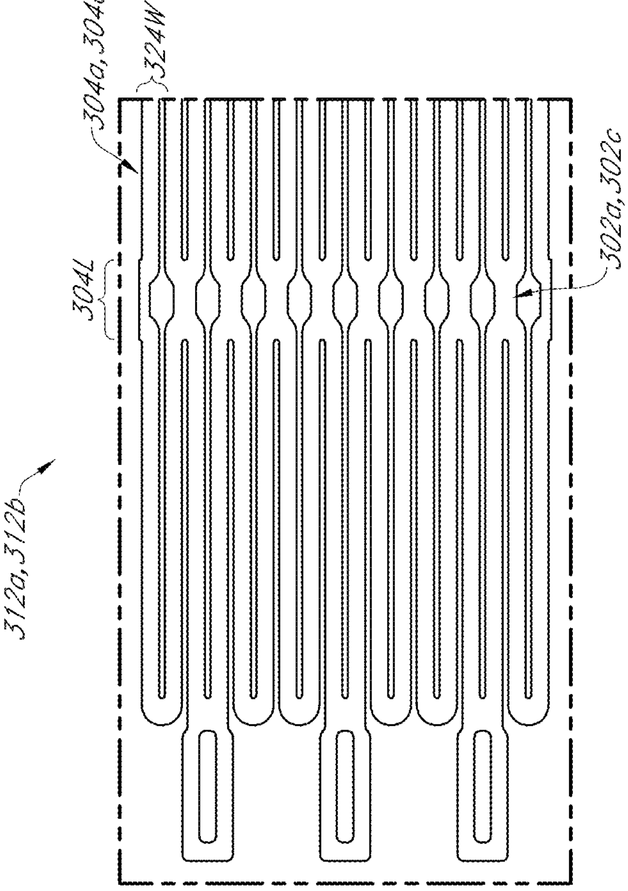
FIG. 3B shows a zoomed-in 2D view of the first end section of FIG. 3A.
Figure 3D:
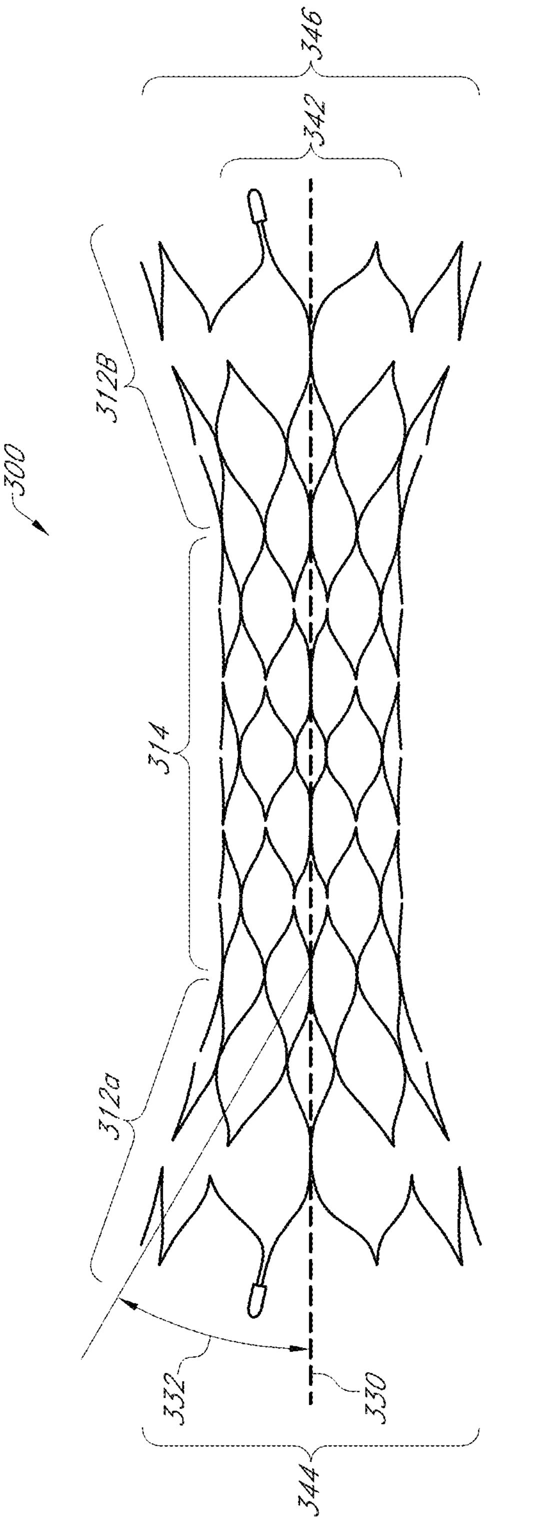
FIG. 3D shows the stent of FIG. 3A in an expanded configuration.

The first end section 312*a* comprises one ring, more than one ring, or a plurality of rings. As shown in this embodiment, first end section 312*a* comprises a terminal ring 306*a* comprising a plurality of struts 304*a*, each having a length 320L; a penultimate ring 318*a* comprising a plurality of struts 304*d*, each having a length 322L; and an antepenultimate ring 319*a* comprising a plurality of struts 304*f*, each having a length 323L. Length 320L of each strut 304*a* may be substantially similar to length 322L of each strut 304*d* and/or length 323L of each strut 304*f*. Preferably, length 320L is greater than length 322L which is greater than length 323L, such that the lengths of the struts increase moving from the body section 314 to the first end section 312*a* to the proximal face 308*a*. In other embodiments, length 323L is greater than length 322L which is greater than length 320L, such that the lengths of the struts decrease moving from the body section 314 to the first end section 312*a* to the proximal face 308*a*. In a further iteration, length 322L and 323L may be substantially the same or 320L and 322L may be substantially the same or length 320L and 323L may be substantially the same. Strut lengths 320L, 322L, and 323L may each be between about 2.5 mm and about 4.5 mm. Preferably, a length 320L of each strut 304*a* is about 1.9 mm to about 2.3 mm; a length 322L of each strut 304*d* is about 1.6 mm to about 2.0 mm; and a length 323L of each strut 304*f* is about 1.3 mm to about 1.7 mm. As shown in FIG. 3D, proximal face 308*a* (shown in FIG. 3A) of the first end section 312*a* has a diameter 344 (measured at the terminal crowns 316*a* of the terminal ring 306*a*) that is about 110% to 180%; about 120% to about 170%; about 130% to about 160%; for example about 150%; about 155%; or about 160% larger than a diameter 342 of the body section 314. Proximal face 308*a* includes one, one or more, or a plurality of radiopaque markers 336*a*. Alternatively, radiopaque markers 336*a* may be replaced with a connecting element, such as a male or female connector that is configured to connect with a complementary feature (e.g., a female or male connector, respectively) on a delivery system. Rings 306*a* and 318*a* and rings 318*a* and 319*a* are connected to each other via one or more or a plurality of bridges 302*a*. As shown in FIG. 3B, each bridge 302*a* has a length 304L of about 0.1 mm and about 0.25 mm. There may be about three bridges to about nine bridges.

The second end section 312*b* comprises one ring, more than one ring, or a plurality of rings. As shown in this embodiment, second end section 312*b* comprises a terminal ring 306*b* comprising a plurality of struts 304*c*, each having length 328L; a penultimate ring 318*b* comprising a plurality of struts 304*c*, each having a length 326L; and an antepenultimate ring 319*b* comprising a plurality of struts 304*g*, each having a length 325L. Length 328L of each strut 304*c* may be substantially similar to length 326L of each strut 304*e* and/or length 325L of each strut 304*g*. Preferably, length 328L is greater than length 326L, which is greater than length 325L of each strut 304*g*, such that the lengths of the struts increase moving from the body section 314 to the second end section 312*b* to the distal face 308*b*. In other embodiments, length 325L is greater than length 326L, which is greater than length 328L, such that the lengths of the struts decrease moving from the body section 314 to the second end section 312*b* to the distal face 308*b*. In a further variation, length 328L and 326L may be substantially the same or 328L and 325L may be substantially the same or length 326L and 325L may be substantially the same. Strut lengths 326L, 328L, and 325L may each be between about 2.5 mm and about 4.5 mm. Preferably, a length 328L of each strut 304*c* is about 1.9 mm to about 2.3 mm; a length 326L of each strut 304*c* is about 1.6 mm to about 2.0 mm; and a length 325L of each strut 304*g* is about 1.3 mm to about 1.7 mm. As shown in FIG. 3D, distal face 308*b* (shown in FIG. 3A) of the second end section 312*b* has a diameter 346 (measured at the terminal crowns 316*b* of the terminal ring 306*b*) that is about 110% to 180%; about 120% to about 170%; about 130% to about 160%; for example about 150%; about 155%; or about 160% larger than a diameter 342 of the body section 314. Distal face 308*b* includes one, one or more, or a plurality of radiopaque markers 336*b*. Alternatively, radiopaque markers 336*b* may be replaced with a connecting element, such as a male or female connector that is configured to connect with a complementary feature (e.g., a female or male connector, respectively) on a delivery system. Rings 306*b* and 318*b* and rings 318*b* and 319*b* are connected to each other via one or more or a plurality of bridges 302*c*. As shown in FIG. 3B, each bridge 302*c* has a length 304L of about 0.1 mm to about 0.25 mm. There may be about three bridges to about nine bridges between each pair of adjacent rings.

Body section 314 comprises a plurality of rings 334, each comprising a plurality of struts 304*b*. Body section 314 may comprise one ring or one or more rings (e.g., in a septal defect embodiment) or more than one ring or a plurality of rings (e.g., in a patent ductus arteriosus embodiment). For example, there may be about one ring, about 2 to about 6 rings, or about 3 to about 10 rings. The plurality of struts 304*b* of the body section 314 each have a length 324L. As shown in FIG. 3A but also for any of the stent embodiments described herein, the length 324L of each of the struts 304*b* may be about 0.6 mm to about 1.6 mm, preferably about 0.8 mm to about 1.4 mm. The rings 334 of the body section 314 may be connected via a plurality of bridges 302*b*, for example about three bridges to about nine bridges between each pair of adjacent rings. As shown in FIGS. 3B-3C, but also for any of the stent embodiments described herein, each bridge 302*a*, 302*c* and 302*b* has a length 304L, 338L, respectively, of about 0.1 mm to about 0.25 mm.

As shown in FIGS. 3B-3C, but also for any of the stent embodiments described herein, struts 304*a*, 304*b*, 304*c* may each have a width 324W of about 0.08 mm to about 0.1 mm.

As shown in FIGS. 3B-3C, but also for any of the stent embodiments described herein, struts 304*a*, 304*b*, 304*c* may each have a thickness of about 0.09 mm to about 1.1 mm.

Struts 304*a*, 304*c* in the first end section 312 and the second end section 312*b*, respectively, are longer than the struts 304*b* in the body section 314 to accommodate greater expansion while maintaining a substantially constant or similar angle between adjacent struts in each ring. For example, as shown in FIG. 3D, angle 332, relative to a longitudinal axis 330 of strut 304*a*, is about 50 degrees to about 70 degrees or about 60 degrees to about 70 degrees, preferably about 65 degrees.

In some embodiments, the stents described herein have an open-cell design, such that a distance between adjacent rings in the first section, body section, and/or second section is about 0.1 mm to about 0.2 mm or about 0.12 mm to about 0.16 mm.

As shown in FIG. 3A, the diameter 340 of the stent 310 in a crimped configuration may be about 0.5 mm to about 0.75 mm, preferably about 0.60 mm to about 0.70 mm. FIG. 3D shows the stent of FIG. 3A in an expanded configuration, for example after deployment from a microcatheter. A diameter 342 of the body section 314 of the expanded stent 300 is about 3 mm to about 10 mm, about 3 mm to about 4.5 mm, about 5 mm to about 9 mm, about 6 mm to about 10 mm, etc., depending on the diameter of the target lumen. For example, at least a portion of a diameter of the lumen defined by the ductus arteriosus is about 4 mm to about 8 mm and an outer diameter of the body section of the stent is about 3 mm to about 4.5 mm. Further for example, at least a portion of the diameter of the lumen defined by the ductus arteriosus is about 5 mm to about 10 mm and an outer diameter of the body section of the stent is about 5 mm to about 9 mm. In still further examples, at least a portion of a diameter of the lumen defined by the ductus is about 5 mm to about 9 mm and an outer diameter of the body section of the stent is about 6 mm to about 10 mm.

In the expanded configuration, stent 300 has a radial resistive force (based on ISO 25539 standards), at about 1 mm of compression, of greater than about 0.20 N/mm, between about 0.20 N/mm to about 0.35 N/mm, between about 0.25 N/mm to about 0.31 N/mm, between about 0.25 N/mm to about 0.27 N/mm, or between about 0.30 N/mm to about 0.31 N/mm. For example, when the stent is compressed from a diameter of about 4 mm to about 3 mm, the radial resistive force is about 0.25 N/mm to about 0.27 N/mm. In another example, when the stent is compressed from a diameter of about 4 mm to about 2 mm, the radial resistive force is about 0.30 N/m to about 0.31 N/mm.

In some embodiments, the stent shown in FIGS. 3A-3E is configured to be anchored in a vessel that has a diameter that is about 20% to about 140%, about 40% to about 140%, about 20% to about 100%, etc. larger than the diameter of the body section of the stent.

Further, as shown in FIGS. 3A-3D, the stent 300 comprises an open cell design such that stent 300 does not kink at a radius of curvature of greater than or equal to about 4 mm or at a radius of curvature of greater than or equal to about 2 mm. For example, stent 300 may kink at a radius of curvature of less than or equal to about 2 mm.

Figure 3E:
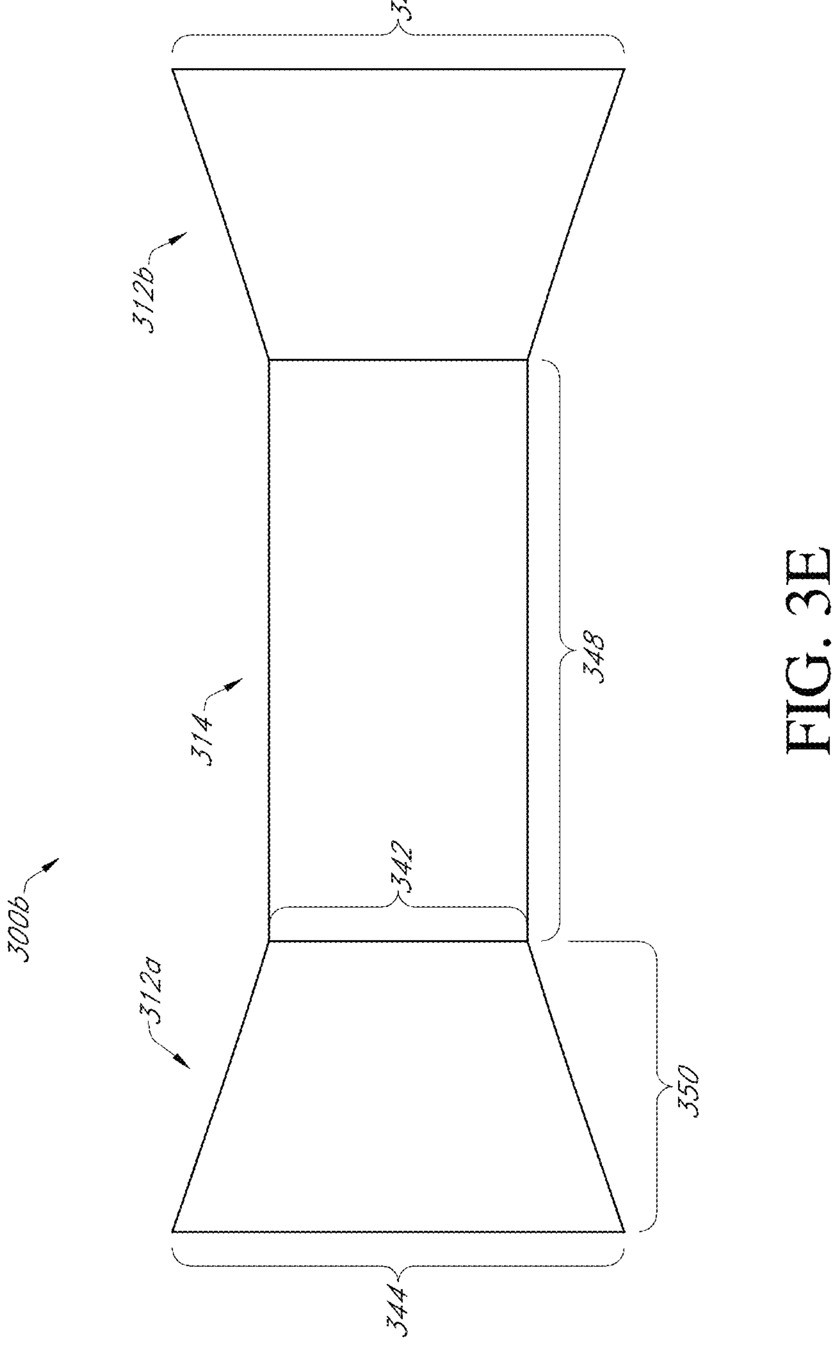
FIG. 3E is a schematic of the stent of FIG. 3D.

FIG. 3E shows one example of various parameters of the stent 300*b*, at least for a particular vessel having particular dimensions. One of skill in the art will appreciate that the dimensions will need to be scaled up or down depending on the size of the target vessel. Stent 300*b* in an expanded configuration has a body section 314 having a length 348 of about 6 mm to about 12 mm, preferably about 8 mm to about 10 mm, depending on a length specification. Stent 300*b* has a first end section 312*a* and a second end section 312*b*, each having a length 350 of about 3 mm to about 6 mm, preferably between about 4 mm to about 5 mm. A diameter 342 of the body section 314 is about 3 mm to about 6 mm, preferably about 3.5 mm to about 4.5 mm, depending on target vessel specification. A diameter 344 of the proximal face or a diameter 436 of the distal face is about 6 mm to about 8 mm, preferably about 6.5 mm to about 7.5 mm, depending on target vessel specifications.

FIGS. 4A-4B shows another embodiment of a stent 400 comprising a proximal face 410 at the first end section 402 that anchors the stent 400 at the proximal end and a distal face 420 at the second end section 406 that anchors the stent 400 at the distal end, thus ensuring end-to-end coverage of the ductus, regardless of stent length. The first and second end sections 402, 406 can be configured to slightly compress the ductus such that the entire ductus is covered by the stent. Further, as shown in FIG. 4B, an anchoring mechanism of stent 400 comprises adjacent terminal struts 426 joined at terminal crowns 424 at the proximal and/or distal faces. The adjacent terminal struts 426 joined at the terminal crowns 424 are at an angle 425 of about 75 degrees to about 110 degrees, relative to a longitudinal axis 422 of the stent 400.

Figure 7:
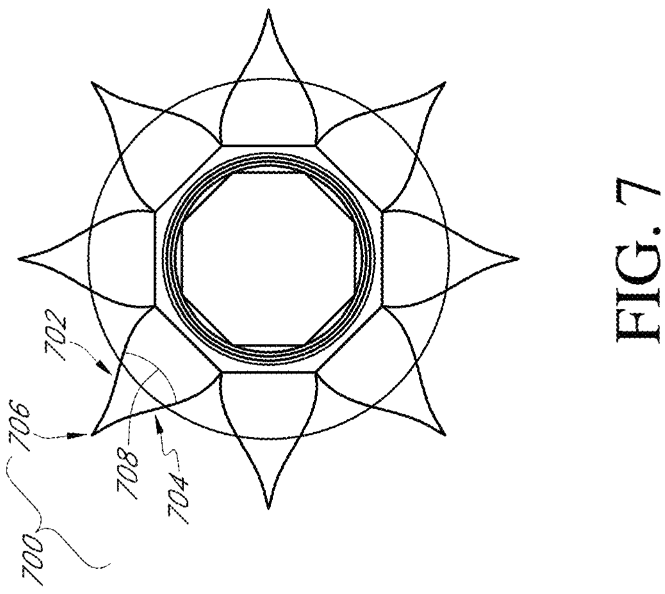
FIG. 7 shows another embodiment of a distal end of a stent for maintaining a patent lumen or conduit.
Figure 9:
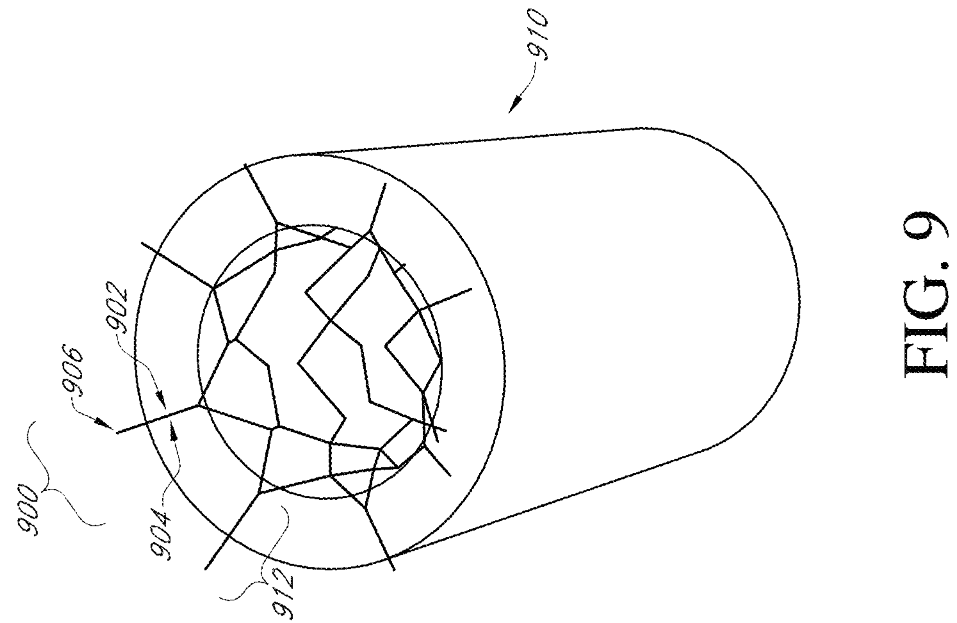
FIG. 9 shows a perspective view of an end section of an example stent anchored in a test lumen and configured to maintain a patent lumen or conduit.

Turning now to FIGS. 7 and 9, which show various embodiments of a stent having a first end section and/or second end section that defines a proximal face or distal face, respectively, comprising adjacent terminal struts joined at terminal crowns that are angled relative to a longitudinal axis of the stent body. The adjacent terminal struts joined at the terminal crowns may take on many different shapes and configurations as shown in FIGS. 4A-4B, 7, 9, 11A, and 19-24.

FIG. 7 shows a petal-like end section or flange forming a proximal or distal face of a stent. For example, petal-like flange 700 may include a first angled strut 702 and a second angled strut 704 joined at crown 706. Angle 708 between adjacent struts 702, 704 may be about 15 degrees to about 50 degrees, giving the flange a petal like appearance and an open cell structure to the flange. The terminal struts 702, 704 joined at terminal crown 706 may be angled relative to a longitudinal axis of the body section of the stent. For example, the angle may be about 50 degrees to about 115 degrees, as shown and described elsewhere herein. In contrast to flange 700 shown in FIG. 7, the stent shown in FIG. 9 comprises one or more stellate flanges 900 on a distal and/or proximal end to facilitate anchoring in a test lumen 910. Strut 904 is joined to adjacent strut 902 along at least a portion of struts 902, 904 and at crown 906 such that an angle in terminal region 912 between adjacent struts 904, 902 is less than about 5 degrees.

Figure 10:
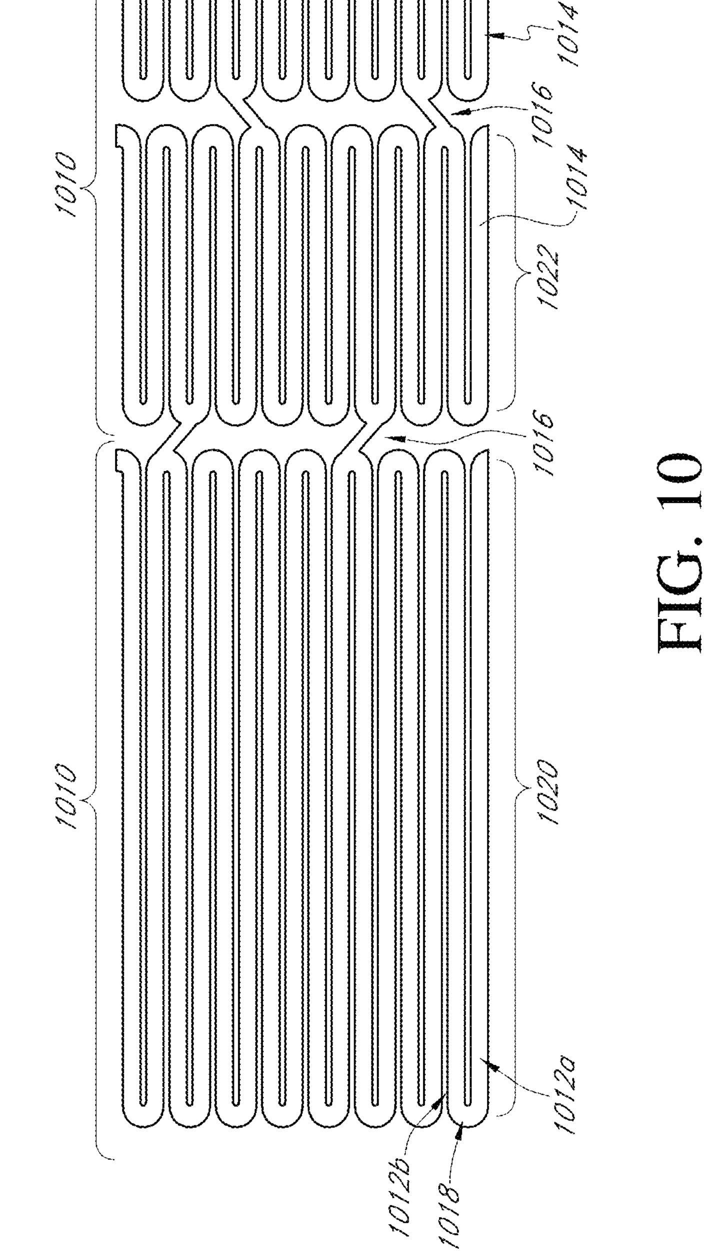
FIG. 10 shows another embodiment of an end section of a stent in a 2D crimped configuration.

Turning now to FIG. 10, which shows a zoomed-in, 2D view of a portion of a stent 1000 in accordance with one embodiment. Section 1010 can either be a first end section or a second end section and comprises a plurality of terminal struts 1012*a*, 1012*b*, . . . 1012*n* forming a terminal ring. Adjacent terminal struts 1012*a*, 1012*b* are joined at terminal crown 1018. Body section 1010 also comprises a plurality of struts 1014 arranged in a plurality of rings. Terminal struts 1012*a*, 1012*b* have a length 1020 that is longer than a length 1022 of a strut 1014 in the body section 1010. For example, the length 1020 of strut 1012*a* or 1012*b* may be 2× to about 4× greater than the length 1022 of strut 1014. For example, a length 1020 of strut 1012*a* or 1012*b* may be about 2 mm to about 6 mm while a length 1022 of strut 1014 may be about 0.5 mm to about 2 mm. Adjacent rings may be connected by bridges 1016. For example, the bridges may be angled relative to a longitudinal axis of the stent, at least in a compressed configuration.

Figure 11A:
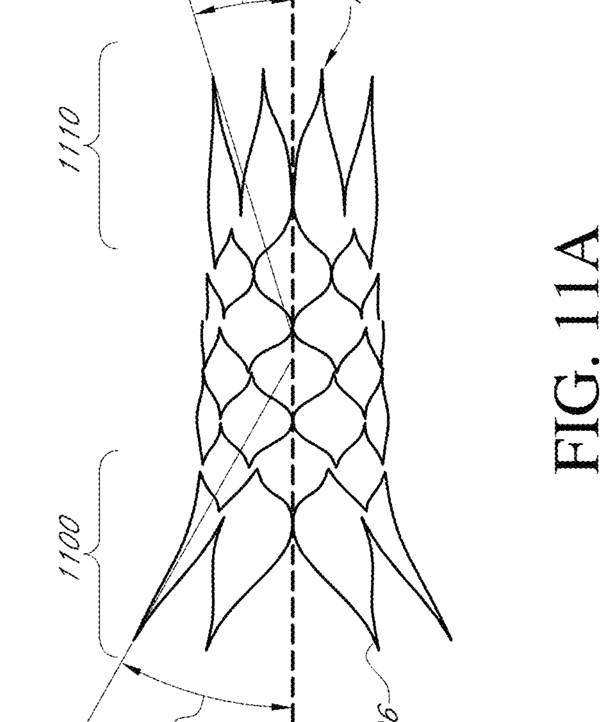
FIG. 11A shows one embodiment of a stent configured to be anchored mid-lumen in a bodily lumen or conduit.
Figure 11C:
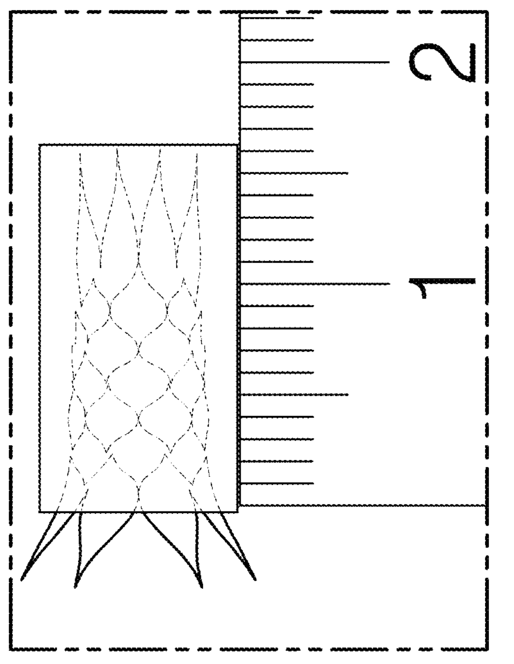
FIGS. 11B-11C show various degrees of deployment or stretching of the stent of FIG. 11A.
Figure 11B:
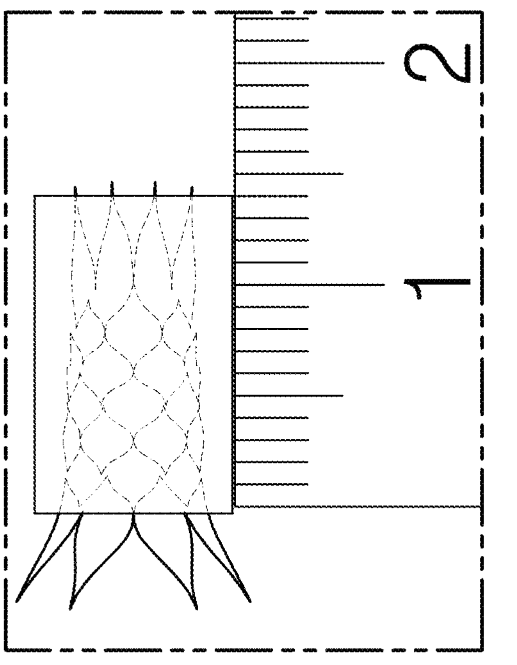
Figures 22, 23, 24:
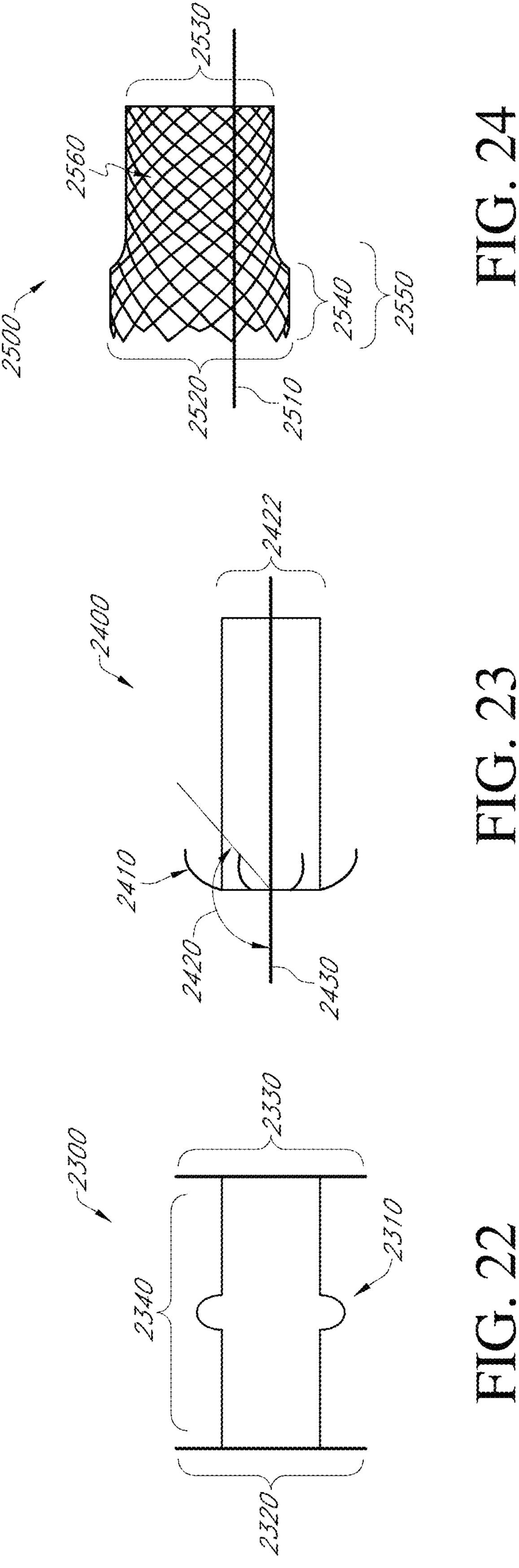
FIG. 22 shows another embodiment of a stent having an expanded bulged body section for anchoring the stent within a lumen or conduit.
FIG. 23 shows another embodiment of a stent having a flared or flanged end section for anchoring the stent within a lumen or conduit.
FIG. 24 shows another embodiment of an end section of a stent for maintaining a patent lumen or conduit.
Figure 25A:
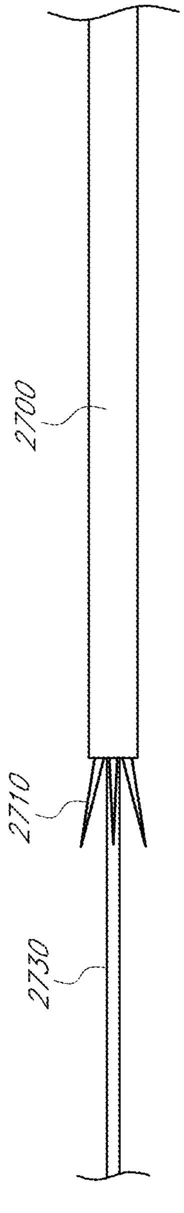
FIGS. 25A-25D show a method of stent deployment through a microcatheter.
Figure 25A:
Figure 25B:
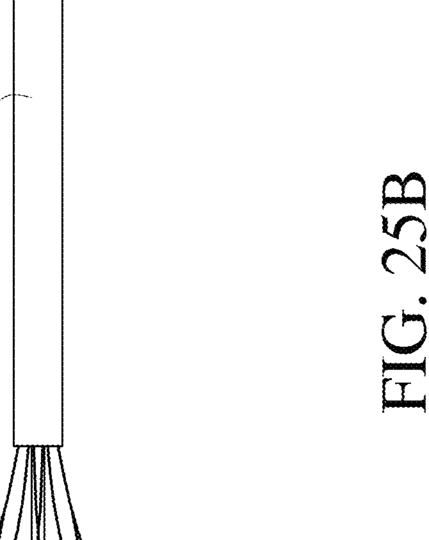
Figure 25C:
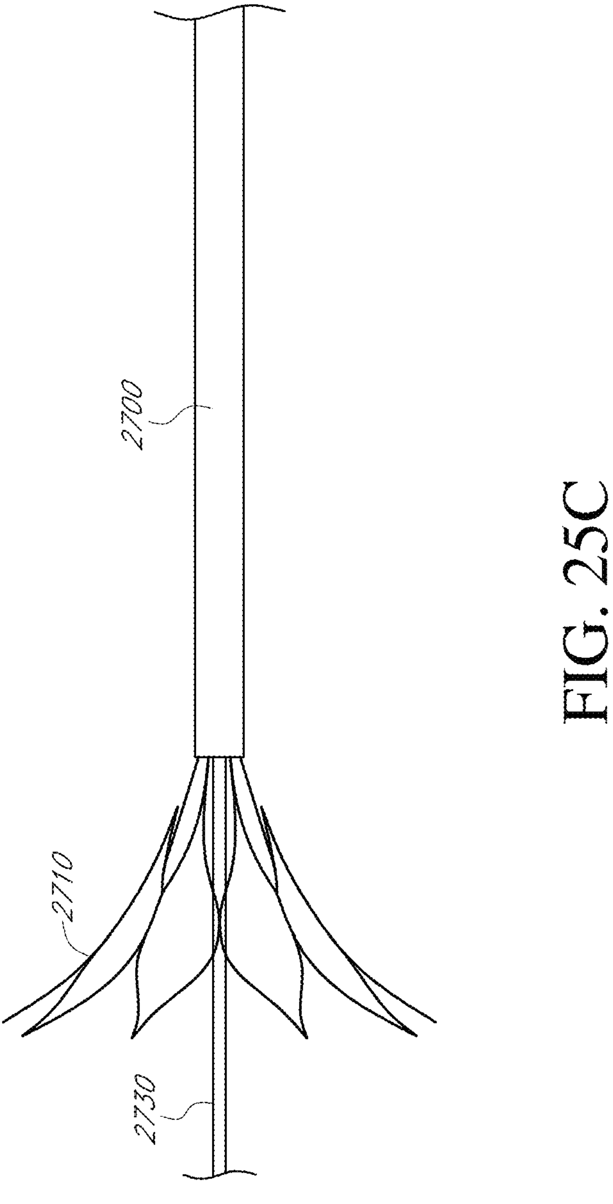
Figure 25D:
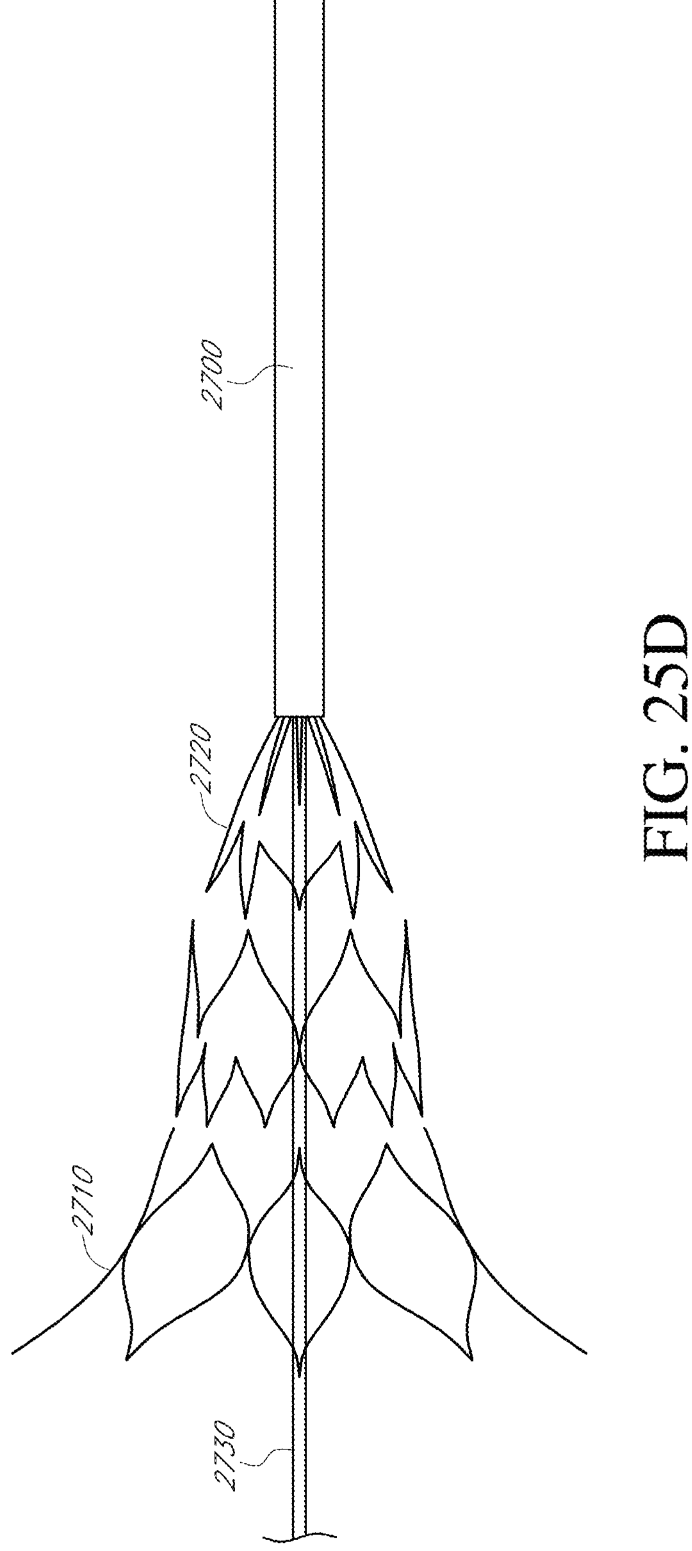

In some embodiments, the first and/or second end sections may be configured to anchor the stent mid-vessel as opposed to an end of a vessel, at an ostium of a vessel, or at a septal wall. Alternatively, as shown in FIG. 11A, a stent may be flared or flanged on only one end, for example the first end section or the second end section. For example, in FIG. 11A, compare an angle 1102 of terminal crown 1106 in the first end section 1100 to an angle 1104 of terminal crown 1108 in the second end section 1110, both relative to a longitudinal axis 1120 of the stent 1150. Angle 1102 of first end section 1100 may be about 45 degrees to about 75 degrees while angle 1104 of the second end section 1110 may be about 15 degrees to about 45 degrees, such that the first end section 1100 is configured to anchor the stent at an ostium of a vessel while the second end section 1110 is configured to anchor the stent mid-vessel. The angle between adjacent struts in each terminal ring of the first and second end sections may be substantially constant or similar but the angle of the terminal crown relative to the longitudinal axis is tailored for either end of vessel anchoring or mid-vessel anchoring. As shown in FIGS. 11B-11C, the terminal rings, crowns, struts, etc. can still anchor the stent in place and allow for the length (measured at body section and second end section) to be adjusted. FIGS. 11B-11C show an adjustment in stent length from about 13 mm (FIG. 11B) to about 16 mm (FIG. 11C). As shown in FIGS. 11B-11C, the measured length of the stent focuses on the functional length (not including the flares that extend from the vessel) since the mid-vessel anchoring struts become part of the body section and as such, the functional length. FIG. 23, which will be described in greater detail below, shows another embodiment of a stent that may be configured to be anchored mid-vessel.

Figure 14:
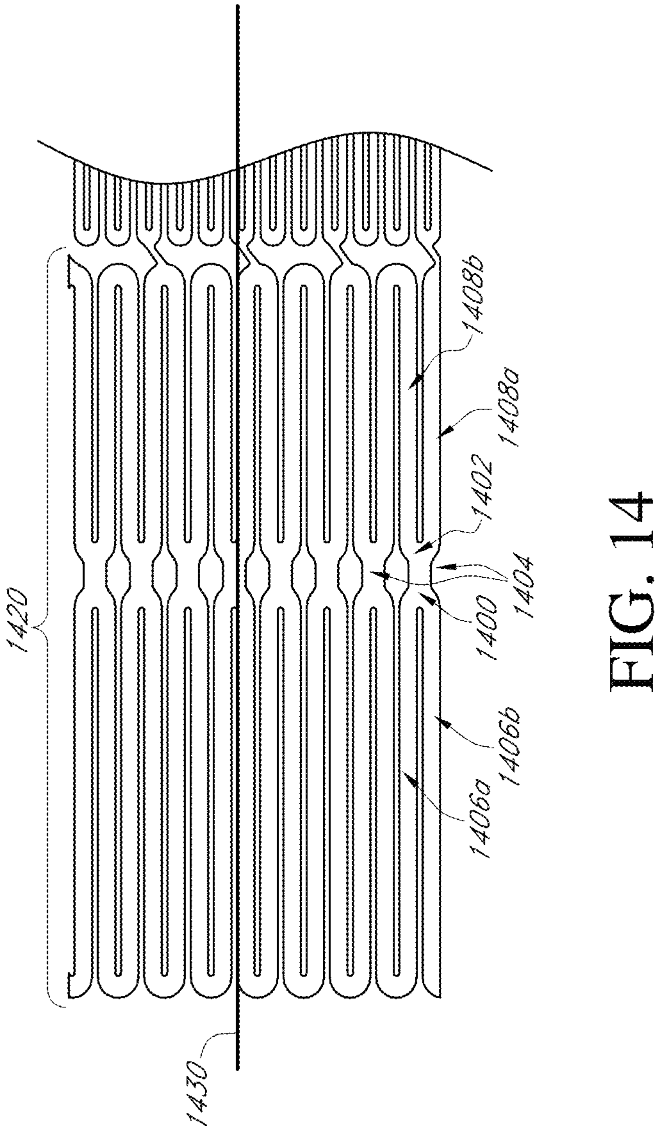
FIG. 14 shows another embodiment of an end section of a stent in a 2D crimped configuration.

FIGS. 14-16 and 18 show various crown and bridge configurations of an end section and/or body section of various stent embodiments in 2D in their as-cut, pre-expanded configurations. FIG. 14 shows one embodiment of a crown and bridge configuration in an end section 1420 (proximal or distal) of a stent. Adjacent terminal struts 1406*a*, 1406*b* are joined at an interior crown 1400 and adjacent penultimate struts 1408*a*, 1408*b* are joined at crown 1402. Interior crown 1400 and crown 1402 are connected via bridge 1404. Said another way, every interior crown 1400 (as opposed to exterior crown or face crown at the proximal or distal face) is connected to a crown of the penultimate struts 1408*a*, 1408*b* via a bridge 1404. In the crimped or unexpanded configuration, bridges 1404 between the terminal 1406 and penultimate struts 1408 are substantially parallel to a longitudinal axis 1403 of the end section 1420. In this embodiment, the terminal and penultimate struts are about 2 mm to about 2.5 mm, preferable about 2.25 mm in length. In some embodiments, the crown and bridge configuration of FIG. 14 is configured to enable expansion of the proximal and/or distal face (symmetrical or asymmetrical) up to a diameter of about 5 mm to about 6 mm, preferably about 5.5 mm.

Figure 15:
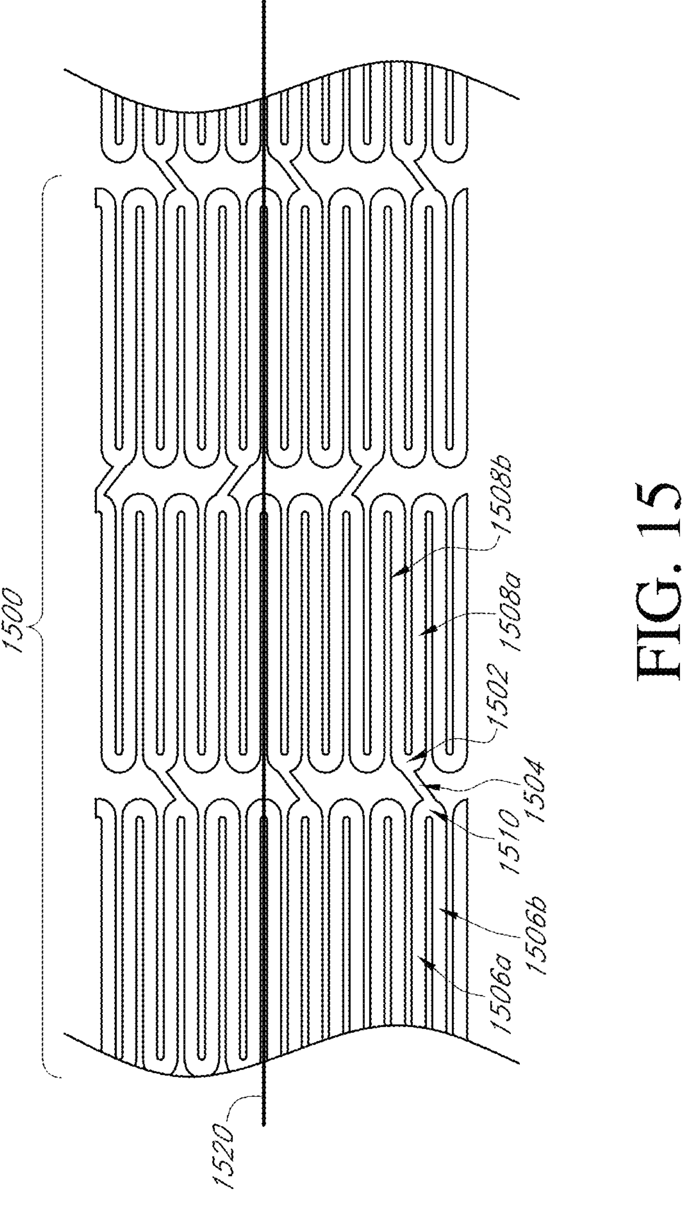
FIG. 15 shows another embodiment of a body section of a stent in a 2D crimped configuration.

Another embodiment is shown in FIG. 15. The stent in FIG. 15 comprises nine crowns per row and 3 bridges per row. The bridges 1504 are angled relative to a longitudinal axis 1520 of section 1500 (body section or end section). For example, terminal strut 1506*a* is joined to adjacent terminal strut 1506*b* at interior crown 1510 and penultimate strut 1508*a* is joined to adjacent strut 1508*b* at crown 1502. Interior crown 1510 is offset relative to crown 1502 such that bridge 1504 is angled relative to a longitudinal axis of the device (in a compressed, 2D, or otherwise unexpanded configuration). In some embodiments, this construction increases flexibility.

Figure 16:
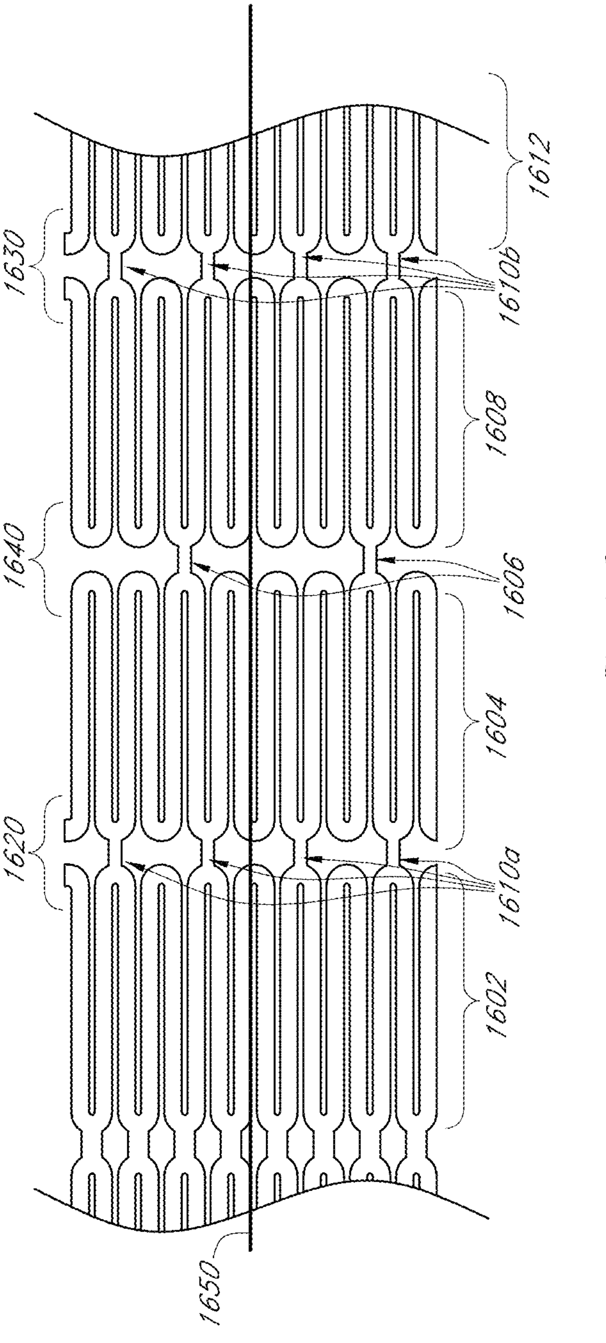
FIG. 16 shows another embodiment of a body section of a stent in a 2D crimped configuration.

FIG. 16 shows another embodiment of connecting regions of a stent. In this embodiment, the number of crowns in the body region is constant but the number of bridges in each connecting region alternates between a higher number and a lower number. For example, connecting region 1620 comprises four bridges 1610*a* between adjacent rings 1602, 1604; connecting region 1640 comprises two bridges 1606 between adjacent rings 1604, 1608; and connecting region 1630 comprises four bridges 1610*b* between adjacent rings 1608, 1612. The number of bridges alternates in each connecting region relative to a number of connecting regions in an adjacent connecting region. Alternating bridge number between rings is configured to enable each bridge to be substantially parallel to a horizontal or longitudinal axis 1650 of the stent. The stent of FIG. 14, in some embodiments, similarly alternates between rings having more crowns or fewer crowns and connecting regions having more bridges and fewer bridges, respectively. Such alternating crown count per ring and/or bridge count between rings may improve strength while maintaining sufficient flexibility (see for example Table 1).

Figure 39:
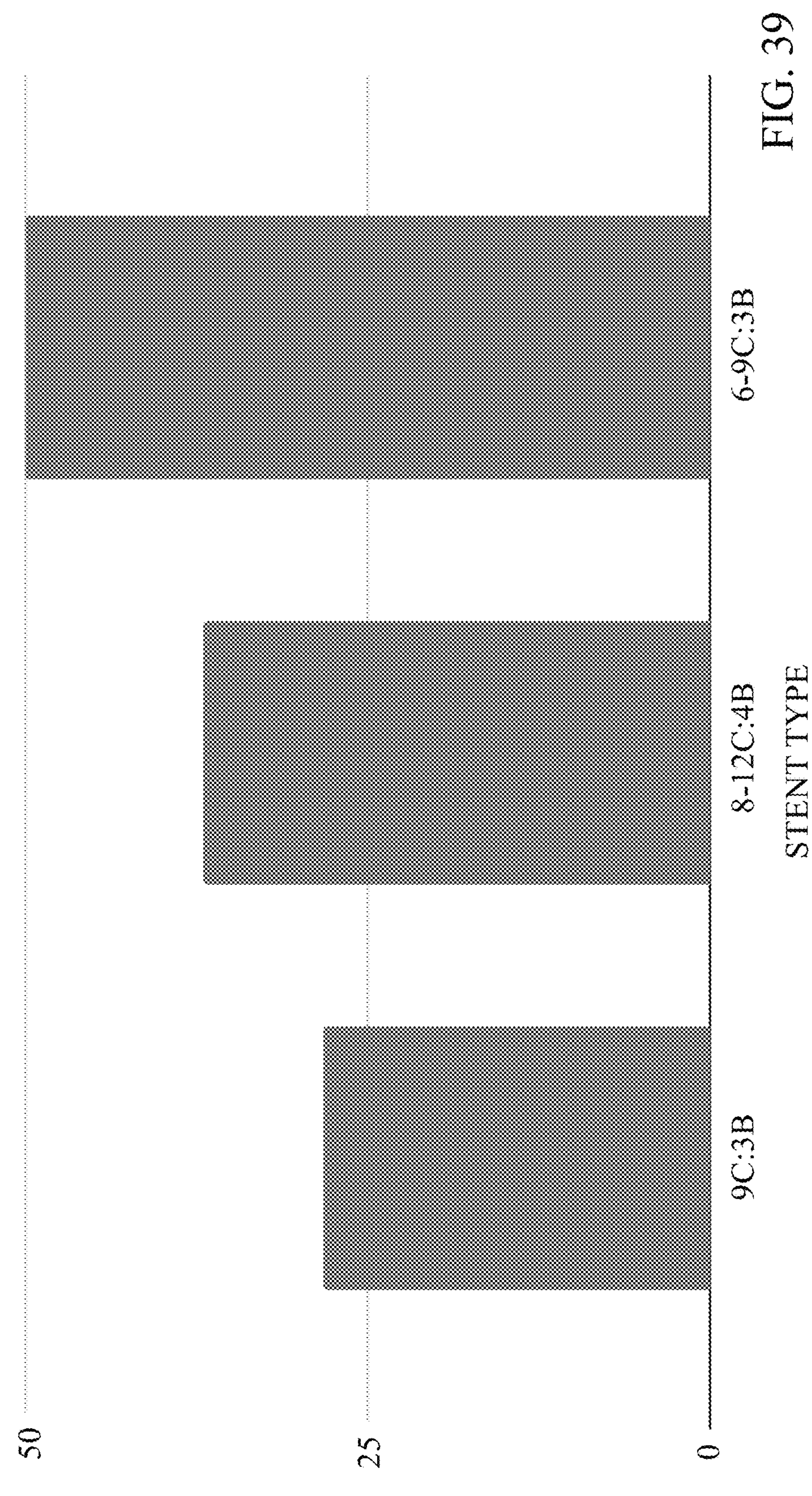
FIG. 39 shows crush test data for various stent designs described herein that alternative in crown number on a ring-by-ring basis.

FIG. 39 shows additional crush test data, run with similar parameters as described above, for stents having such alternating crown and/or bridge count structure. When compared to the strength of a stent having 9 crowns: 3 bridges (shown in FIGS. 38-39), a stent that alternates between 8 crowns and 12 crowns with 4 bridges connecting each ring displays increased strength (e.g., about 37 g) and is very flexible (see Table 1). A stent that alternatives between 6 crowns and 9 crowns with 3 bridges between each ring displays even further increased strength (e.g., about 50 g) and a slight reduction in flexibility (see Table 1) compared to the 8-12 crown: 4 bridge design. In some embodiments, an alternating crown number and/or bridge number at least slightly decreases flexibility while concomitantly increasing strength. Such designs may be a sufficient balance between flexibility and deliverability and strength.

Figure 18:
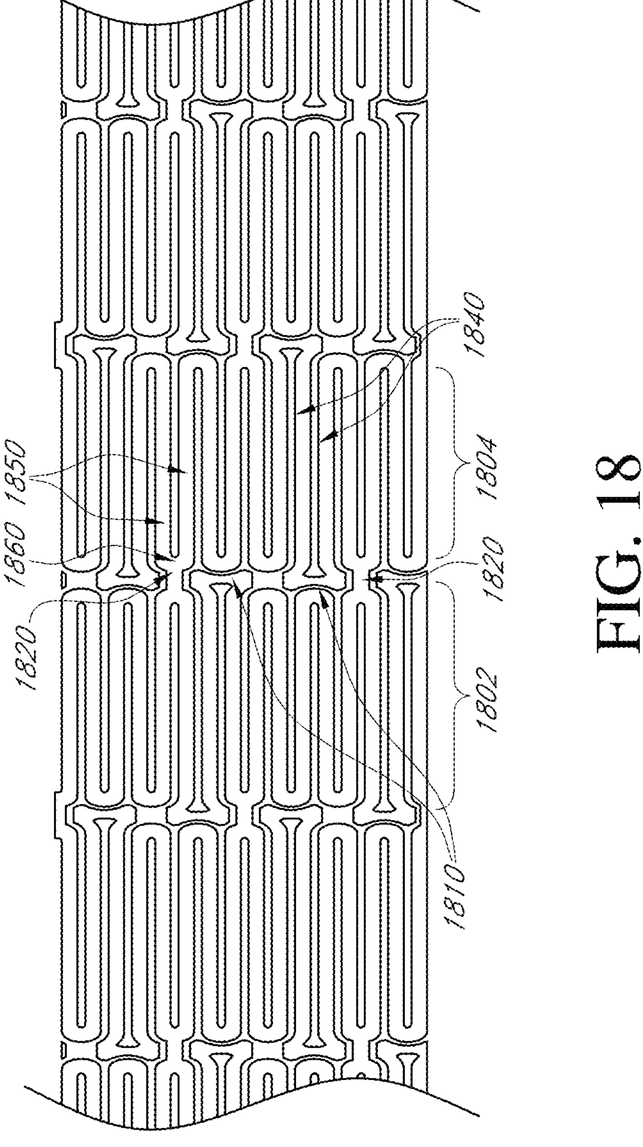
FIG. 18 shows another embodiment of a body section of a stent in a 2D crimped configuration.

FIG. 18 shows another embodiment of connecting regions of a stent. Adjacent struts 1850 may be joined at a curved or looped crown 1860 such that the crown 1860 is joined to an adjacent ring via bridge 1820 (e.g., parallel or angled relative to a longitudinal axis of the stent). In another embodiment, adjacent struts 1840 are joined at crown 1810 that has a substantially flat or slightly concave apex. The concave or flat crown 1810 may or may not be joined to an adjacent ring via a bridge. In some embodiments, this design may confer more pushability when advancing the stent through the delivery system, for example ring 1804 may push against ring 802, or vice versa, during delivery.

Figure 21:
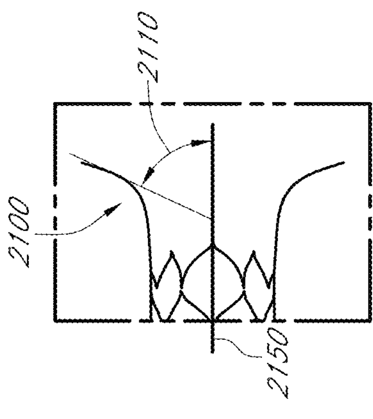
FIG. 21 shows a side profile of another embodiment of an end section of a stent for maintaining a patent lumen or conduit.
Figure 21:
Figure 20:
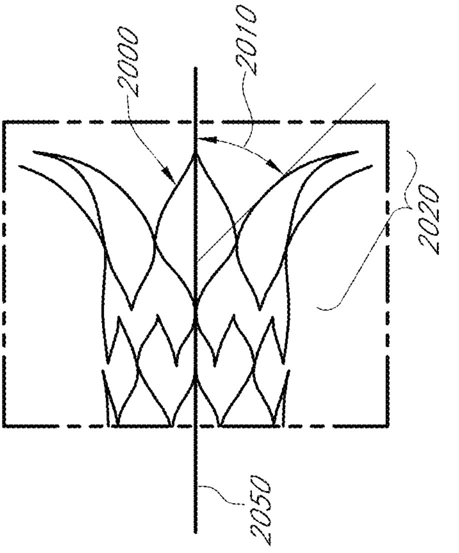
FIG. 20 shows a side profile of another embodiment of an end section of a stent for maintaining a patent lumen or conduit.
Figure 19:
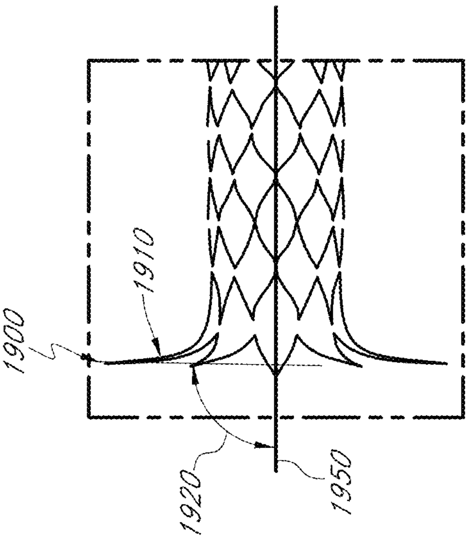
FIG. 19 shows a side profile of one embodiment of an end section of a stent for maintaining a patent lumen or conduit.

FIGS. 19-21 show various schematics of end sections of a stent. For example, the configurations shown in FIGS. 19-21 may be part of a first end section defining a proximal face and/or a second end section defining a distal face. The configurations shown in FIGS. 19-21 may be applied to any of the stent embodiments described elsewhere herein. In one embodiment, as shown in FIG. 19, an end section of a stent may be angled (in its expanded configuration) relative to a longitudinal axis of the stent. The angle 1920 may be about 80 degrees to about 100 degrees, or substantially or about 90 degrees, such that a terminal crown 1900 of a terminal strut 1910 is substantially perpendicular to a longitudinal axis 1950 of the stent. In another embodiment, as shown in FIG. 20, one or more terminal struts 2000 of a stent may flare gradually, for example along an arcuate path 2020, with an elongate section of the strut 2000 being at an angle 2010 of about 30 degrees to about 60 degrees relative to a longitudinal axis 2050 of the stent. In another embodiment, as shown in FIG. 21, one or more terminal struts 2100 of a stent may flare gradually, such that an elongate section is at an angle 2110 of about 70 degrees to about 90 degrees relative to a longitudinal axis 2150 of the stent. The embodiments shown in FIGS. 19-21 each have terminal struts that are longer than the struts in a body section of the stent.

In some embodiments, as shown in the schematic of FIG. 22, a body section 2340 of a stent 2300 may include an expanded lumen 2310 at a region of the body section 2340. For example, the region may be substantially centrally located or may be more proximal to a distal end 2320 or proximal end 2330 of the stent 2300. The bulge or protrusion 2310 may be substantially circumferentially disposed or may be focal or otherwise.

In still another embodiment, as shown in the schematic of FIG. 23, one or more terminal struts 2410 may bend back toward a proximal end 2422 of the stent 2400, such that an angle 2420 of the struts 2410 relative to a longitudinal axis 2430 is about 120 degrees to about 170 degrees.

FIG. 24 shows another embodiment of an end section 2550 of a stent 2500 having a cuff shape. For example, the end section 2550 may comprise a parallel section 2540 relative to a longitudinal axis 2510 of the body section 2560 giving it the cuff-like appearance. Further for example, a distal end 2550 of the stent 2500 has a diameter 2520 that is larger (e.g., about 5% to about 50% larger) than a diameter 2530 of the body section 2560 of the stent 2500.

Figure 27A:
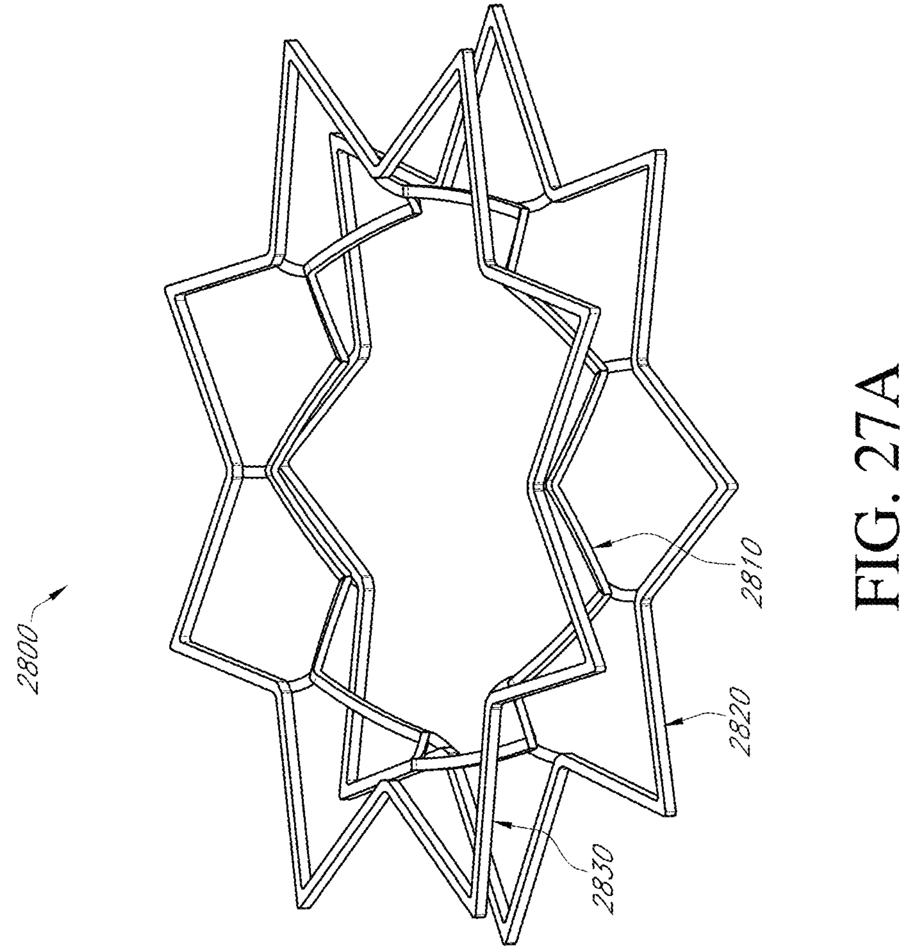
FIG. 27A shows a perspective view of one embodiment of a stent configured for deployment in a septal conduit.
Figure 27B:
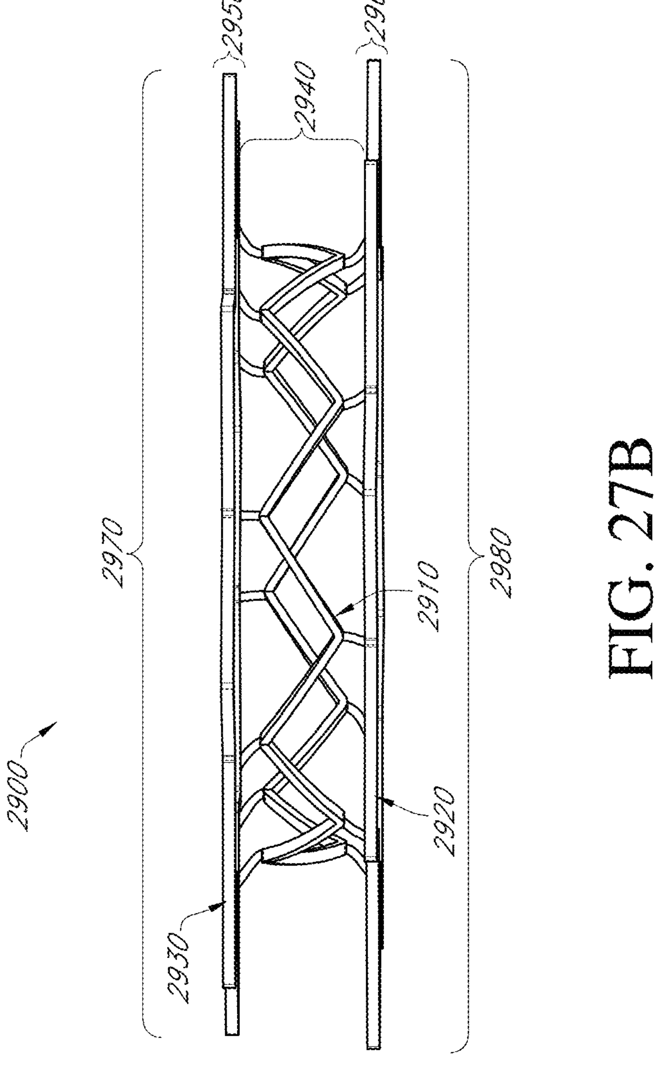
FIG. 27B shows a side view of the stent of FIG. 27A.

In some embodiments, a shorter version of any of the stent designs described herein could also be used to maintain communication between two heart chambers, such as the left and right atria of the heart or an inferior venous baffle or conduit and the right atrium (such as a Fontan fenestration). For example, this could maintain patency of a septostomy or foramen *ovale*. In some embodiments, as shown in FIG. 27A, a shortened stent 2800 may include one to two rings 2810 in a body section with flared end sections 2820, 2830 (e.g., terminal rings that are substantially perpendicular relative to a longitudinal axis of the stent) on either or both first and second ends. This design can also be delivered through a microcatheter using any of the pusherwire designs described herein. FIG. 27B shows a side view of the stent of FIG. 27A for use as a septal conduit. As shown in FIG. 27B, the septal conduit stent 2900 comprises a body section 2940 having one ring 2910 (although body sections with more than one or a plurality of rings are also contemplated), a first end section 2950 defining a first face 2970 and a second end section 2960 defining a second face 2980. The first face 2970 may comprise ring 2930 and the second face 2980 may comprise ring 2920, although end sections with a plurality of rings are contemplated herein. In fact, any of the stent embodiments described herein may be adapted for use in the treatment of septal conduit defects.

In some embodiments, any of the stents described herein may comprise an anti-thrombogenic, anti-restenotic surface treatment(s) or coating(s), an anti-proliferative coating, a friction reducing coating, or any other coating(s) known in the art. Further, any of the stents described herein may be configured as a drug-eluting stent.

In any of the stent embodiments described herein, two or more rings in the body section, first end section, and/or second end section may be tethered together to form a segment. Tethering adjacent rings to one another may prevent rings from flipping in orientation during deployment and scaling in bends, which is when two disconnected stent rings or segments hinge at a turn like protruding scales to create a potential kink point. For example, an electrochemical reaction may be used to separate a binding section between two adjacent sections. In some embodiments, a hook system may be used to join adjacent segments, such that a deployment catheter is twisted to disengage segments. Further, in some embodiments, a segment may be nested in an adjacent ring, such that the next segment may be rotated to disengage the segment. In such rotation dependent embodiments, rotation may only be desired when disengaging segments so that the stent may be advanced through tortuous anatomy without disengaging (or only disengaging when properly deployed). As such, to limit rotation outside of disengagement, one or more portions of each segment may not connect to the adjacent segment.

Figure 13:
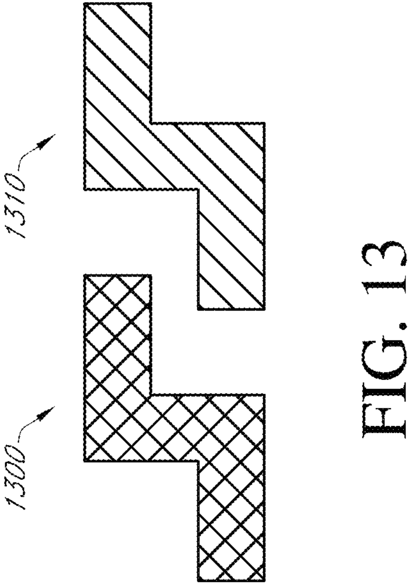
FIG. 13 shows another embodiment of a locking feature between adjacent stent rings or between a stent and a hub of a delivery system.
Figure 12:
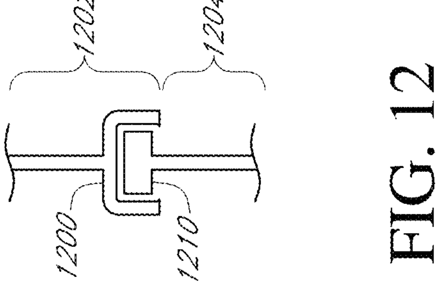
FIG. 12 shows one embodiment of a locking feature between adjacent stent rings or between a stent and a hub of a delivery system.

FIGS. 12-13 show various examples of tethering mechanisms. FIG. 12 shows a lollipop or paddle structure that may be used to tether adjacent segments of a stent together or tether a stent to a delivery system for deployment. For example, a first side 1202 of one segment or a stent may have a female mating portion 1200 and a second side 1204 of an adjacent segment or delivery system may have a male mating portion 1210 (e.g., paddle or lollipop). In another embodiment, as shown in FIG. 13, each segment 1300, 1310 may include a bias-cut pattern for nesting with adjacent segments or tethering the stent to the delivery system. Further, one of skill in the art will appreciate that the delivery system may comprise the female connector 1200 while the stent may comprise the male connector 1210.

In some embodiments, the stents described herein are (1) able to be manufactured in diameters from about 3 mm to about 5 mm in 0.5 mm increments, (2) deliverable through a 4F sheath or smaller, and (3) have a radial force at least as high as the average radial force ranging from approximately 0.20 N/mm at 1 mm of compression to about 0.3 N/mm at 2 mm of compression. In some embodiments, the stent can additionally, or alternatively, completely cover (e.g., within 1 mm) a majority of ductus anatomies (e.g., 4 of 6 ducts in developed models with ductus lengths ranging from about 8 mm to about 28 mm) without extending into either the aorta or the pulmonary arteries by more than about 2 mm to about 3 mm.

Delivery Systems

Figure 28:
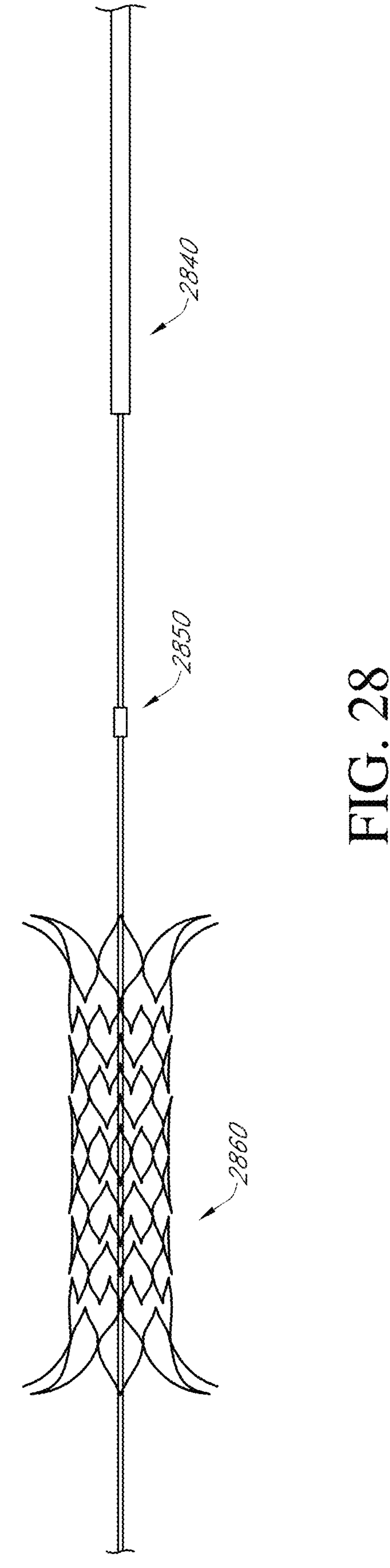
FIG. 28 shows one embodiment of a delivery system, comprising a pusherwire, stent, and microcatheter, for any of the stent embodiments described herein.

Any of the stents described herein may be delivered via a microcatheter-based delivery system. A general delivery system is shown in FIG. 28 and comprises a microcatheter 2840 and a pusherwire 2850 configured to deliver a stent 2860. Any of the delivery systems described herein may be smaller, more flexible, and less traumatic to the ductus or heart chamber than a sheath or stiff balloon-expandable system. For example, interventionalists maintain that 2.7F microcatheters can cross 100% of the ductus anatomies they have encountered, whereas less flexible balloon delivery systems are often unable to navigate the ductus due to their stiffness.

In some embodiments, a microcatheter-based delivery system may use a laser-cut hypotube technology that allows for thinner walls, seamless transition zones, and greater flexibility with lower kink radius than standard braided configurations. The microcatheter-based delivery systems described herein: (1) have an about 2.7F outer diameter, reducing crossing profile compared to a 3.3F or 4F sheath or balloon-expandable coronary stent and fits through a 3.3F sheath to minimize iatrogenic vessel damage, while enabling contrast runs for angiography during stent placement through the sheath; (2) enable access via femoral, carotid, or axillary arteries, as the ductus may need to be accessed from any of those vessels to obtain the necessary trajectory, without excessive length, for ease-of-use in a pediatric patient; and (3) can track over existing 0.014" guidewires through a ductus arteriosus that undergoes more than one full 360 degree turn (e.g., Type III ductus tortuosity index, as shown in FIG. 5C).

In some embodiments, the stent and delivery system are designed uniquely for neonatal ductus arteriosus stenting to overcome the anatomical challenges of small, tortuous vessels, which are prone to spasm, while enabling placement of a properly sized stent from end-to-end of the ductus without protrusion into the surrounding vessels.

Figure 29:
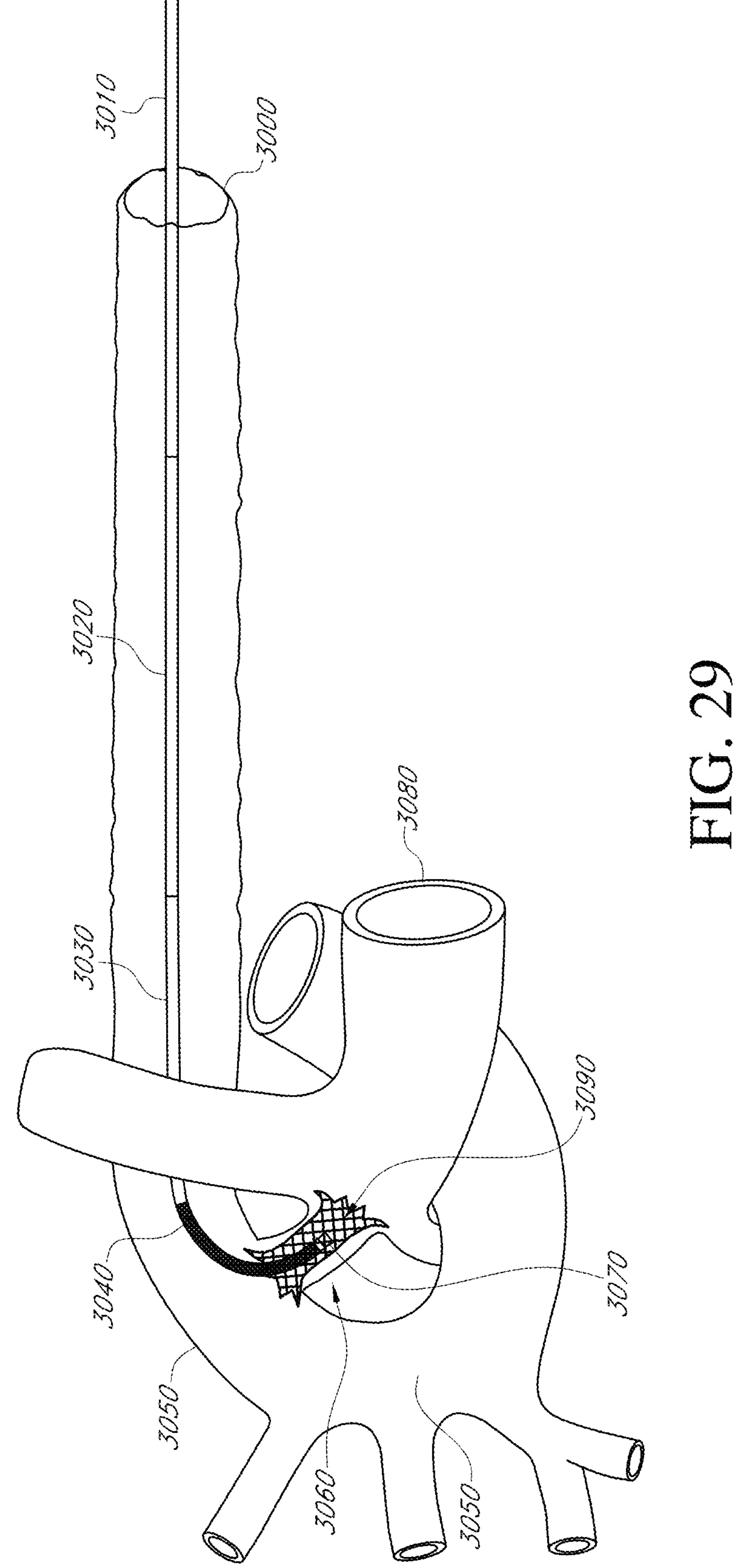
FIG. 29 is a schematic showing various anatomical considerations for a stent and associated delivery system.

FIG. 29 shows a schematic of various anatomical considerations in stent and delivery system design. For example, a microcatheter delivery system traveling through the aorta 3050 to the ductus 3060 may be segmented into several zones, as shown in FIG. 29, each having their own bend radius, length, and durometer. As shown in FIG. 29, when approaching the ductus 3060 from the aorta 3050, zone 3010 of a catheter is configured to be advanced through the descending femoral artery 3000 such that is has a bend radius of about 7 mm to about 8 mm, a length of about 52 cm to about 59 cm, and a durometer of about 40 to about 90 Shore A. Zone 3020 of the catheter is further configured to be advanced through the femoral artery 3000 such that is has a bend radius of about 4 mm to about 5 mm, a length of about 4 cm to about 6 cm, and a durometer of about 40 to about 90 Shore A. Next, zone 3030 of the catheter is configured to be advanced through the femoral artery 3000 proximate to the aortic arch 3050 such that it has a bend radius of about 1 mm to about 4 mm and durometer of about 20 to about 40 Shore A. Zone 3040 of the catheter is configured to navigate the aortic arch 3050 such that is has a bend radius of about 2.5 mm, a length of about 0.5 cm to about 1 cm, and a durometer of about 20 to about 40 Shore A. The catheter is further configured to navigate an inferior portion of the aortic arch 3050 and enter the ductus arteriosus 3060, which has a length of about 8 mm to about 28 mm. The distal tip 3070 of the catheter deploys the stent 3090. While FIG. 29 shows approaching the ductus from the aorta, one of skill in the art will appreciate that the ductus can also be approached from the pulmonary artery 3080, both approaches shown above in FIGS. 1A-1D and FIGS. 2A-2D. The stent and/or delivery catheter may be similarly manufactured to have flexibility to match the specific requirements of each zone.

Embodiments of the stent delivery system may use a microcatheter made of laser-cut hypotube technology that allows for thinner walls, seamless transition zones, and greater flexibility with lower kink radius than standard braided configurations. Additionally, microcatheter delivery systems with braided or coiled reinforcement and multiple transition zones created with outer polymer jackets of variable durometers and/or variation of the pitch of the coil or per-inch-crosses (PIC) of the braid may be used to deliver the stent. The delivery system can be configured to fit through a 4F sheath to minimize iatrogenic vessel damage. In some embodiments, the delivery system enables access via femoral, carotid, or axillary arteries, as the ductus may need to be accessed from any one of those vessels to obtain the necessary trajectory. The delivery system can be configured to track over existing guidewires through a ductus arteriosus that undergoes more than a 360 degree turn (Type III ductus tortuosity index, FIG. 5C). As noted above, the stent and delivery system are designed uniquely for neonatal ductus arteriosus stenting to overcome the anatomical challenges of small, tortuous vessels, while enabling placement of a properly sized stent from end-to-end of the ductus without protrusion into the surrounding vessels.

In some embodiments, any of the delivery systems described herein may be configured to deploy a variety of devices including, but not limited to: stents (any of the embodiments described herein), flow restrictor devices, occlusion devices, septal conduit devices (FIGS. 27A-27B), or otherwise implants. Such an array of devices may be referred to herein as implants.

In some embodiments, an implant may be disengaged from a delivery system by applying voltage to release a connector between the implant and delivery system; by using one or more sugar moieties that dissolve to separate the implant from the delivery system; by using a softer hub (e.g., silicone) to compress implant ends to hold them in place; by having a lock and key mechanism via a marker on the implant and a hub on the delivery system (e.g., FIG. 31); by having a lock and key mechanism between adjacent implant segments, such that each implant crest to valley is reversibly connected to keep the segments nested; by having a twisting mechanism (e.g., struts in between that were meant to twist) so as to adjust lengths between segments; and/or having designs that promote unidirectional deployment (e.g., having subsequent implant segments increase in diameter as the implant is advanced towards the aorta (or pulmonary artery depending on approach), which can also help with nesting and deploying one segment at a time). In some embodiments of the twisting mechanism, the twisting mechanism may be reserved for a proximal end of deployment at the aortic side (or pulmonary artery side depending on approach).

Figure 30:
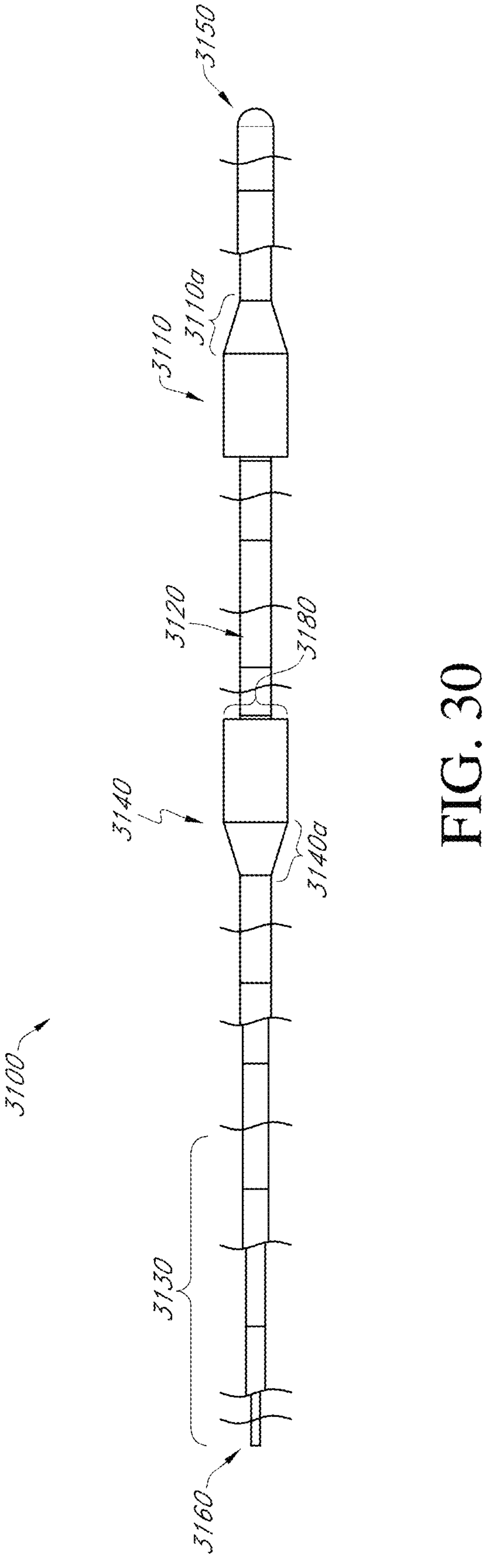
FIG. 30 shows one embodiment of a delivery system for any of the stent embodiments described herein.
Figure 34:
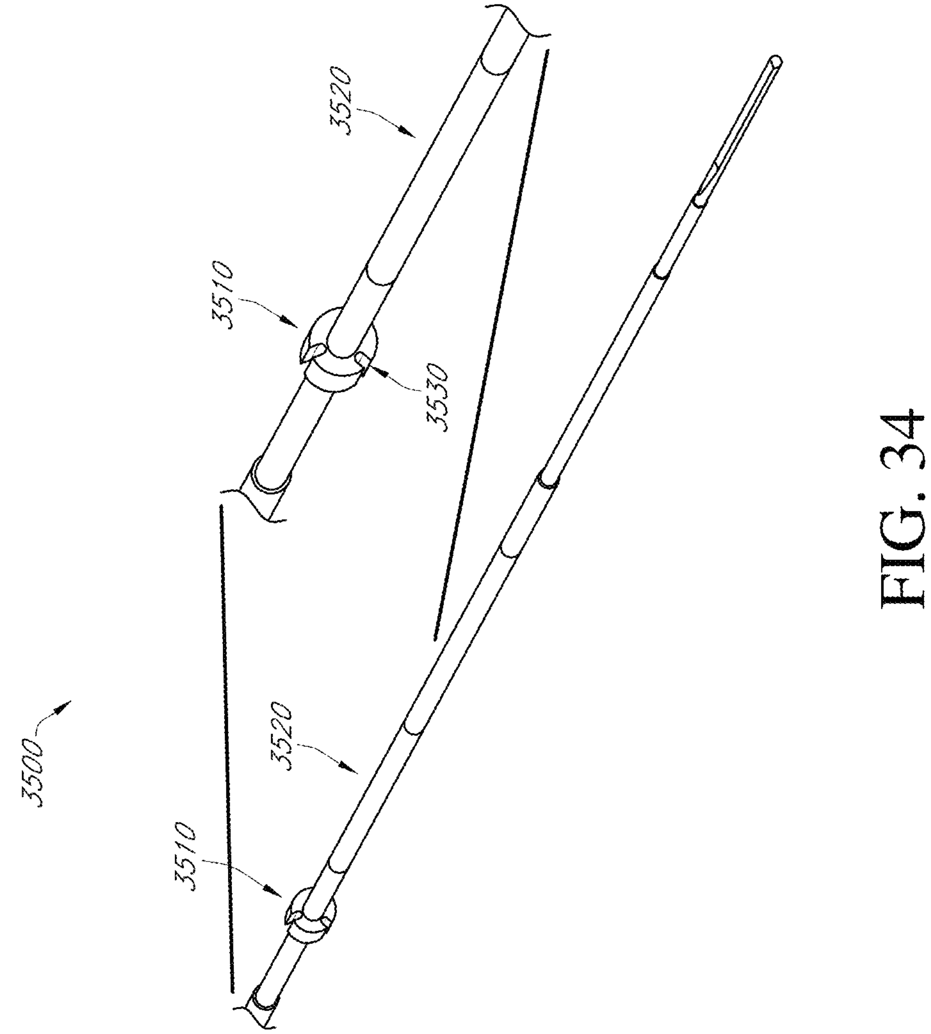
FIG. 34 shows a partial view of another embodiment of a pusherwire of a delivery system for any of the stent embodiments described herein.
Figure 35:
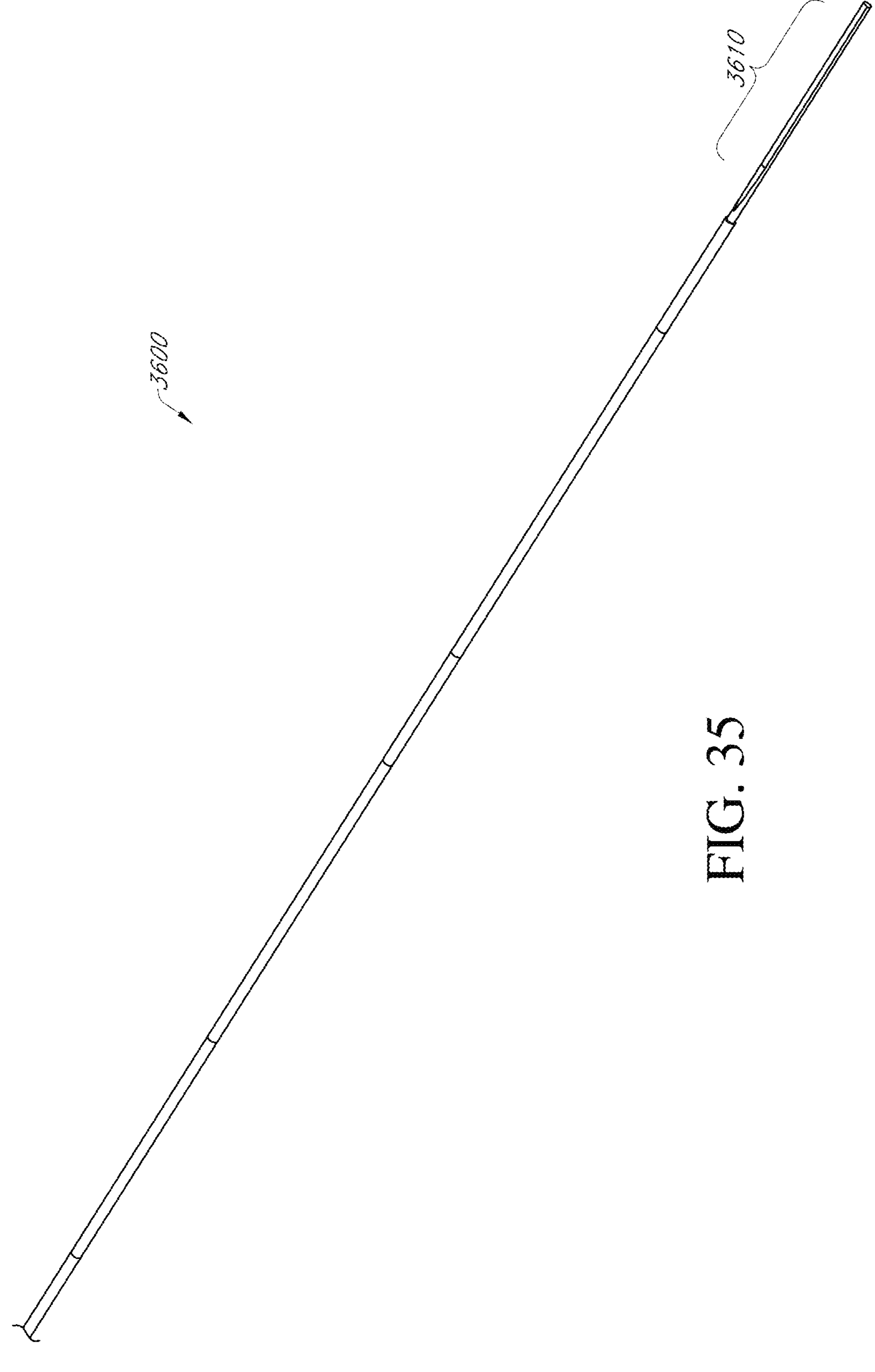
FIG. 35 shows a partial view of another embodiment of a pusherwire of a delivery system for any of the stent embodiments described herein.
Figure 36:
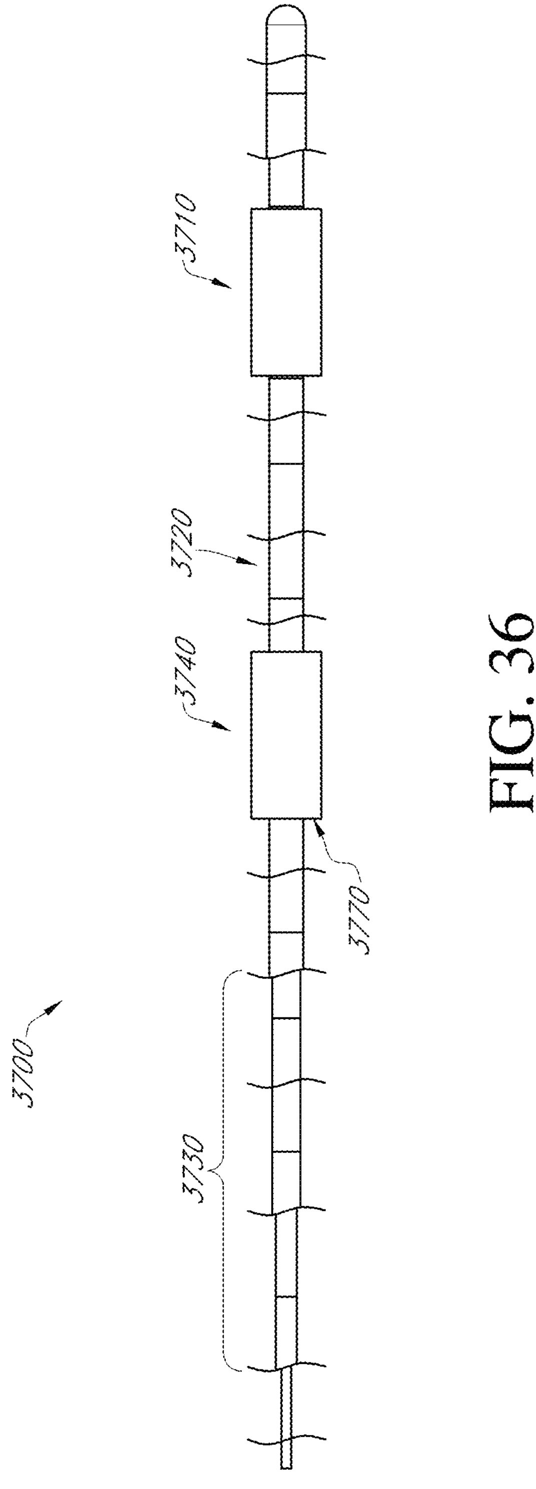
FIG. 36 shows another embodiment of a pusherwire of a delivery system for any of the stent embodiments described herein.

FIGS. 30-37 show various pusherwire embodiments that may be used with or adapted for use with any transfer sheaths and microcatheters known in the art. FIG. 30 shows a pusherwire 3100 comprising a first hub 3110 and a second hub 3140 that are used to manipulate and/or deliver any of the stents described herein within a catheter delivery system. Although the embodiment of FIG. 30 is shown with two hubs, one of skill in the art will appreciate that the embodiment may also function with a single hub near a proximal end of the pusherwire. The outer diameter of hub 3110 may be substantially similar to the outer diameter of the microcatheter. A proximal end 3110*a* of hub 3110 tapers towards a proximal end 3150 of the pusherwire 3100, and a distal end 3140*a* of hub 3140 tapers towards a distal end 3160 of pusherwire 3100. Alternatively, as shown in FIG. 36, a first and second hub 3710, 3740 of a pusherwire 3700 may each have a substantially uniform or consistent outer diameter or circumference (e.g., may not taper). Returning to FIG. 30, the implant may be positioned between hubs 3140, 3110 at implant receiving section 3120 (shown as implant receiving section 3720 between hubs 3710, 3740 in FIG. 36). As shown in FIGS. 30 and 36, the distal end 3130, 3730 of the pusherwire 3100, 3700, respectively, may include a soft or flexible segment of leading wire, for example approximately 5 cm beyond the distal end 3130, 3770, respectively, of the distal hub 3140, 3740, respectively. Implant section 3120 may comprise a soft polymer (e.g., about 25D to about 35D durometer polymer or silicone) that has a diameter that is approximately equal to an inner diameter of the implant positioned thereon (e.g., the crimped stent). Implant section 3120 may be configured to engage the implant to help control its positioning during deployment. In some embodiments, a diameter 3180 of the distal hub 3140 may be substantially equal to or similar to an inner diameter of the crimped stent in the microcatheter and located under the stent. The distal hub 3140 may engage with one or more features at the distal end of the stent, such as radiopaque markers, to allow the stent to be tensioned in the microcatheter or during deployment to stretch the stent.

Figure 31:
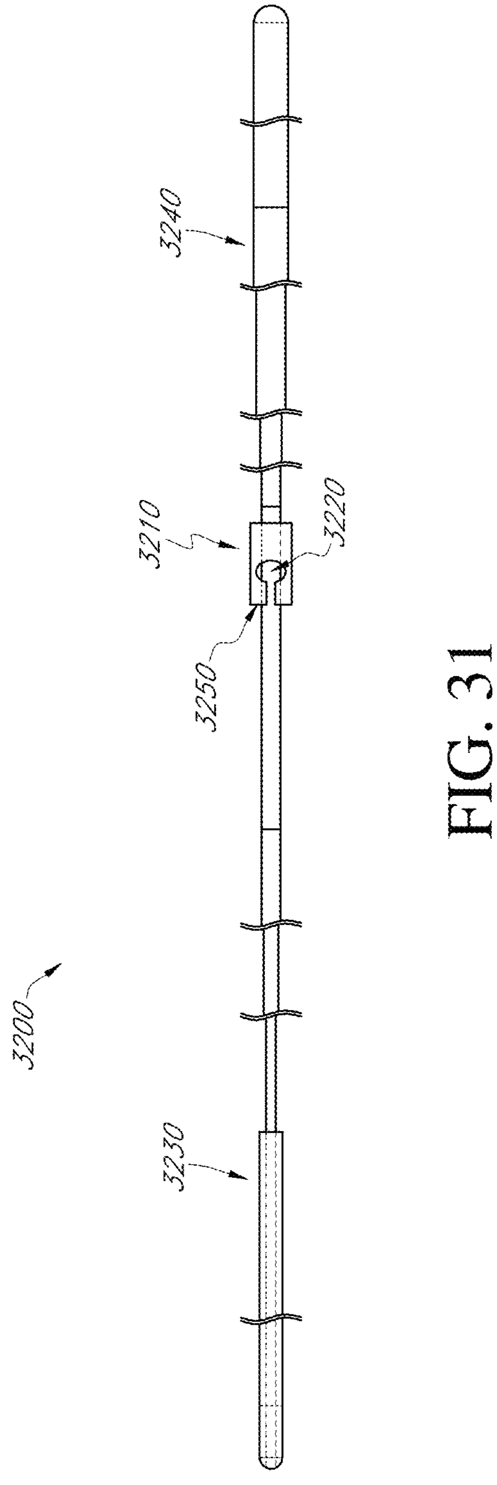
FIG. 31 shows another embodiment of a delivery system for any of the stent embodiments described herein.
Figure 32:
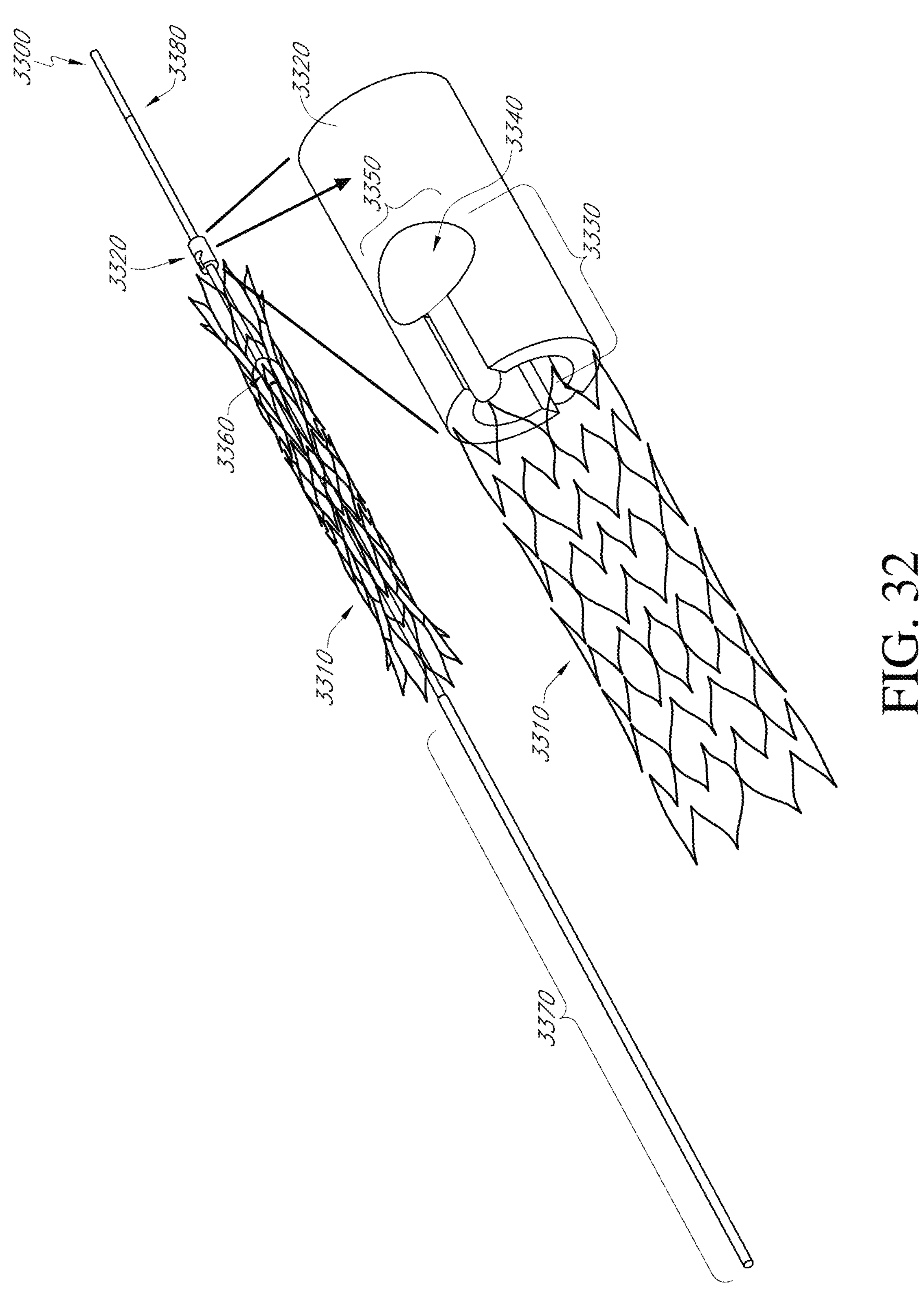
FIG. 32 shows another embodiment of a delivery system for any of the stent embodiments described herein.

FIGS. 31-32 shows another embodiment of a pusherwire. As shown in FIG. 31, pusherwire 3200 includes a proximal end 3240, distal end 3230, and a hub 3210 that is used to push the stent within a microcatheter delivery system. The hub 3210 may be about or approximately equal to or similar to an outer diameter of the microcatheter. As shown in FIGS. 31-32, the hub 3210 defines one or more grooves or cutouts 3220 that are configured to reversibly mate with one or more features located at a proximal end of an implant. The functionality of the hub 3210 is configured to control implant deployment and optionally implant stretching or positioning. The distal end 3230 of the pusherwire 3200, as above, may comprise a soft or flexible segment of leading wire beyond the distal end 3250 of the hub 3210.

Figure 17B:
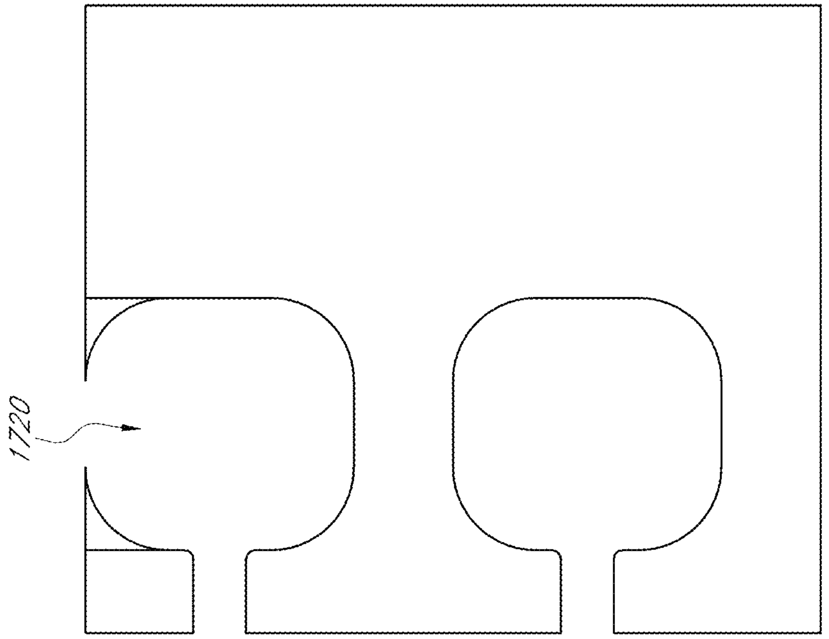
FIGS. 17A and 17B show a male portion of a stent and a female portion of a delivery system, respectively, for enabling controlled deployment and/or stent elongation or stretching during deployment.
Figure 17A:
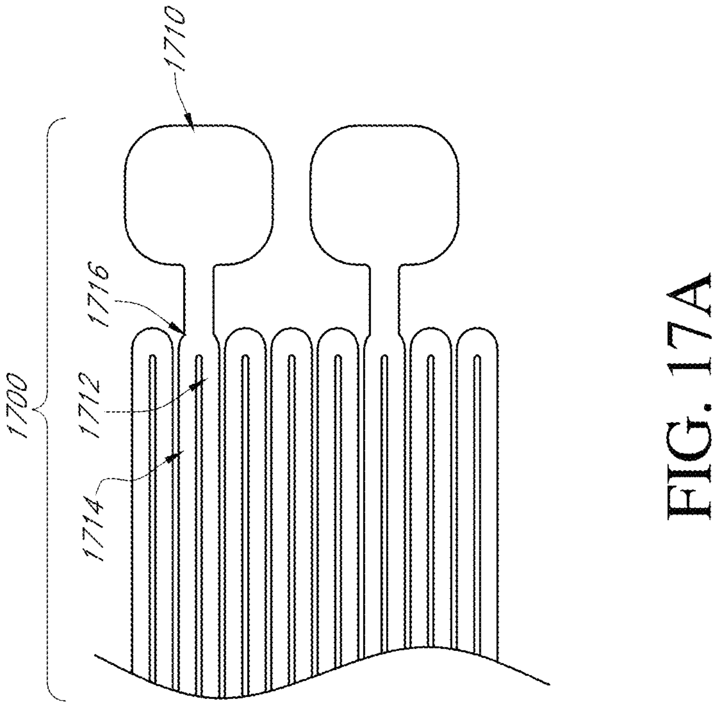

FIG. 32 and FIGS. 17A-17B show various zoomed in views of the embodiment of FIG. 31 and interaction between and pusherwire and the stent. As shown in FIGS. 17A-17B and as similar to FIG. 12, a proximal end 1700 of the stent may include a delivery system connector 1710 (e.g., male connector, paddle, lollipop, etc.). For example, adjacent struts 1712, 1714 may be joined at an exterior crown 1716 that is attached to a delivery system connector 1710. Delivery system connector 1710 is configured to be coupled to a complementary connector 1720 (shown in FIG. 17B), for example, as part of a hub of a delivery system, for enabling stent elongation or stretching during deployment to ensure complete vessel coverage. Although the male connector is shown on the stent and the female connector on the delivery system, one of skill in the art will appreciate that the female connector may be on the stent and the male connector on the delivery system. The length of a male portion (of the delivery system connector 1710) may be about 1.0 mm to about 2 mm, preferably about 1.5 mm.

FIG. 32 shows a pusherwire 3300 engaged with a stent 3310. Pusherwire 3300 comprises hub 3320 that is coupled to the stent 3310 at hub-stent interface 3330. As shown in this embodiment, the stent 3310 includes a proximal male connector 3340 that is complementary to a female connector 3350 of the hub 3320. The pusherwire 3300 may optionally include a second hub 3360 that is configured to be positioned under a stent 3310 located on the pusherwire 3300 to control stent release and/or elongation. A distal end 3370 of the pusherwire 3300 may be radiopaque and comprise a polymer jacket and/or a hydrophilic coating. A proximal end 3380 of the pusherwire 3300 may comprise a variable stiffness core wire comprising, for example Nitinol and/or stainless steel with a polymer jacket.

Figure 33:
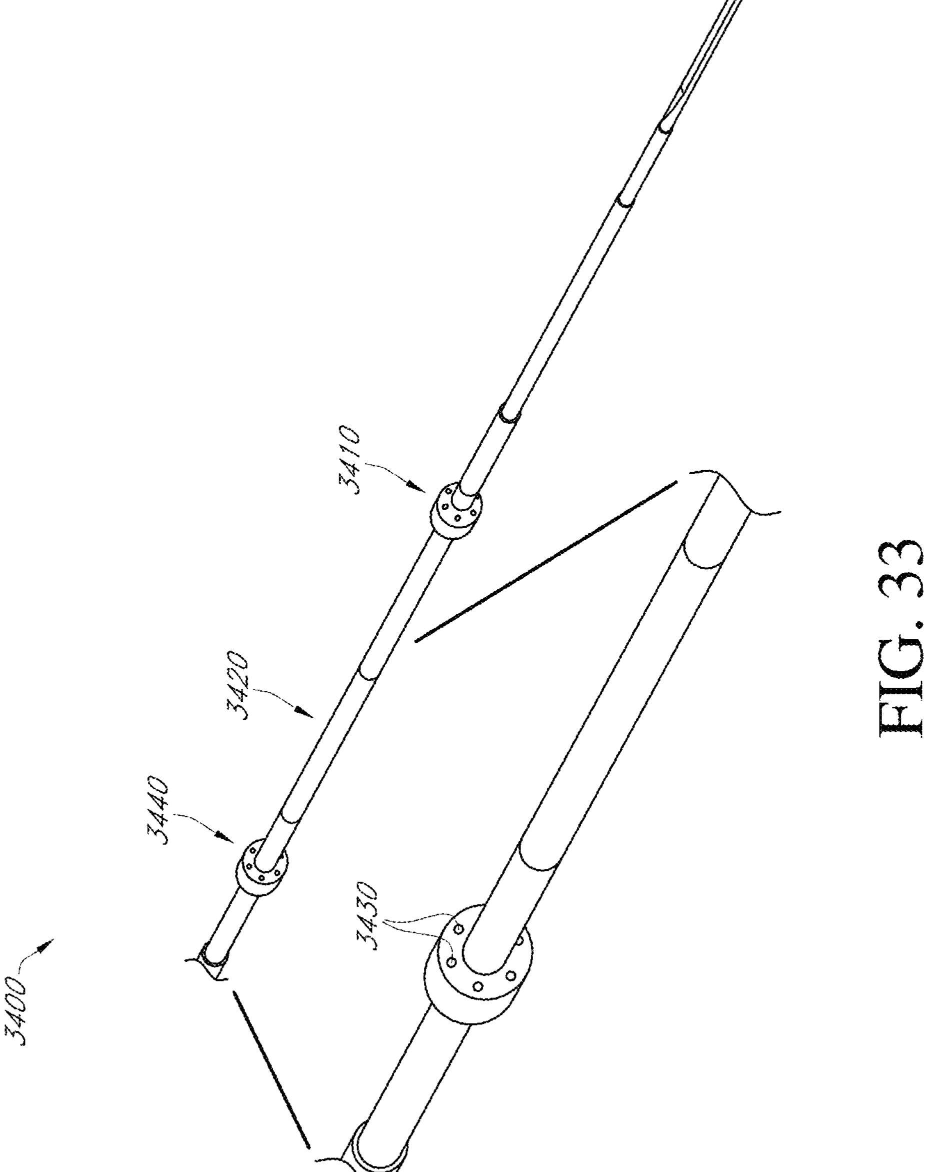
FIG. 33 shows a partial view of one embodiment of a pusherwire of a delivery system for any of the stent embodiments described herein.

FIG. 33 shows a pusherwire 3400 comprising two hubs 3410, 3440 that are used to push the stent within a delivery system. In some embodiments, one or both hubs 3410, 3440 are approximately the outer diameter of the microcatheter. The implant is configured to be positioned between the hubs 3410, 3440 at implant section 3420. Implant section 3420 may comprise or be formed of a soft polymer that may be approximately the inner diameter of the crimped stent. Implant section 3420 may be configured to engage the implant to help control its position during deployment. One or both of the hubs 3410, 3440 may define one or more apertures 3430 therethrough to allow contrast or other injections to pass through the pusherwire 3400 and implant during delivery.

FIG. 34 shows a pusherwire 3500 comprising one or more hubs 3510 (e.g., a second hub may be positioned distally to hub 3510) and implant section 3520, as described elsewhere herein. However, in this embodiment, hub 3510 defines one or more concave sections, grooves, slits, or slots 3530 to allow contrast or other injections to pass through the pusherwire 3500 and implant during delivery.

Figure 37:
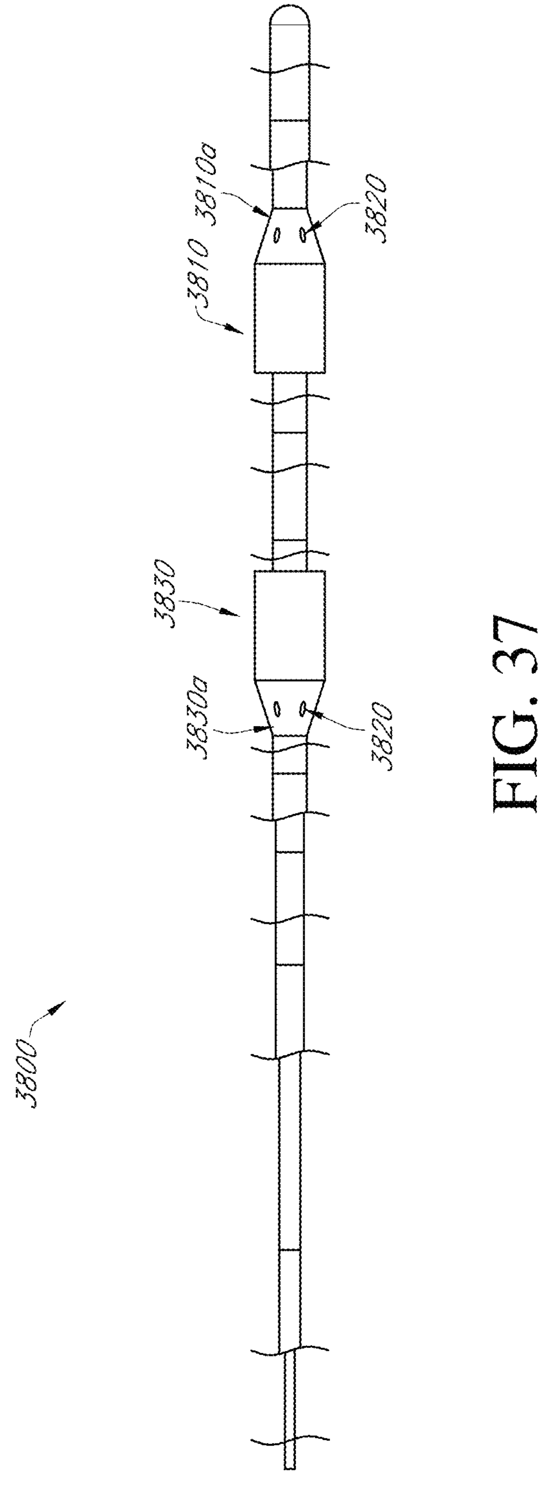
FIG. 37 shows another embodiment of a pusherwire of a delivery system for any of the stent embodiments described herein.

FIG. 37 shows another embodiment of a pusherwire 3800 that is similar to that of FIG. 30, except in the embodiment of FIG. 37, the tapered sections 3810*a*, 3830*a* of one or both hubs 3810, 3830, respectively, define one or more apertures 3820 to allow contrast or other injections to pass through the pusherwire 3800 and implant during delivery. Any of the hub embodiments described herein may have one or more features or define one or more openings or slits to allow contrast or other injections therethrough.

FIG. 35 shows a pusherwire 3600 comprising a distal end segment 3610. The distal end segment 3610 may comprise a flat ribbon tip, polymer tip, or coils to make an atraumatic and flexible tip. In some embodiments, distal end segment 3610 extends beyond a leading edge of the stent when being delivered to allow the pusherwire 3600 to be parked within a branch pulmonary artery to keep wire position through the ductus during stent delivery. The distal end segment 3610 of the pusherwire 3600 may also have nitinol shape set expanding elements which help anchor it in place.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for case of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath"

other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for insertion into a blood vessel lumen for maintaining a patency of a ductus arteriosus, comprising:

a first end section comprising a first plurality of struts configured to expand to define a proximal face having a first diameter;

a second end section comprising a second plurality of struts configured to expand to define a distal face having a second diameter;

a body section extending between the first end section and the second end section and defining a third diameter, the body section having a third plurality of struts; and a device lumen extending through the first end section, the body section, and the second end section such that blood is configured to flow through the device lumen, wherein the device is configured to transition from a crimped configuration to an expanded configuration, such that, in the crimped configuration, a crimped diameter of the device is less than a lumen diameter of a 2.7 Fr catheter and, in the expanded configuration, the device is configured to expand to an expansion diameter of greater than about 3 mm measured at the body section, and wherein the device, in the expanded configuration, has a radial resistive force greater than about 0.20 N/mm at 1 mm of compression.

2. The device of claim 1, wherein, in the expanded configuration, the first diameter of the proximal face is about 20% to about 50% larger than the third diameter of the body section, and wherein, in the expanded configuration, the second diameter of the distal face is about 20% to about 50% larger than the third diameter of the body section.

3. The device of claim 1, wherein:

each of the first plurality of struts has a first length, each of the second plurality of struts has a second length, and each of the third plurality of struts has a third length;

the third length is shorter than the first length; and the third length is shorter than the second length.

4. The device of claim 3, wherein the first length of each of the first plurality of struts and the second length of each of the second plurality of struts is about 2.5 mm to about 4 mm; and wherein the third length of each of the third plurality of struts in about 1 mm to about 2 mm.

5. The device of claim 1, wherein the first plurality of struts of the first end section is arranged in one or more first rings; and wherein the one or more first rings comprise 2 to 5 first rings.

6. The device of claim 5, wherein adjacent first rings in the first end section are connected via 3 to 9 first bridges.

7. The device of claim 6, wherein each first bridge has a first length between about 0.1 mm and about 0.25 mm.

8. The device of claim 1, wherein:

the second plurality of struts of the second end section is arranged in one or more second rings;

wherein the one or more second rings of the second end section comprise a second terminal ring comprising a second terminal plurality of struts, a second penultimate ring comprising a second penultimate plurality of struts, and a second antepenultimate ring comprising a second antepenultimate plurality of struts; and a second terminal strut length of a second terminal strut is longer than a second penultimate strut length of a second penultimate strut, which is longer than a second antepenultimate strut length of a second antepenultimate strut.

9. The device of claim 1, wherein the first end section and the second end section are configured to anchor the device in at least a portion of an aorta ostium and at least a portion of a pulmonary artery ostium, respectively, such that the body section spans a ductus arteriosus.

10. The device of claim 1, wherein a terminal subset at the proximal face of the first plurality of struts forms a proximal angle with respect to a longitudinal axis of the device; and wherein a terminal subset at the distal face of the second plurality of struts forms a distal angle with respect to a longitudinal axis of the device.

11. The device of claim 10, wherein each of the proximal angle and the distal angle is about 30 degrees to about 110 degrees.

12. The device of claim 11, wherein each of the proximal angle and the distal angle is about 45 degrees to about 90 degrees.

13. The device of claim 1, further comprising a delivery system comprising a microcatheter and a pusherwire, wherein the pusherwire is configured to be advanced through a lumen defined by the microcatheter, and wherein the pusherwire comprises a first hub and an implant receiving section configured to receive the device.

14. A device for insertion into a lumen of a ductus arteriosus for maintaining a patency of the ductus arteriosus, comprising:

a first end section comprising a first plurality of struts configured to expand to define a proximal face having a first diameter;

a second end section comprising a second plurality of struts configured to expand to define a distal face having a second diameter;

a body section extending between the first end section and the second end section and defining a third diameter, the body section having a third plurality of struts, wherein the body section comprises a crown to bridge ratio of about 6:3 to about 9:3; and a device lumen extending through the first end section, the body section, and the second end section such that blood is configured to flow through the device lumen, wherein the device is configured to transition from a crimped configuration to an expanded configuration, such that, in the crimped configuration, a crimped diameter of the device is sized to pass through a lumen of a microcatheter and, in the expanded configuration, the device is configured to expand to an expansion diameter of greater than about 3 mm measured at the body section, and wherein the device, in the expanded configuration, has a radial resistive force greater than about 0.30 N/mm at 1 mm of compression.

15. The device of claim 14, wherein, in the expanded configuration, each of the first diameter of the proximal face and the second diameter of the distal face is larger by about 1 mm to about 2 mm than the third diameter of the body section.

16. The device of claim 14, further comprising:

a delivery system comprising a microcatheter and a pusherwire, wherein the pusherwire is configured to be advanced through a lumen defined by the microcatheter, and wherein the pusherwire comprises a first hub and an implant receiving section configured to receive the device.

17. The device of claim 14, wherein a terminal subset at the proximal face of the first plurality of struts forms a proximal angle with respect to a longitudinal axis of the device;

and wherein a terminal subset at the distal face of the second plurality of struts forms a distal angle with respect to a longitudinal axis of the device.

18. The device of claim 17, wherein each of the proximal angle and the distal angle is about 30 degrees to about 110 degrees.

19. The device of claim 14, wherein the third diameter of the body section in the expanded configuration is undersized by about 40% to about 140% relative to a lumen of the ductus arteriosus on prostaglandins.

20. The device of claim 19, wherein, in the expanded configuration, the first diameter of the proximal face is about 20% to about 50% larger than the third diameter of the body section, and wherein, in the expanded configuration, the second diameter of the distal face is about 20% to about 50% larger than the third diameter of the body section.

21. The device of claim 14, wherein:

each of the first plurality of struts has a first length, each of the second plurality of struts has a second length, and each of the third plurality of struts has a third length;

the third length is shorter than the first length; and the third length is shorter than the second length.

22. The device of claim 21, wherein the first length of each of the first plurality of struts and the second length of each of the second plurality of struts is about 2.5 mm to about 4 mm; and wherein the third length of each of the third plurality of struts in about 1 mm to about 2 mm.

* * * * *